(12) United States Patent
Codallos, Jr. et al.

(10) Patent No.: US 10,398,693 B2
(45) Date of Patent: Sep. 3, 2019

(54) PHARMACEUTICAL COMPOSITIONS AND DOSAGE FORMS

(71) Applicant: Ignyta, Inc., San Diego, CA (US)

(72) Inventors: Daniel Codallos, Jr., San Diego, CA (US); Robert Orr, San Clemente, CA (US); Ching-Yuan Li, San Diego, CA (US); Valerie Denise Start, San Diego, CA (US)

(73) Assignee: IGNYTA, INC., San Diego, CA (US)

( * ) Notice: Subject to any disclaimer, the term of this patent is extended or adjusted under 35 U.S.C. 154(b) by 0 days.

(21) Appl. No.: 16/039,196

(22) Filed: Jul. 18, 2018

(65) Prior Publication Data

US 2019/0022089 A1 Jan. 24, 2019

Related U.S. Application Data

(60) Provisional application No. 62/534,585, filed on Jul. 19, 2017.

(51) Int. Cl.
| | | |
|---|---|---|
| A61K 31/496 | (2006.01) | |
| A61P 35/00 | (2006.01) | |
| A61K 9/20 | (2006.01) | |
| A61K 9/50 | (2006.01) | |
| A61K 31/194 | (2006.01) | |
| A61K 31/197 | (2006.01) | |
| A61K 47/02 | (2006.01) | |
| A61K 47/12 | (2006.01) | |
| A61K 47/26 | (2006.01) | |
| A61K 47/38 | (2006.01) | |
| A61K 9/16 | (2006.01) | |
| A61K 9/48 | (2006.01) | |

(52) U.S. Cl.
CPC .......... *A61K 31/496* (2013.01); *A61K 9/1617* (2013.01); *A61K 9/1623* (2013.01); *A61K 9/2013* (2013.01); *A61K 9/2018* (2013.01); *A61K 9/2059* (2013.01); *A61K 9/2086* (2013.01); *A61K 9/2095* (2013.01); *A61K 9/485* (2013.01); *A61K 9/4858* (2013.01); *A61K 9/4866* (2013.01); *A61K 9/5089* (2013.01); *A61K 31/194* (2013.01); *A61K 31/197* (2013.01); *A61K 47/02* (2013.01); *A61K 47/12* (2013.01); *A61K 47/26* (2013.01); *A61K 47/38* (2013.01); *A61P 35/00* (2018.01)

(58) Field of Classification Search
CPC .............................. A61K 31/035; A61P 35/00
See application file for complete search history.

(56) References Cited

U.S. PATENT DOCUMENTS

| | | |
|---|---|---|
| 4,555,402 A | 11/1985 | Matsuda et al. |
| 7,015,231 B2 | 3/2006 | Lackey et al. |
| 7,230,098 B2 | 6/2007 | Cui et al. |
| 7,534,792 B2 | 5/2009 | Wittman et al. |
| 7,790,756 B2 | 9/2010 | Flynn et al. |
| 7,799,782 B2 * | 9/2010 | Munson ............... C07D 231/56 514/234.5 |
| 7,964,592 B2 | 6/2011 | Garcia-Echeverria et al. |
| 8,114,865 B2 | 2/2012 | Bandiera et al. |
| 8,114,989 B2 | 2/2012 | Wang et al. |
| 8,299,057 B2 * | 10/2012 | Lombardi Borgia ....................... C07D 231/56 514/210.21 |
| 8,372,858 B2 | 2/2013 | Michellys et al. |
| 8,404,846 B2 | 3/2013 | Claridge et al. |
| 8,497,284 B2 | 7/2013 | Bannen et al. |
| 8,513,263 B2 | 8/2013 | Haas et al. |
| 8,673,893 B2 | 3/2014 | Lombardi Borgia et al. |
| 8,680,111 B2 | 3/2014 | Bailey et al. |
| 9,102,662 B2 | 8/2015 | Lombardi Borgia et al. |
| 10,085,979 B2 | 10/2018 | Hornby et al. |
| 10,231,965 B2 | 3/2019 | Lim et al. |
| 2004/0014802 A1 | 1/2004 | Dutruc-Rosset et al. |
| 2005/0014829 A1 * | 1/2005 | Remenar ............... C07C 211/42 514/554 |
| 2009/0263397 A1 | 10/2009 | Buck et al. |
| 2010/0197665 A1 | 8/2010 | Bandiera et al. |
| 2013/0018036 A1 | 1/2013 | Lombardi Borgia et al. |
| 2014/0107107 A1 | 4/2014 | Gautschi et al. |
| 2015/0051222 A1 | 2/2015 | Barbugian et al. |
| 2015/0283132 A1 | 10/2015 | Lim et al. |
| 2017/0007599 A1 | 1/2017 | Lim et al. |
| 2017/0065582 A1 | 3/2017 | Hornby et al. |
| 2018/0177792 A1 | 6/2018 | Wei |
| 2018/0333412 A1 | 11/2018 | Lim et al. |
| 2019/0000840 A1 | 1/2019 | Li et al. |
| 2019/0022089 A1 | 1/2019 | Codallos et al. |
| 2019/0070173 A1 | 3/2019 | Hornby et al. |

FOREIGN PATENT DOCUMENTS

| | | |
|---|---|---|
| CN | 101594862 | 12/2009 |
| CN | 101754956 | 6/2010 |
| CN | 102924479 A | 2/2013 |
| JP | 2002-275068 A | 9/2002 |
| JP | 2010-530840 A | 9/2010 |
| JP | 2011-502959 A | 1/2011 |
| WO | WO9943302 * | 9/1999 |
| WO | WO-03/051847 A1 | 6/2003 |
| WO | WO-03/078403 A2 | 9/2003 |
| WO | WO-2004/007676 A1 | 1/2004 |
| WO | WO-2004/022544 A1 | 3/2004 |
| WO | WO-2004/062662 A1 | 7/2004 |
| WO | WO-2004/075898 A1 | 9/2004 |

(Continued)

OTHER PUBLICATIONS

U.S. Appl. No. 16/249,703, filed Jan. 16, 2019, Ignyta, Inc.

(Continued)

*Primary Examiner* — Rei Tsang Shiao
(74) *Attorney, Agent, or Firm* — Foley & Lardner, LLP

(57) ABSTRACT

Disclosed herein are pharmaceutical compositions and dosage forms including N-[5-(3,5-difluorobenzyl)-1H-indazol-3-yl]-4-(4-methyl-piperazin-1-yl)-2-(tetrahydro-2H-pyran-4-ylamino) benzamide that are useful in the treatment of subjects having cancer. The present disclosure also provides methods for preparing these pharmaceutical compositions and dosage forms, and methods of treating subjects having cancer utilizing the pharmaceutical compositions and dosage forms provided herein.

25 Claims, 4 Drawing Sheets

(56) References Cited

FOREIGN PATENT DOCUMENTS

| WO | WO-2005/040413 A1 | 5/2005 |
|---|---|---|
| WO | WO-2006/003276 A1 | 1/2006 |
| WO | WO-2006/080450 A1 | 8/2006 |
| WO | WO-2006/111035 A1 | 10/2006 |
| WO | WO-2007/017497 A2 | 2/2007 |
| WO | WO-2007/075847 A2 | 7/2007 |
| WO | WO-2008/003396 A1 | 1/2008 |
| WO | WO-2008/073480 A1 | 6/2008 |
| WO | WO-2008/074749 A1 | 6/2008 |
| WO | WO-2009/013126 A1 | 1/2009 |
| WO | WO-2013/119950 A2 | 8/2013 |
| WO | WO-2013/174876 A1 | 11/2013 |
| WO | WO-2014/093750 A1 | 6/2014 |
| WO | WO-2015/124697 A1 | 8/2015 |
| WO | WO-2015/189814 A1 | 12/2015 |
| WO | WO-2016/089760 A1 | 6/2016 |
| WO | WO-2016/089853 A1 | 6/2016 |
| WO | WO-2017/106492 A1 | 6/2017 |

OTHER PUBLICATIONS

Adriaenssens, E. et al., Nerve growth factor is a potential therapeutic target in breast cancer, Cancer Res, Jan. 15, 2008, 68(2):346-351.

Albaugh, P. et al., Discovery of GNF-5837, a selective TRK inhibitor with efficacy in rodent cancer tumor models, Med. Chem. Lett, 2012, 3:140-145.

Alecensa® (alectinib) capsules, for oral use, Prescribing Information, Dec. 2015, 16 pages.

Asaumi, K. et al., Expression of neurotrophins and their receptors (TRK) during facture healing, Bone, Jun. 2000, 26(6);625-633.

Aveic et al., "Study of pan-Trk, ROS1, ALK inhibitor, RXDX-101, activity on human neuroblastoma cell lines", Brochure, SIOPEN Annual Meeting 2014, Apr. 23-25, 2014. (1 page).

Awad et al., "ALK inhibitors in non-small cell lung cancer: crizotinib and beyond", Clin Adv Hemotol Oncol, Jul. 2014, 12(7):429-439.

Bardelli, A. et al., Mutational analysis of the tyrosine kinome in colorectal cancers, Science, 2003, 300:949.

Bardelli, A. et al., Mutational analysis of the tyrosine kinome in colorectal cancers, Science, 2003, 300:949; Supplemental Material.

Baserga, R. et al., The IGF-I receptor in cell growth, transformation and apoptosis, Biochip Biophys Acta, 1997, 1332:F105-F126.

Bavetsias, V. et al., Hit generation and exploration: imidazo[4,5-b]pyridine derivatives as inhibitors of aurora kinases, Bioorganic & Medicinal Chemistry Letters, 2007, 17:6567-6571.

Bergethon, K. et al., ROS1 rearrangements define a unique molecular class of lung cancers, Journal of Clinical Oncology, Mar. 10, 2012, 30(8):863-870.

Bouhana, K. et al., LOXO-101, a pan TRK inhibitor, for the treatment of TRK-driven cancers, 26th EORTC-NCI-AACR Symposium on Molecular Targets and Cancer Therapeutics, Barcelona, Spain, Poster, Nov. 2014, Abstract #291, 1 p.

Brodeur et al., "TrK Receptor Expression and Inhibition in Neuroblastomas," Clinical Cancer Research, 15(10), pp. 3244-3250, 2009.

Brodeur, G. M., Neuroblastoma: biological insights into a clinical enigma, Nat. Rev. Cancer, Mar. 2003, 3:203-216.

Brodeur, GM, et al. Trk receptor expression and inhibition in neuroblastomas. Clin Cancer Res. May 15, 2009;15(10):3244-50.

Broekman, F. et al., Tyrosine kinase inhibitors: multi-targeted or single-targeted?, World J. Clin Oncol, Feb. 10, 2011, 2(2):80-93.

Brose, M. et al., LOXO-101, a selective pan-TRK inhibitor for patients with TRK-alterations 15th International Thyroid Congress, Oct. 2015, Lake Buena Vista, Florida, Poster, 1 p.

Brzezianska, E. et al., Rearrangements of NTRK1 oncogene in papillary thyroid carcinoma, Neuroendocrinology Letters, 2007, 28(3):221-229.

Burris, H. A., III. et al., A first-in-human study of LOXO-101, a highly selective inhibitor of the tropomyosin receptor kinase (TRK) family, American Society of Clinical Oncology (ASCO) 2015 Annual Meeting, May-Jun. 2015, Chicago, IL, Poster, 1 p.

Calvo, E., Posters Discussion: Developmental Therapeutics, 2014 ESMO Congress, Sep. 26-30, 2014, 21 pp.

Cho, H. et al., Expression of mRNA for brain-derived neurotrophic factor in the dorsal root ganglion following peripheral inflammation, Brain Research, 1997, 749:358-362.

ClinicalTrials.gov, Aug. 20, 2014, A phase 1/2a study of oral RXDX-101 in adult patients with locally advanced or metastatic cancer; study targeting ALK, ROS1 or TRKA/8/C (STARTRK:1), 4 pp.

ClinicalTrials.gov, Aug. 2014, A phase 1/2a study of oral RXDX-101 in adult patients with locally advanced or metastatic cancer; study targeting ALK, ROS1 or TRKA/8/C, 36 pp.

ClinicalTrials.gov, Sep. 11, 2014, a phase 1/2a study oforal RXDX-101 in adult patients with locally advanced or metastatic cancer; study targeting ALK, ROS1 or TRKA/8/C (STARTRK-1), 7 pp.

Cohen, P., Protein kinases—the major drug targets of the twenty-first century?, Nature Reviews, Apr. 2002, Drug Discovery 1:309-315.

Cohen, P., The development and therapeutic potential of protein kinase inhibitors, Current Opinion in Chemical Biology, 1999, 3:459-465.

Collymore, D. C. et al., Genomic testing in oncology to improve clinical outcomes while optimizing utilization: the evolution of diagnostic testing, American Journal of Managed Care, Feb. 2016, 22(2):S20-S28.

Croucher et al., "TrkB inhibition by GNF-4256 slows growth and enhances chemotherapeutic efficacy in neuroblastoma xenografts", Cancer Chemother Pharmacol, 2015, 75:131-141.

Dang, C. et al., Expression of nerve growth factor receptors is correlated with progression and prognosis of human pancreatic cancer, Journal of Gastroenterology and Hepatology, 2006, 21(5):850-858.

Davidson, B. et al., Expression and activation of the nerve growth factor receptor TrkA in serous ovarian carcinoma, Clin. Cancer Res., Jun. 2003, 9:2248-2259.

Davies, K. D. et al., Resistance of ROS1 inhibition mediated by EGFR pathway activation in non-small cell lung cancer, PIOS One, Dec. 2013, 8(12):e82236.

Davies, K. et al., Identifying and targeting ROS1 gene fusions in non-small cell lung cancer, Clin Cancer Res, Sep. 1, 2012, 18(17):4570-4579.

De Braud, F. et al., 2014, Phase 1 open label, dose escalation study of RXDX-101, an oral pan-trk, ROS1, and ALK inhibitor, in patients with advanced solid tumors with relevant molecular alterations, Poster, 1P.

De Braud, F. et al., 2014, RXDX-101, an oral pan-Trk, POS1, and ALK inhibitor, in patients with advanced solid tumors with relevant molecular alterations, Annals of Oncology 25(Supplement 4):iv146-iv164 (abstract).

De Braud, F., 2014, Phase 1 open label, dose escalation study of RXDX-101, an oral pan-trk, ROS1, and ALK inhibitor, in patients with advanced solid tumors with relevant molecular alterations, PowerPoint presentation, ASCO 50th Annual Meeting, 18 pp.

De Melo-Jorge, M. et al., The chagas' disease parasite trypanosoma cruzi exploits nerve growth factor receptor TrkA to infect mammalian hosts, Cell Host & Microbe, Jun. 2007, 1(4):251-261.

Delafoy, L. et al., Role of nerve growth factor in the trinitrobenzene sulfonic acid-induced colonic hypersensitivity, Pain, 2003, 105:489-497.

Di Mola, F. F. et al., Nerve growth factor and Trk high affinity receptor (TrkA)gene expression in inflammatory bowel disease, Gut, 2000, 46(5):670-678.

Dionne, C. A. et al., Cell cycle-independent death of prostate adenocarcinoma is induced by the trk tyrosine kinase inhibitor CEP-751 (KT6587), Clin. Cancer Res., Aug. 1998, 4(8):1887-1898.

Doebele, R. C. et al., An oncogenic NTRK fusion in a patient with soft-tissue sarcoma with response to the tropomyosin-related kinase inhibitor LOXO-101, Cancer Discovery, Oct. 2015, 1049-1057.

(56) References Cited

OTHER PUBLICATIONS

Dou, Y. et. al., 2006, Increased nerve growth factor and its receptors in atopic dermatitis: an immunohistochemical study, Archives of Dermatological Research, 2008, 298(1):31-37.
Drilon et al., "Safety and Antitumor Activity of the Multitargeted Pan-TRK, ROS1, and ALK Inhibitor Entrectinib: Combined Results from Two Phase I Trials (ALKA-372-001 and STARTRK-1)", Published OnlineFirst Feb. 9, 2017, Downloaded from cancerdiscovery.aacrjournals.org on Apr. 7, 2017, pp. 401-409.
Drug Class Detail: Trk Receptor Inhibitor (Pan); https://ckb.jax.org/drugClass/show?drugClassId=Trk Receptor Inhibitor %28Pan%29: (Jul. 16, 2014).
Duffy, M. J. et al., Companion biomarkers: paving the pathway to personalized treatment for cancer, Clinical Chemistry, 2013, 59(1):1447-1456.
Estrada-Bernal et al., "TRK kinase domain mutations that induce resistance to a pan-TRK inhibitor", [abstract]. In: Proceedings of the AACR-NCI-EORTC International Conference: Molecular Targets and Cancer Therapeutics; Nov. 5-9, 2015; Boston, MA. Philadelphia (PA): AACR; Mol Cancer Ther 2015;14(12 Suppl 2):Abstract nr C65.
Evans et al., "Antitumor Activity of CEP-751 (KT-6587) on Human Neuroblastoma and Medulloblastoma Xenografts", American Association for Cancer Research, 1999, 5:3594-3602.
Freund-Michel, V. et al., The nerve growth factor and its receptors in airway inflammatory diseases, Pharmacology & Therapeutics, 2008, 117(1):52-76.
Gad et al., "Neurotrophic activities of trk receptors conserved over 600 million years of evolution", J. Neurobiol., 2004;60(1):12-20.
Gainor, Justin, MD,RXDX-101 & RXDX-102, PowerPoint Presentation, Feb. 20, 2014, 13 pp.
Greco, A. et al., Rearrangement of NKRK1 gene in papillary thyroid carcinoma, Molecular and Cellular Endocrinology, May 1, 2010, 321(1):44-49.
Hansen, K. et al., Autophagic cell death induced by TrkA receptor activation in human glioblastoma cells, Journal of Neurochemistry, 2007, 103:259-275.
Hofmann, F. et al., Blocking insulin-like growth factor-I receptor as a strategy for targeting cancer, Drug Discov Today, Aug. 2005, 10(15):1041-1047.
Hu, V. Y. et al., Decrease in bladder overactivity with ren1820 in rats with cyclophosphamide induced cystitis, The Journal of Urology, 2005, 173(3):1016-1021.
Hu, Y. et al., Identification of brain-derived neurotrophic factor as a novel angiogenic protein in multiple myeloma, Cancer Genetics and Cytogenetics, 2007, 178:1-10.
Iannone et al., "Increased expression of nerve growth factor (NGF) and high affinity NGF receptor (p140 TrkA) in human osteoarthritic chondrocytes", Rheumatology, 2002;41:1413-1418.
Ignyta Inc., Aug. 12, 2014, Ignyta announces second quarter 2014 company highlights and financial results, Press Release, 4 pp.
Ignyta Inc., Dec. 3, 2013, Ignyta announces completion of $54 million in private placements to catalyze precision medicine for cancer patients, Press Release, 2 pp.
Ignyta Inc., Feb. 20, 2014, Ignyta announces preliminary data from RXDX-101 phase I clinical trial, Press Release, 2 pp.
Ignyta Inc., Feb. 27, 2014, Ignyta announces of IND for RXDX-101, Press Release, 2 pp.
Ignyta Inc., Feb. 28, 2014, Ignyta announces 2013 company highlights and full year financial results, Press Release, 5 pp.
Ignyta Inc., Jul. 21, 2014, Ignyta announces initiation of STARTKR-1 global phase I/II clinical trial of RXDX-101, Press Release, 2 pp.
Ignyta Inc., May 31, 2014, Ignyta announces interim data from RXDX-101 phase I clinical trial, Press Release, 2 pp.
Ignyta Inc., May 7, 2014, Ignyta announces RXDX-101 phase I data abstract accepted for oral presentation at the 2014 ASCO annual meeting, Press Release, 2 pp.
Ignyta Inc., Nov. 1, 2013, Ignyta completes merger and announces license agreement for the development of two leading tyrosine kinase inhibitors, Press Release, 1 p.
Ignyta Inc., Nov. 18, 2014, Ignyta announces RXDX-101 phase 1 presentations at the 2014 EORTC-NCI-AACR 'molecular targets and cancer therapeutics' conference, Press Release, 2 pp.
Ignyta Inc., Nov. 7, 2014, Ignyta announces third quarter 2014 company highlights and financial results, Press Release, 5 pp.
Ignyta Inc., Sep. 15, 2014, Ignyta announces RXDX-101 phase 1 data presentation at the 2014 ESMO Congress, Press Release, 2 pp.
Ignyta Inc., Sep. 26, 2014, Ignyta announces interim data from RXDX-101 phase I clinical trial at 2014 ESMO Congress, Press Release, 2 pp.
Ignyta, Feb. 2014, Catalyzing precision medicine with integrated Rx/Ox in oncology, presentation, 23 pp.
Ignyta, Inc., Feb. 20, 2014, Form 8-K (Current Report Filing), 20 pp.
Ignyta, Inc., Jan. 13, 2014, Form 8-K (Current Report Filing), 28 pp.
Ignyta, Inc., Jun. 2, 2014, Form 8-K (Current Report Filing), 26 pp.
Ignyta, Inc., May 12, 2014, Form 8-K (Current Report Filing), 11 pp.
Ignyta, Inc., May 2, 2014, Form 8-K (Current Report Filing), 4 pp.
Ignyta, Inc., Nov. 7, 2014, Form 8-K (Current Report Filing), 13 pp.
Ignyta, Inc., Oct. 14, 2014, Form 8-K (Current Report Filing), 61 pp.
International search report issued in PCT/US2018/042756 dated Nov. 12, 2018.
Isaacson, Jerry, Ph.D. et al., "Ignyta, Inc.: Initiation of Coverage," LifeSci Advisors Research, Feb. 14, 2014, pp. 1-37.
Iyer et al., "AZ64 inhibits TrkB and enhances the efficacy of chemotherapy and local radiation in neuroblastoma xenografts", Cancer Chemother Pharmacol, 2012, 70:477-486.
Iyer et al., "Lestaurtinib Enhances the Antitumor Efficacy of Chemotherapy in Murine Xenograft Models of Neuroblastoma", Clin Cancer Res; 2010; 16(5):1478-1485.
Iyer et al., "The TRK Inhibitor Entrectinib Enhances the Efficacy of Temozolomide and Irinotecan in a Xenograft Model of Neuroblastoma", Abstract #5390, Brochure, AACR Annual Meeting 2015 (1 page).
Iyer et al., "Abstract 5390: The TRK Inhibitor RXDX-101 enhances the efficacy of temozolomide and irinotecan in a xenograft model of neuroblastoma," Cancer Research, Aug. 1, 2015, vol. 75, Iss. 15, Supplement, p. 5390.
Jaggar, S. I. et al., Inflammation of the rat urinary bladder is associated with a referred thermal hyperalgesia which is nerve growth factor dependent, Br. J. Anaesth., 1999, 83:442-448.
Jantzen, G. M. et al., "Sustained- and controlled-release drug delivery systems", in Banker et al. eds., Modern Pharmaceutics, 1996, 3rd Ed. pp. 575-609, Marcel Dekker, Inc., New York, NY.
Johnson, I . W. et al., Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a macrocyclic inhibitor of anaplastic lymphoma kinase (ALK) and c-ros oncogene 1(ROS1) with preclinical brain exposure and broad-spectrum potency against ALK-resistant mutations, Journal of Medicinal Chemistry, 2014, 57(11);4720-4744.
Karaman, M. W. et al., A quantitative analysis of kinase inhibitor selectivity, Nature Biotechnology, Jan. 2008, 26(1):127-132.
Khandwala, H. M. et al., The effects of insulin-like growth factors on tumorigenesis and neoplastic growth, Endocr Rev, 2000, 21(3):215-244.
Kruettgen, A. et al., The dark side of the NGF family: neurotrophins in neoplasias, Brain Pathology, 2006, 16:304-310.
Kushner, BH, et al. Irinotecan plus temozolomide for relapsed or refractory neuroblastoma. J Clin Oncol. Nov. 20, 2006;24(33):5271-6.
Lamant et al., 2000, Expression of the ALK tyrosine kinase gene in neuroblastoma, American Journal of Pathology, 156:1711-1721.
Lamb, K. et al., Nerve growth factor and gastric hyperalgesia in the rat, Neurogastroenterol. Motil, 2003, 15:355-361.
Laron, Z., Laron syndrome (primary growth hormone resistance or insensitivity): the personal experience 1958-2003, J Clin Endocrinol Metab, 2004, 89(3):1031-1044.
Le Roith, D. et al., The somatomedin hypothesis: 2001, Endocr Rev, 2001, 22(1):53-74.

(56) References Cited

OTHER PUBLICATIONS

Lee et al., "Mechanisms of Constitutive Activation of Janus Kinase 2-V617F Revealed at the Atomic Level Through Molecular Dynamics Simulations 1," Cancer, vol. 115, No. 8, pp. 1692-1700 (2009).
Lee, J. et al., Identification of ROS1 rearrangement in gastric adenocarcinoma, Cancer, May 1, 2013, 119:1627-1635.
Lewis et al., "The Discovery and Optimization of a Novel Class of Potent, Selective, and Orally Bioavailable Anaplastic Lymphoma Kinase (ALK) Inhibitors with Potential Utility for the Treatment of Cancer", Journal of Medicinal Chemistry, 2012;55(14): 6523-6540.
Li et al., "Abstract A173: Potent anti-tumor activity of entrectinib in patient-derived models harboring oncogenic gene rearrangements of NTRKs," Molecular Cancer Therapeutics, (2015), 14(12):Supplement 2, p. A173.
Li, Q. et al., Brain derived neurotrophic factor (BDNF) contributes to the pain hypersensitivity following surgical incision in the rats, Molecular Pain, 2008, 4:27, 11 pp.
Li, T. et al., Genotyping and genomic profiling of Non-Small-Cell lung cancer: implications for current and future therapies, Journal of Clinical Oncology, Mar. 10, 2013, vol. 31, No. 8, pp. 1039-1049.
Lindeman, N. I., MD et al., Molecular testing guideline for selection of lung cancer patients for EGFR and ALK tyrosine kinase inhibitors, Journal of Thoracic Oncology, Jul. 2013, 8(7):823-859.
Lipska Beata S et al, "c.1810C>T Polymorphism of NTRK1 is associated with reduced Survival in Neuroblastoma Patients", BMC Cancer, Biomed Central, London, GB, (Dec. 2009), vol. 9, No. 1, ISSN 1471-2407, p. 436.
Ma, Q. et al., The progressive tactile hyperalgesia induced by peripheral inflammation is nerve growth factor dependent, Neuroreport, 1997, 8(4):807-810.
Marchetti, A. et al., Frequent mutations in the neurotrophic tyrosine receptor kinase gene family in large cell neuroendocrine carcinoma of the lung, Human Mutation, 2008, 29(5):609-616.
Marsilje, T. H. et al., Synthesis, structure-activity relationships and in vivo efficacy of the novel potent and selective anaplastic lymphoma kinase (ALK) inhibitor LDK378 currently in phase 1 and 2 clinical trials, J. Med. Chem., 2013, 56:5675-5690 and Supporting Information.
Matayoshi, S. et al., Actions of brain-derived neurotrophic factor on spinal nociceptive transmission during inflammation in the rat, J. Physiol., 2005, 569(2):685-695.
McMahon, S. B. et al., The biological effects of endogenous nerve growth factor on adult sensory neurons revealed by a trkA-IgG fusion molecule, Nat. Med., Aug. 1995, 1(8):774-780.
Meyer, J. et al., Remarkable leukemogenic potency and quality of a constitutively active neurotrophin receptor, ATrkA, Leukemia, 2007, 21:2171-2180.
Milkeiwicz, K. L. et al., Inhibitors of anaplastic lymphoma kinase: a patent review, Expert Opin. Ther. Patents, 2010, 20(12):1653-1681.
Minturn et al, "Phase I trial of lestaurtinib for children with refractory neuroblastoma: a new approaches to neuroblastoma therapy consortium study," Cancer Chemother Pharmacol, Feb. 22, 2011, 9 pages.
Molina-Vila, M. A. et al., Impact of the new EGF receptor and ALK testing guideline on personalized lung cancer medicine, Personalized Medicine, 2013, 19(5):415-417.
Murphy et al., "Monitoring activity of RXDX-101 in Phase 1/2 patients using a pharmacodynamics assay for TrkA activation", European Journal of Cancer, Poster Session—Molecular Targeted Agents II, 2014, 50(6):143-144.
Nakagawara et al.; "Association between high levels of expression of the Trk gene and favorable outcome in human neuroblastoma"; N Engl J Med; 1993; 328:847-54.
Nakagawara, A., Trk receptor tyrosine kinases: a bride between cancer and neural development, Cancer Letters, 2001, 169:107-114.
National Comprehensive Cancer Network, NCCN Clinical Practice Guidelines in Oncology: Non-small cell lung cancer, Apr. 2016, Version 4.2016. 169 pp.

Okimoto, R. A. et al., Recent advances in personalized lung cancer medicine, Personalized Medicine, 2014, 11(3):309-321.
Omura et al., "A New Alkaloid AM-2282 of Streptomyces Origin Taxonomy, Fermentation, Isolation and Preliminary Characterization", Journal of Antibiotics, 1977, 30(4):275-282.
Pardue et al., "Nucleic Acid Hybridization. A practical approach", IRL Press, Oxford Washington/DC. 1985:170-203.
Patapoutain, A. et al., Trk receptors: mediators of neurotrophin action, Current Opinion in Neurobiology, 2001, 11:272-280.
Perez-Pinera,P. et al., The Trk tyrosine kinase inhibitor K252a regulates growth on lung adenocarcinomas, Molecular and Cellular Biochemistry, 2007, 295:19-26.
Pierotti, A. et al., Oncogenic rearrangements of the NRTK1/NGF receptor, Cancer Letters, 2006, 232:90-98.
Pinski, J. et al., Trk receptor inhibition induced apoptosis of proliferating but not quiescent human osteoblasts, Cancer Research, Feb. 15, 2002, 62:986-989.
Puig de la Bellacasa, R. et al., ALK and ROS1 as a joint target for the treatment of lung cancer: a review, Translational Lung Cancer Research, 2013, vol. 2, No. 2, pp. 72-86.
Raychaudhuri, S. P. et al., K252a, a high-affinity nerve growth factor receptor blocker, improves psoriasis: an in vivo study using the severe combined immunodeficient mouse-human skin model, Journal of Investigative Dermatology, Mar. 3, 2004, 122(3);812-819.
Russo et al., "Acquired Resistance to the TRK Inhibitor Entrectinib in Colorectal Cancer," Cancer Discovery, (2016), 6:36-44.
Sakamoto, H. et al., CH5424802, a selective ALK inhibitor capable of blocking the resistant gatekeeper mutant, Cancer Cell, 2011, 19:679-690.
Shaw, A. T. et al., Crizotinib versus chemotherapy in advanced ALK-positive lung cancer, The New England Journal of Medicine, Jun. 30, 2013, 268(25):2385-2394.
Shaw, A. T. et al., Targeting anaplastic lymphoma kinase in lung cancer, Clin. Cancer Res., 2011, 17:2081-2086.
Shelton, D. et al., Nerve growth factor mediates hyperalgesia and cachexia in auto-immune arthritis, Pain, 2005, 116:8-16.
Sohrabji, F. et al., Estrogen-BDNF interactions: implications for neurodegenerative diseases, Neuroendocrinology, 2006, 27(4):404-414.
Stumpfova, M. et al., Zeroing in on ROS1 rearrangements in non-small cell lung cancer, Clin Cancer Res, Aug. 2, 2012, 18(16):4222-4224.
Tatematsu, T. et al., Investigation of neurotrophic tyrosine kinase receptor 1 fusions and neurotrophic tyrosine kinase receptor family expression in non-small-cell lung cancer and sensitivity to AZD7451 in vitro, Molecular and Clinical Oncology, 2014, 2:725-730.
Thompson S. W. N. et al., Brain-derived neurotrophic factor is an endogenous modulator of nociceptive responses in the spinal cord, Proc. Natl. Acad. Sci. USA, Jul. 1999, 96:7714-7718.
Tremodar PI-2, Highlights or Prescribing Information, 2014. (17 pages).
Truzzi, F. et al., Neurotrophins and their receptors stimulate melanoma cell proliferation and migration, Journal of Investigative Dermatology, 2008, 128(8):2031-2040.
Tzelepi, V., Editorial: Personalized cancer treatment, Current Molecular Pharmacology, 2014, 7(1), 2 pp.
Uniprot Accession P04629. "NTRK1_human", (Jun. 24, 2015), available on the internet: http://www.uniprot.org/uniprot/P04629.txt?version=204 (12 pages).
Vaishnavi, A. et al., Oncogenic and drug sensitive NTRK1 rearrangements in lung cancer, Nat Med., Nov. 2013, 19(11):1469-1472.
Valent, A. et al. Mapping of the tyrosine kinase receptors trkA (NTRK1), trkB (NTRK2) and trkC(NTRK3) to human chromosomes 1q22, 9q22 and 15q25 by fluorescence in situ hybridization. Eur.J. Hum. Genet (1997), vol. 5(2), pp. 102-104.
Valentinis, B. et al., IGF-I receptor signaling in transformation and differentiation, 2001, Mol Pathol, 54:133-137.

(56) References Cited

OTHER PUBLICATIONS

Vasconcelos et al., "Solid dispersions a strategy to improve oral bioavailability of poor water soluble drug," Drug Discovery Today, vol. 12, Jan. 2012, pp. 1068-1075.

Voskoglou-Nomikos, T. et al., Clinical predictive value of the in vitro cell line, human xenograft, and mouse allograft preclinical cancer models, Clinical Cancer Research, Sep. 15, 2003, 9:4227-4239.

Wang, Y. et al., Insulin-like growth factor receptor-1 as an anticancer target: blocking transformation and inducing apoptosis, Curr Cancer Drug Targets, 2002, 2:191-207.

Warner, S. et al., Targeting aurora-2 kinase in cancer, Molecular Cancer Therapeutics, Jun. 3, 2003, 2:589-595.

Wei et al., "Abstract 2136: Entrectinib is effective against the gatekeeper and other emerging resistance mutations in NTRK-, ROS1- and ALK-rearranged cancers", [abstract], Proceedings: AACR 107th Annual Meeting 2016; Apr. 16-20, 2016: New Orleans, LA; 2016;76(14 Suppl):Abstract nr 2136.

Weroha, S. J. et al., IFG-1 receptor inhibitors in clinical trials-early lessons, J. Mammary Gland Biol. Neoplasia, 2008, vol. 13, pp. 471-483.

Wolff, M.E., Burger's Medicinal Chemistry and Drug Discovery, 5th Ed. vol. 1, 1995, pp. 975-977, John Wiley & Sons, Inc., New York, NY.

Wood et al., "Somatic Mutations of GUCY2F, EPHA3, and NTRK3 in Human Cancers", Human Mutation in Brief #923, 2006. (9 pages).

Woolf, C. J. et al., Letter to Neuroscience: Nerve growth factor contributes to the generation of inflammatory sensory hypersensitivity, Neuroscience, 1994, vol. 62, No. 2, pp. 327-331.

Xalkori® (crizotinib) capsules, for oral use, Prescribing Information, Mar. 2016, 27 pp.

Zahn, P. et al., Effect of blockade of nerve growth factor and tumor necrosis factor on pain behaviors after plantar incision, J. Pain, vol. 5 No. 3, Apr. 2004, pp. 157-163.

Zhu et al., "Nerve Growth Factor expression Correlates With Perineural Invasion and Pain in Human Pancreatic Cancer", Journal of Clinical Oncology, 1999;17:2419-2428.

Zhu, L., et al. Implications of tropomyosin-related kinase B (TrkB) in head and neck cancer. Anticancer Res. Sep.-Oct. 2007;27(5A):3121-6.

Zykadia™ (ceritinib) capsules, for oral use, Prescribing Information, Apr. 2014, 16 pp.

\* cited by examiner

PHARMACEUTICAL COMPOSITIONS AND DOSAGE FORMS

CROSS REFERENCE TO RELATED APPLICATIONS

This application claims the benefit of and priority to U.S. Provisional Patent Application No. 62/534,585, filed Jul. 19, 2017, the contents of which are hereby incorporated by reference herein in their entirety.

FIELD

The present disclosure relates to pharmaceutical compositions and dosage forms that are useful in the treatment of subjects having cancer. The present disclosure also provides methods for preparing these pharmaceutical compositions and dosage forms, and methods of treating subjects having cancer utilizing the pharmaceutical compositions and dosage forms provided herein.

BACKGROUND

The compound N-[5-(3,5-difluorobenzyl)-1H-indazol-3-yl]-4-(4-methyl-piperazin-1-yl)-2-(tetrahydro-2H-pyran-4-ylamino)-benzamide and its preparation have been disclosed in U.S. Pat. No. 8,299,057, the contents of which are hereby incorporated by reference in their entirety. N-[5-(3,5-difluorobenzyl)-1H-indazol-3-yl]-4-(4-methyl-piperazin-1-yl)-2-(tetrahydro-2H-pyran-4-ylamino)-benzamide is a potent inhibitor of tyrosine kinases, NTRK1/2/3-transforming tyrosine kinase proteins (TrkA, TrkB, TrkC), proto-oncogene tyrosine-protein kinase 1 (ROS1), and anaplastic lymphoma kinase (ALK). In various in vitro studies, N-[5-(3,5-difluorobenzyl)-1H-indazol-3-yl]-4-(4-methyl-piperazin-1-yl)-2-(tetrahydro-2H-pyran-4-ylamino)-benzamide inhibited proliferation of the CRC cell line KM12, which depends upon TrkA kinase activity for proliferation and survival. It was also potent in inhibiting cell proliferation of ALK-dependent Anaplastic Large Cell Lymphoma cell lines.

In a single-dose food effect study in dogs of N-[5-(3,5-difluorobenzyl)-1H-indazol-3-yl]-4-(4-methyl-piperazin-1-yl)-2-(tetrahydro-2H-pyran-4-ylamino)-benzamide, in a formulation that did not comprise at least one acidulant, exposure levels of N-[5-(3,5-difluorobenzyl)-1H-indazol-3-yl]-4-(4-methyl-piperazin-1-yl)-2-(tetrahydro-2H-pyran-4-ylamino)-benzamide in the dogs were approximately 2-fold higher under fed conditions compared to those observed under fasting conditions. Such food effects can cause difficulty during human testing of drugs as the fed or fasted condition of the patient can cause exposure or bioavailability of drugs to vary widely.

In early clinical studies in humans, N-[5-(3,5-difluorobenzyl)-1H-indazol-3-yl]-4-(4-methyl-piperazin-1-yl)-2-(tetrahydro-2H-pyran-4-ylamino)-benzamide has been shown to have antitumor effects in patients having various forms of cancer having at least one molecular alteration in one or more of ALK, ROS1, TrkA, TrkB and TrkC. In the studies using a formulation of N-[5-(3,5-difluorobenzyl)-1H-indazol-3-yl]-4-(4-methyl-piperazin-1-yl)-2-(tetrahydro-2H-pyran-4-ylamino)-benzamide that did not comprise at least one acidulant, systemic exposure of N-[5-(3,5-difluorobenzyl)-1H-indazol-3-yl]-4-(4-methyl-piperazin-1-yl)-2-(tetrahydro-2H-pyran-4-ylamino)-benzamide increased when co-administered with food. In particular, N-[5-(3,5-difluorobenzyl)-1H-indazol-3-yl]-4-(4-methyl-piperazin-1-yl)-2-(tetrahydro-2H-pyran-4-ylamino)-benzamide AUC values were approximately 200% and 50% higher using N-[5-(3,5-difluorobenzyl)-1H-indazol-3-yl]-4-(4-methyl-piperazin-1-yl)-2-(tetrahydro-2H-pyran-4-ylamino)-benzamide doses of 200 mg/m$^2$/day and 400 mg/m$^2$/day, respectively when taken with food. Cmax values were approximately 150% higher with food for both doses. In addition, some patients in these studies received N-[5-(3,5-difluorobenzyl)-1H-indazol-3-yl]-4-(4-methyl-piperazin-1-yl)-2-(tetrahydro-2H-pyran-4-ylamino)-benzamide and concomitant proton pump inhibitor drugs (PPIs), such as lansoprazole, and demonstrated variable N-[5-(3,5-difluorobenzyl)-1H-indazol-3-yl]-4-(4-methyl-piperazin-1-yl)-2-(tetrahydro-2H-pyran-4-ylamino)-benzamide exposures. Moreover, dose proportionality was lost at doses higher than 800 mg/m$^2$/day. As such, it is an object of the present disclosure to provide pharmaceutical compositions and dosage forms comprising N-[5-(3,5-difluorobenzyl)-1H-indazol-3-yl]-4-(4-methyl-piperazin-1-yl)-2-(tetrahydro-2H-pyran-4-ylamino)-benzamide that do not suffer from the variability in absorption in subjects, such as humans, when dosed with or without food and in the presence or absence of PPIs.

SUMMARY

In some embodiments are provided pharmaceutical compositions, comprising a weakly basic organic compound and at least one acidulant. In some embodiments, the at least one acidulant is an organic acidulant. In some embodiments, the at least one acidulant is selected from tartaric acid, maleic acid, fumaric acid, citric acid, and betaine hydrochloride. In some embodiments, the at least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In any of the embodiments described herein, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein the molar ratio between said N-[5-(3,5-difluorobenzyl)-1H- indazol-3-yl]-4-(4-methyl-piperazin-1-yl)-2-(tetrahydro-pyran-4-ylamino)-benzamide and said at least one acidulant is from about 0.5 to about 2.

In some embodiments are provided pharmaceutical compositions in the form of a tablet or capsule. In some embodiments are provided pharmaceutical compositions in the form of a tablet. In some embodiments are provided pharmaceutical compositions in the form of a capsule.

In some embodiments are provided pharmaceutical compositions, wherein said pharmaceutical composition comprises from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide and at least one acidulant.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide degrades in said pharmaceutical composition after said pharmaceutical composition is stored for 3 months in an open container at 40° C. and 75% relative humidity.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least acidulant, wherein more than about 98% of said N-[5-(3,5-difluorobenzyl)-1H-indazol-3-yl]-4-(4-methyl-piperazin-1-yl)-2-(tetrahydro-pyran-4-ylamino)-benzamide is present in said pharmaceutical composition after said pharmaceutical composition is stored for 3 months in an open container at 40° C. and 75% relative humidity.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide degrades in said pharmaceutical composition after said pharmaceutical composition is stored for 3 months in an open container at 60° C. and 75% relative humidity.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said compositions are non-hygroscopic.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one pharmaceutically acceptable excipient, wherein said pharmaceutical composition is in the form of a tablet or capsule, and wherein said tablet or capsule has a dissolution profile wherein at least about 30% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 60 minutes when tested in USP Apparatus Type I Basket Method at 50 rpm in 500 mL of sodium acetate buffer at a pH of 4.5 and at about 37° C. In some embodiments are provided such pharmaceutical formulations wherein at least about 40%, or about 50%, or about 60%, or about 70%, or about 80%, or about 90%, or about 95% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 60 minutes when tested in USP Apparatus Type I Basket Method at 50 rpm in 500 mL of sodium acetate buffer at a pH of 4.5 and at about 37° C.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, wherein said wherein said tablet or capsule has a dissolution profile wherein at least about 20% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 45 minutes when tested in USP Apparatus Type I Basket Method at 50 rpm in 500 mL of sodium acetate buffer at a pH of 4.5 and at about 37° C.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, wherein said wherein said tablet or capsule has a dissolution profile wherein at least about 15% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 30 minutes when tested in USP Apparatus Type I Basket Method at 50 rpm in 500 mL of sodium acetate buffer at a pH of 4.5 and at about 37° C.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and 6 hours following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2080 nM and about 2110 nM following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between 80% to 125% of 2560 nM, based on a 90 percent confidence interval following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 28,900 nM*hr and about 30,800 nM*hr following said administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2080 nM and about 2100 nM following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 28,900 nM*hr and about 30,800 nM*hr following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 6 hours following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering said N-[5-(3,5-difluorobenzyl)-1H-indazol-3-yl]-4-(4-methyl-piperazin-1-yl)-2-(tetrahydro-pyran-4-ylamino)-benzamide to a subject that exhibits no food effect.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering said N-[5-(3,5-difluorobenzyl)-1H-indazol-3-yl]-4-(4-methyl-piperazin-1-yl)-2-(tetrahydro-pyran-4-ylamino)-benzamide to a subject that exhibits no significant food effect.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, wherein said pharmaceutical composition exhibits no food effect when administered to a subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, wherein said pharmaceutical composition exhibits no food effect when administered to a subject and said subject is also administered one or more proton pump inhibitor compounds.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 5 hours following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 8 hours following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran- 4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4 hours and about 8 hours following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4 hours and about 8 hours following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and about 3500 nM, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and about 3500 nM, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC (infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC (infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1200 nM and about 3500 nM following administration of said pharmaceutical composition to said subject in a fasted state, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1200 nM and about 3500 nM following administration of said pharmaceutical composition to said subject, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1500 nM and about 3500 nM following administration of said pharmaceutical composition to said subject in a fed state, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1500 nM and about 3500 nM following administration of said pharmaceutical composition to said subject, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 30,000 nM*hr and about 85,000 nM*hr following administration of said pharmaceutical composition to said subject in a fasted state, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 30,000 nM*hr and about 85,000 nM*hr following administration of said pharmaceutical composition to said subject, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 35,000 nM*hr and about 90,000 nM*hr following administration of said pharmaceutical composition to said subject in a fed state, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 35,000 nM*hr and about 90,000 nM*hr following administration of said pharmaceutical composition to said subject, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 30,000 nM*hr and about 85,000 nM*hr following administration of said pharmaceutical composition to said subject in a fasted state, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 30,000 nM*hr and about 85,000 nM*hr following administration of said pharmaceutical composition to said subject, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 35,000 nM*hr and about 90,000 nM*hr following administration of said pharmaceutical composition to said subject in a fed state, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 35,000 nM*hr and about 90,000 nM*hr following administration of said pharmaceutical composition to said subject, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 5 hours following administration of said pharmaceutical composition to said subject in a fasted state, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 5 hours following administration of said pharmaceutical composition to said subject, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 8 hours following administration of said pharmaceutical composition to said subject in a fed state, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 8 hours following administration of said pharmaceutical composition to said subject, and wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

DETAILED DESCRIPTION

Figure 1:
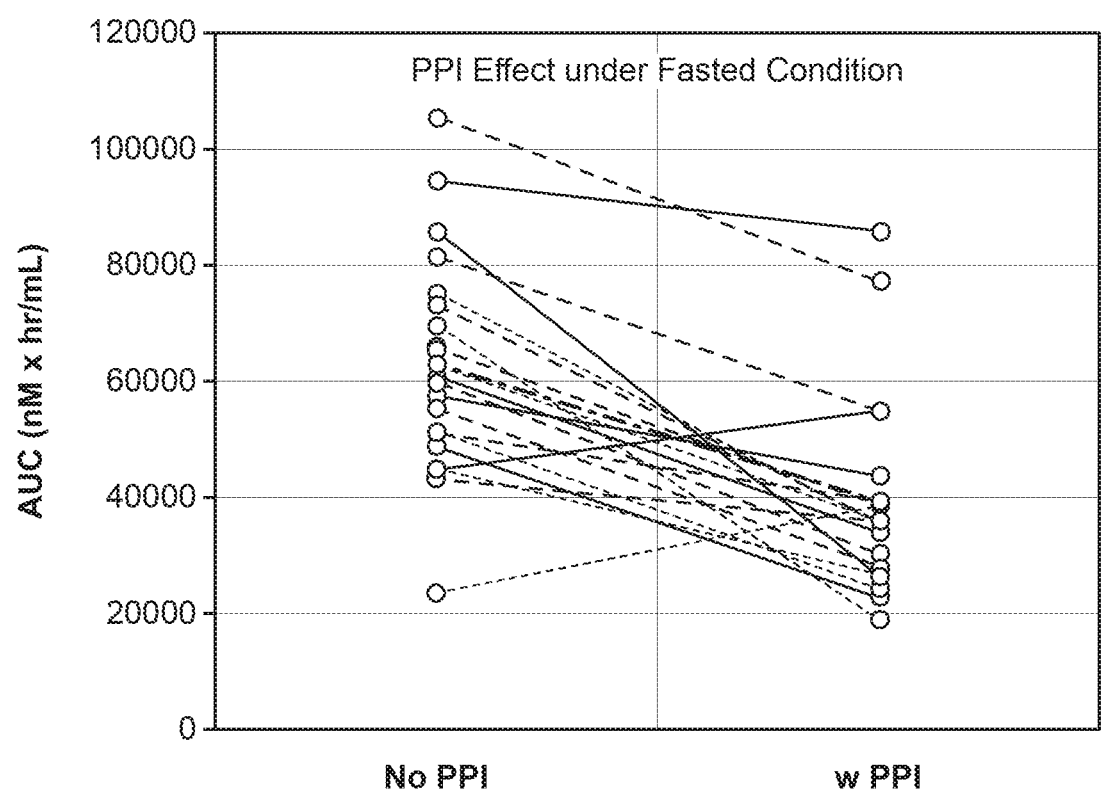
FIG. 1 is a graphical illustration of the bioavailability (area under the curve, AUC) of N-[5-(3,5-difluorobenzyl)-1H-indazol-3-yl]-4-(4-methyl-piperazin-1-yl)-2-(tetrahydro-pyran-4-ylamino)-benzamide, measured in nM*hr/mL, after administration of the F2A formulation under fasted conditions, with and without a PPI.

The singular form "a," "an," and "the" include plural references unless the context clearly dictates otherwise. For example, the term "a cell" includes one or more cells, including mixtures thereof. "A and/or B" is used herein to include all of the following alternatives: "A," "B," "A or B," and "A and B."

As used herein, the term "N-[5-(3,5-difluorobenzyl)-1H-indazol-3-yl]-4-(4-methyl-piperazin-1-yl)-2-(tetrahydro-pyran-4-ylamino)-benzamide" means a compound having Chemical Abstracts Service Registry No. 1108743-60-7 and having the chemical structure:

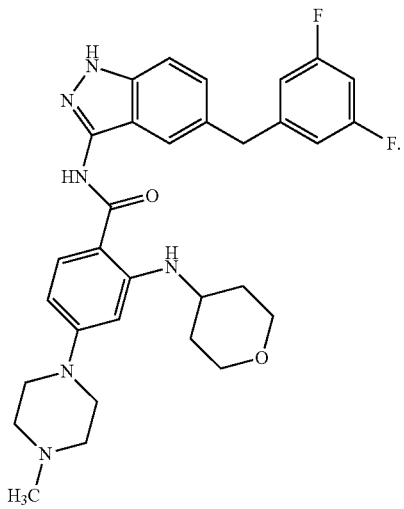 [SMILES: CN1CCN(c2ccc(C(=O)Nc3n[nH]c4ccc(Cc5cc(F)cc(F)c5)cc34)c(NC3CCOCC3)c2)CC1]

Hereinafter all references to N-[5-(3,5-difluorobenzyl)-1H-indazol-3-yl]-4-(4-methyl-piperazin-1-yl)-2-(tetrahydro-pyran-4-ylamino)-benzamide herein include references to solvates, complexes, polymorphic forms, stereoisomers, and isotopically labeled versions thereof. Also included within the scope provided herein are pharmaceutical compositions comprising solvates, complexes, polymorphic forms, stereoisomers, and isotopically labeled versions of N-[5-(3,5-difluorobenzyl)-1H-indazol-3-yl]-4-(4-methyl-piperazin-1-yl)-2-(tetrahydro-pyran-4-ylamino)-benzamide.

As used herein, the term "about" means either within plus or minus 10% of the provided value, or rounded to the nearest significant figure, in all cases inclusive of the provided value. Where ranges are provided, they are inclusive of the boundary values.

As used herein, the term "acidulant" means a chemical compound that is acidic in nature. As used herein, the term "organic acidulant" means an acidulant the chemical composition of which contains carbon. As used herein, the term "inorganic acidulant" means an acidulant the composition of which does not contain carbon.

As used herein, the terms "administration" and "administering" mean the delivery of a bioactive composition or formulation to a subject by an administration route including, but not limited to, oral, intravenous, intra-arterial, intramuscular, intraperitoneal, subcutaneous, intramuscular, topically, or combinations thereof. In some embodiments, the administration to a subject is oral.

As used herein, the term "admixture" means a mixture of one or more chemical compounds in a composition. It is understood by one having ordinary skill in the art that the pharmaceutical compositions disclosed herein comprise an admixture of N-[5-(3,5-difluorobenzyl)-1H-indazol-3-yl]-4-(4-methyl-piperazin-1-yl)-2-(tetrahydro-pyran-4-ylamino)-benzamide and the at least one acidulant.

As used herein, the term "ALK" means anaplastic lymphoma kinase receptor or CD246 (cluster of differentiation 246), which is an enzyme that in humans is encoded by the ALK gene and also has the UniProt identified ALK_HUMAN.

As used herein, the term "antibody" means an immunoglobulin that specifically binds to, and is thereby defined as complementary with, a particular spatial and polar organization of another molecule. The antibody can be monoclonal or polyclonal and can be prepared by techniques that are well known in the art, such as immunization of a host and collection of sera (polyclonal), or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular target is maintained.

As used herein, the term "AUC" means the area under the curve of a plot of the concentration of a compound in the plasma of a subject versus time.

As used herein, the term "betaine hydrochloride" means a compound having Chemical Abstracts Service Registry No. 590-46-5 and the common names 1-carboxy-n,n,n- trimethylmethanaminium chloride and (carboxymethyl) trimethylammonium hydrochloride.

As used herein, the term "biological sample," means a sample obtained from an organism that may be used in a diagnostic or monitoring assay. The sample may be of a healthy tissue, diseased tissue or tissue suspected of being diseased tissue. The sample may be a biopsy taken, for example, during a surgical procedure. The sample may be collected via means of fine needle aspiration, scraping or washing a cavity to collects cells or tissue therefrom. The sample may be of a tumor such as, for example, solid and hematopoietic tumors as well as of neighboring healthy tissue. The sample may be a smear of subject cells or a tissue section. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses clinical samples, and also includes cells in cell culture, cell supernatants, cell lysates, cell extracts, cell homogenates, and subcellular components including synthesized proteins, serum, plasma, bodily and other biological fluids, and tissue samples. The biological sample can contain compounds that are not naturally intermixed with the cell or tissue in nature such as preservatives, anticoagulants, buffers, fixatives, nutrients, antibiotics or the like. In some embodiments, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

As used herein, the term "biomarker" means one or more compounds whose level of nucleic acid or protein product has a quantitatively differential concentration or level with respect to an aspect of a biological state of a subject. The term "biomarker" may be used herein interchangeably with the term "marker." The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present disclosure include those associated with ALK, ROS1, TrkA, TrkB, and TrkC.

As used herein, the term "$C_{max}$" means the peak concentration that a compound achieves in the plasma of a subject after the compound, or a pharmaceutical composition comprising the compound, has been administrated to the subject. In some embodiments, the compound, or a pharmaceutical composition comprising the compound, is administered orally to a subject to achieve a particular $C_{max}$.

As used herein, the terms "cancer" or "tumor" may be used interchangeably. These terms mean the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers. In certain embodiments, the cancer is a solid tumor, a soft tissue tumor, or a metastatic lesion. The terms also refer to solid tumors named for the type of cells that form them, cancer of blood, bone marrow, or the lymphatic system. Examples of solid tumors include, but are not limited to, sarcomas and carcinomas. Examples of cancers of the blood include, but are not limited to, leukemias, lymphomas and myeloma. The terms include, but are not limited to, a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. As used herein "cancer" refers to any malignant and/or invasive growth or tumor caused by abnormal cell growth.

As used herein, the term "chemotherapeutic agent", means a chemical substance, such as a cytotoxic or cytostatic agent, that is used to treat a condition, particularly cancer.

As used herein, the terms "combination" and "in combination with" mean the administration of N-[5-(3,5-difluorobenzyl)-1H-indazol-3-yl]-4-(4-methyl-piperazin-1-yl)-2-(tetrahydro-pyran-4-ylamino)-benzamide together with at least one additional pharmaceutical or medicinal agent (e.g., an anti-cancer agent), either sequentially or simultaneously. It includes dosing simultaneously, or within minutes or hours of each other, or on the same day, or on alternating days, or dosing the pharmaceutical compositions provided herein on a daily basis, or multiple days per week, or weekly basis, for example, while administering another compound such as a chemotherapeutic agent on the same day or alternating days or weeks or on a periodic basis during a time simultaneous therewith or concurrent therewith, or at least a part of the time during which the pharmaceutical compositions disclosed herein is dosed. For example, a pharmaceutical composition as provided herein that comprises N-[5-(3,5-difluorobenzyl)-1H-indazol-3-yl]-4-(4-methyl-piperazin-1-yl)-2-(tetrahydro-pyran-4-ylamino)-benzamide could be dosed every day or several days a week while the chemotherapeutic agent is dosed on alternating days or alternating weeks or other periods of time, such as every 1, 2, 3, 4, 5, 6, 7, 8, 9, 10, 11, 12, 13, 14 or more days.

As used herein, the term "contact" when used in reference to specificity or specific binding means two molecules are close enough so that short range non-covalent chemical interactions, such as Van der Waal forces, hydrogen bonding, hydrophobic interactions, and the like, dominate the interaction of the molecule.

As used herein, the term "cell line" means to one or more generations of cells which are derived from a clonal cell. The term "clone," or "clonal cell," means a single cell which is expanded to produce an isolated population of phenotypically similar cells (i.e. a "clonal cell population").

As used herein, the parameters Dv10, Dv50, Dv90 and Dv99 represent the particle size at the 10%, 50%, 90% and 99% points of the cumulative volume undersize particle size distribution. Thus, a "Dv10" for a material represents a particle size wherein 10% of the volume of the material consists of particles having a particle size equal to the Dv10 value or smaller. A "Dv50" for a material represents a particle size wherein 50% of the volume of the material consists of particles having a particle size equal to the Dv50 value or smaller. A "Dv90" for a material represents a particle size wherein 90% of the volume of the material consists of particles having a particle size equal to the Dv90 value or smaller. A "Dv99" for a material represents a particle size wherein 99% of the volume of the material consists of particles having a particle size equal to the Dv99 value or smaller.

As used herein, the term "food effect" means a change in the rate and/or extent of absorption of a compound in a subject when the compound is administered to the subject shortly after a meal (fed conditions) as compared to the rate and/or extent of absorption of the compound when the compound is administered to the subject under fasting conditions. As used herein, the term "no food effect" means that there is no significant difference in the rate and/or extent of absorption of a compound in a subject when the compound is administered to the subject in fed conditions compared to fasting conditions.

As used herein, the term "immunohistochemistry," means the process of localizing antigens (e.g. proteins) in biological samples, cells and/or cells of a tissue section exploiting the principle of antibodies binding specifically to antigens. Immunohistochemical staining is widely used in the diagnosis of abnormal cells such as those found in cancerous tumors. Specific molecular markers are characteristic of particular cellular events, such as cell proliferation or cell death. Visualizing an antibody-antigen interaction can be accomplished in a number of ways. In the most common instance, an antibody is conjugated to an enzyme, such as peroxidase, that can catalyze a color-producing reaction. Alternatively, the antibody can also be tagged to a fluorophore thus employing the principles of immunofluorescence. Immunohistochemistry can also be used to evaluate tumor content in the sample on which qPCR is carried out in order to account for the fact that qPCR result will be influenced by the amount of tumor tissue present.

As used herein, the term "micronization" refers to a process of reducing the average particle size of a solid material, typically to provide particles with a particle size of a few micrometers.

As used herein, the term "micronized" means a material that has been subjected to micronization As used herein, the terms "monoclonal antibody," "mAb" and "MAB" mean an antibody that is an immunoglobulin produced by a single clone of lymphocytes which recognizes only a single epitope on an antigen. For example, a monoclonal antibody useful for the methods provided herein displays a single binding specificity and affinity for a particular epitope of one or more tyrosine kinases.

As used herein, the term "multiplexed assay" means an assay in which multiple assay reactions, e.g. simultaneous assays of multiple target biomarkers, are carried out in a single reaction chamber and/or and analyzed in a single separation and detection format.

As used herein, the term "multiplex identification" means the simultaneous identification of one or more target biomarkers in a single mixture. For example, a two-plex assay means the simultaneous identification, in a single reaction mixture, of two different target biomarkers.

As used herein, the term "one or more molecular alterations" means any variation in the genetic or protein sequence in one or more cells of a subject as compared to the corresponding wild-type genes or proteins. One or more molecular alterations include, but are not limited to, genetic mutations, gene amplifications, splice variants, deletions, insertions/deletions, gene rearrangements, single-nucleotide variations (SNVs), insertions, and aberrant RNA/protein expression.

As used herein, the term "particle size distribution" means the relative proportions of particles of a compound having a given particle size. While the particle size of a spherical object can be unambiguously and quantitatively defined by its diameter, particles comprising an active pharmaceutical ingredient or an excipient may be non-spherical and irregular in shape. There are several methods by which those of ordinary skill in the art measure and express the size of non-spherical and irregular particles, such as measuring the size of such particles using laser diffractometry and expressing the size of such particles based on replacing a given particle with an imaginary sphere that has one of a number of properties of the particle. Such properties can be selected from, for example, but are not limited to, the diameter of an imaginary sphere having the same volume of the particle being measured (volume-based particle size), the diameter of an imaginary sphere having the same weight as the particle being measured (weight-based particle size), and the diameter of an imaginary sphere having the same surface area as the particle being measured (area-based particle size). Those having ordinary skill in the art are familiar with such methods, and the manner in which the results of such methods are expressed, and such methods can be applied to the embodiments disclosed herein without undue experimentation. The particle size distribution may be represented, for example, graphically as a plot. A common type of plot is a cumulative undersize plot which represents the fraction (e.g. by number, volume or mass) of particles that are smaller than the stated particle size.

As used herein, the term "polyclonal antibody" means a composition of different antibody molecules which is capable of binding to or reacting with several different specific antigenic determinants on the same or on different antigens. The variability in antigen specificity of a polyclonal antibody is located in the variable regions of the subject antibodies constituting the polyclonal antibody, in particular in the complementarity determining regions (CDRs). Preferably, the polyclonal antibody is prepared by immunization of an animal with the target tyrosine kinases or portions thereof. Alternatively, the polyclonal antibody may be prepared by mixing multiple monoclonal antibodies having desired specificity to a target tyrosine kinase.

As used herein, the term "proton pump inhibitor" or "PPI" refers to a drug that reduces gastric acid production. PPIs that may be used in some embodiments includes herein are, but are not limited to, dexlansoprazole, esomeprazole, ilaprazole, lansoprazole, omeprazole, pantoprazol, picoprazole, rabeprazole, yenatoprazole, and timoprazole.

As used herein, "ROS1" means the ROS1 receptor tyrosine-protein kinase having the UniProt designation ROS1 HUMAN.

As used herein, the term "selectively binds" means the situation in which one member of a specific intra- or inter-species binding pair will not show any significant binding to molecules other than its specific intra- or inter-species binding partner (e.g., an affinity of about 100-fold less), which means that only minimal cross-reactivity occurs.

As used herein in reference to the binding of two molecules or one or more compounds and a complex of molecules, the term "specific" means the specific recognition of one for the other and the formation of a stable complex, as compared to substantially less recognition of other molecules and the lack of formation of stable complexes with such other molecules. Preferably, "specific," in reference to binding, means that to the extent that one or more compounds forms complexes with other molecules or complexes, it forms at least fifty percent of the complexes with the molecule or complex for which it has specificity. Generally, the molecules or complexes have areas on their surfaces or in cavities giving rise to specific recognition between the two binding moieties. Exemplary of specific binding are antibody-antigen interactions, enzyme-substrate interactions, polynucleotide hybridizations and/or formation of duplexes, cellular receptor-ligand interactions, and so forth.

As used herein, the term "subject" means a mammal, including, but not limited to, a human, a dog or a cat. In some embodiments, the subject is a human. In some embodiments, the subject is a dog. In some embodiments, the subject is a cat.

As used herein, the term "$T_{max}$" means the time when the peak concentration of a compound in the plasma of a subject is reached after administration of the compound, or a pharmaceutical composition comprising the compound, to the subject.

As used herein, the term "therapeutically effective amount" means that amount of the compound or compounds, or pharmaceutically acceptable salts thereof, being administered to a subject which will relieve to some extent one or more of the symptoms of the disorder being treated. In reference to the treatment of a cancer, a therapeutically effective amount means that amount which has the effect of (1) reducing the size of a cancer tumor, (2) inhibiting (that is, slowing to some extent, preferably stopping) cancer tumor metastasis, (3) inhibiting to some extent (that is, slowing to some extent, preferably stopping) cancer tumor growth, and/or, (4) relieving to some extent (or, preferably, eliminating) one or more symptoms associated with the cancer.

As used herein, the terms "tropomyosin receptor kinase," "Trks" and "Trk" mean the family of tropomyosin receptor kinases (Trks) that are activated by peptide hormones of the neurotrophin family and include, but are not limited to, TrkA, TrkB, and TrkC. As used herein, the term "TrkA" means wild-type tropomyosin receptor kinase A having the UniProt identifier NTRK1_HUMAN. As used herein, the term "TrkB" means wild-type tropomyosin receptor kinase B having the UniProt identifier NTRK2_HUMAN. As used herein, the term "TrkC" means wild-type tropomyosin receptor kinase C having the UniProt identifier NTRK3_HUMAN. TrkA, TrkB and TrkC are also referred to by those having ordinary skill in the art as Trk1, Trk2 and Trk3, respectively. A reference to TrkA is a reference to Trk1. A reference to TrkB is a reference to Trk2. A reference to TrkC is a reference to Trk3

As used herein, the term "USP Apparatus Type I" means the Apparatus 1 (Basket Apparatus or Basket Method) and the procedures for using the apparatus that are described in United States Pharmacopeia (USP) General Chapter <711>.

As used herein, the term "USP Apparatus Type II" means the Apparatus 2 (Paddle Apparatus or Paddle Method) and the procedures for using the apparatus described in United States Pharmacopeia (USP) General Chapter <711>.

In one aspect are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, at least one acidulant and at least one pharmaceutically acceptable excipient.

In one aspect are provided pharmaceutical compositions comprising an admixture of N-[5-(3,5-difluorobenzyl)-1H-indazol-3-yl]-4-(4-methyl-piperazin-1-yl)-2-(tetrahydro-pyran-4-ylamino)-benzamide, at least one acidulant and at least one pharmaceutically acceptable excipient.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, at least one acidulant and at least one pharmaceutically acceptable excipient. Among the acidulants that may be used in the pharmaceutical compositions disclosed herein are organic and inorganic acidulants. In some embodiments, the at least one acidulant is an organic acidulant. In some embodiments, the at least one acidulant is an inorganic acidulant. In some embodiments, the at least one organic acidulant is selected from organic carboxylic acids, aminium, and iminium salts.

In some embodiments, the acidulant is selected from acetic acid, ascorbic acid, benzoic acid, benzosulfonic acid, betaine hydrochloride, carbonic acid, cinnamic acid, citric acid, ethanesulfonic acid, ethylenediaminetetraacetic acid, dodecylsulfonic acid, fumaric acid, glucoronic acid, glutamic acid, glycolic acid, lactic acid, lactobionic acid, (D) or (L) malic acid or a mixture thereof, maleic acid, mandelic acid, malonic acid, methanesulfonic acid, mucic acid, naphthalenesulfonic acid, propionic acid, salicylic acid, stearic acid, succinic acid, p-toluenesulfonic acid, trifluoroacetic acid, (D) or (L) tartaric acid or a mixture thereof, valeric acid, and the like.

In some embodiments, the at least one acidulant is selected from acetic acid, benzoic acid, betaine hydrochloride, citric acid, fumaric acid, glucoronic acid, lactic acid, (D) or (L) malic acid or a mixture thereof, maleic acid, mandelic acid, malonic acid, salicylic acid, stearic acid, succinic acid, p-toluenesulfonic acid, and (D) or (L) tartaric acid or a mixture thereof.

In some embodiments, the at least one acidulant is selected from benzoic acid, betaine hydrochloride, citric acid, fumaric acid, (D) or (L) maleic acid or a mixture thereof, and (D) or (L) tartaric acid or a mixture thereof.

In some embodiments, the at least one acidulant is selected from betaine hydrochloride, citric acid, fumaric acid, maleic acid, and (D) or (L) tartaric acid or a mixture thereof.

In some embodiments, the at least one acidulant is betaine hydrochloride. In some embodiments, the at least one acidulant is citric acid. In some embodiments, the at least one acidulant is fumaric acid. In some embodiments, the at least one acidulant is maleic acid. In some embodiments, the at least one acidulant is (D) or (L) tartaric acid or a mixture thereof.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein the at least one acidulant is (D)-tartaric acid. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein the at least one acidulant is (L)-tartaric acid.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition is prepared using wet granulation.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition is prepared using dry granulation. In some embodiments, inclusion of at least one acidulant in the dry granulation step of drug product manufacturing creates a low pH micro environment that enhances the solubility of N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition is prepared using wet granulation and the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride. In some embodiments, the at least one acidulant is (D) or (L) tartaric acid or a mixture thereof. In some embodiments, the at least one acidulant is (D) tartaric acid. In some embodiments, the at least one acidulant is (L) tartaric acid. In some embodiments, the at least one acidulate is a mixture of (D) and (L) tartaric acid.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition is prepared using dry granulation and the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride. In some embodiments, the at least one acidulant is (D) or (L) tartaric acid or a mixture thereof. In some embodiments, the at least one acidulant is (D) tartaric acid. In some embodiments, the at least one acidulant is (L) tartaric acid. In some embodiments, the at least one acidulate is a mixture of (D) and (L) tartaric acid.

In some embodiments, the at least one acidulant has a melting point of greater than or equal to about 15° C. In some embodiments, the at least one acidulant has a melting point of greater than or equal to about 20° C. In some embodiments, the at least one acidulant has a melting point of greater than or equal to about 25° C. In some embodiments, the at least one acidulant has a melting point of greater than or equal to about 30° C. In some embodiments, the at least one acidulant has a melting point of greater than or equal to about 40° C. In some embodiments, the at least one acidulant has a melting point of greater than or equal to about 50° C. In some embodiments, the at least one acidulant has a melting point of greater than or equal to about 75° C. In some embodiments, the at least one acidulant has a melting point of greater than or equal to about 100° C. In some embodiments, the at least one acidulant has a melting point of greater than or equal to about 150° C. In some embodiments, the at least one acidulant has a melting point of greater than or equal to about 200° C. In some embodiments, the at least one acidulant has a melting point of greater than or equal to about 250° C. In some embodiments, the at least one acidulant has a melting point of greater than or equal to about 300° C.

In some embodiments, the at least one acidulant has a pKa of less than about 9, or less than about 8, or less than about 7, or less than about 6, or less than about 5, or less than about 4, or less than about 3, or less than about 2.

In some embodiments, the at least one acidulant has a pKa of from about 1 to about 9, or from about 1 to about 8, or from about 1 to about 7, or from about 1 to about 6, or from about 1 to about 5, or from about 1 to about 4, or from about 1 to about 3.5, or from about 1 to about 3.25, or from about 1 to about 3, or from about 1 to about 2.75, or from about 1 to about 2.5, or from about 1 to about 2.25, or from about 1 to about 2, or from about 1 to about 1.9, or from about 1.5 to about 5, or from about 1.5 to about 4.5, or from about 1.5 to about 4, or from about 1.5 to about 3.5, or from about 1.5 to about 3.25, or from about 1.8 to about 3.5.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 0.5 to about 2, or from about 0.75 to about 1.75, or from about 1 to about 1.75, or from about 1 to about 1.5, or from about 1.25 to about 1.75, or from about 1 to about 1.5.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is about 2, or about 1.75, or about 1.5, or about 1.25, or about 1, or about 0.75, or about 0.5. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is about 1.5.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said at least one acidulant is (D) tartaric acid, (L) tartaric acid, or a mixture of (D) and (L) tartaric acid, and further wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is about 2, or about 1.75, or about 1.5, or about 1.25, or about 1, or about 0.75, or about 0.5. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said at least one acidulant is (D) tartaric acid, (L) tartaric acid, or a mixture of (D) and (L) tartaric acid, and further wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is about 1.5.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 0.5 to about 5, or from about 0.5 to about 4.5, or from about 0.5 to about 4, or from about 0.5 to about 3.5, or from about 0.5 to about 3, or from about 0.5 to about 2.75, or from about 0.5 to about 2.5, or from about 0.5 to about 2.25.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is from about 0.5 to about 5, or from about 0.5 to about 4.5, or from about 0.5 to about 4, or from about 0.5 to about 3.5, or from about 0.5 to about 2.75, or from about 0.5 to about 2.5, or from about 0.5 to about 2.25.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 0.5. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 1. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 1.5. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 2. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 2.25. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 2.5. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 2.75. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 3. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 3.5. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 4. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 4.5. In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and betaine hydrochloride, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said betaine hydrochloride is about 5.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant. In some embodiments, the formulations comprise from about 10 mg to about 1000 mg, or from about 25 mg to about 1000 mg, or from about 50 mg to about 1000 mg, or from about 100 mg to about 1000 mg, or from about 100 mg to about 800 mg, or from about 100 mg to about 750 mg, or from about 100 mg to about 500 mg, or from about 100 mg to about 300 mg, or from about 100 mg to about 250 mg, or from about 100 mg to about 200 mg, or from about 100 mg to 150 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 475 mg, or about 500 mg, or about 525 mg, or about 550 mg, or about 575 mg, or about 600 mg, or about 625 mg, or about 650 mg, or about 700 mg, or about 750 mg, or about 800 mg, or about 850 mg, or about 900 mg, or about 950 mg, or about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 25 mg, or about 50 mg, or about 75 mg, or about 100 mg, or about 125 mg, or about 150 mg, or about 175 mg, or about 200 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 100 mg, or about 125 mg, or about 150 mg, or about 175 mg, or about 200 mg, or about 225 mg, or about 250 mg, or about 275 mg, or about 300 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 150 mg, or about 175 mg, or about 200 mg, or about 225 mg, or about 250 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 100 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 150 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 200 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 250 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 300 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 350 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 400 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 450 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 500 mg of said N-[5-(3,5-difluorobenzyl)-1H-indazol-3-yl]-4-(4-methyl-piperazin-1-yl)-2-(tetrahydro-pyran-4-ylamino)-benzamide.

The embodiments of the pharmaceutical compositions provided herein are in a form suitable for oral administration, such as a tablet, capsule, powder, granule, sustained release formulations, solution suspension, suspension or emulsion. In some embodiments, the pharmaceutical compositions are in the form of a tablet or capsule. In some embodiments, the pharmaceutical compositions are in the form of a tablet. In some embodiments, the tablet is a multi-layer tablet. In some embodiments, the tablet is a multi-layer tablet wherein one or more layers comprising N-[5-(3,5-difluorobenzyl)-1H-indazol-3-yl]-4-(4-methyl-piperazin-1-yl)-2-(tetrahydro-pyran-4-ylamino)-benzamide are separate from one or more layers comprising the at least one acidulant. In some embodiments, the tablet is a bi-layer tablet wherein a layer comprising N-[5-(3,5-difluorobenzyl)-1H-indazol-3-yl]-4-(4-methyl-piperazin-1-yl)-2-(tetrahydro-pyran-4-ylamino)-benzamide is separate from a layer comprising the at least one acidulant. In some embodiments any of the multi-layer tablets described herein further comprise at least one pharmaceutically acceptable excipient.

In some embodiments, the pharmaceutical compositions are in the form of a tablet, wherein said tablet comprises N-[5-(3,5-difluorobenzyl)-1H-indazol-3-yl]-4-(4-methyl-piperazin-1-yl)-2-(tetrahydro-pyran-4-ylamino)-benzamide and at least one acidulant. In some embodiments, the pharmaceutical compositions are in the form of a tablet, wherein said tablet comprises an admixture of N-[5-(3,5-difluorobenzyl)-1H-indazol-3-yl]-4-(4-methyl-piperazin-1-yl)-2-(tetrahydro-pyran-4-ylamino)-benzamide and at least one acidulant. In some embodiments any of the tablets described herein further comprise at least one pharmaceutically acceptable excipient.

In some embodiments, the pharmaceutical compositions are in the form of a tablet, wherein said tablet comprises N-[5-(3,5-difluorobenzyl)-1H-indazol-3-yl]-4-(4-methyl-piperazin-1-yl)-2-(tetrahydro-pyran-4-ylamino)-benzamide, at least one acidulant, and at least one filler. In another embodiment, the tablets further comprise at least one disintegrant. In another embodiment, the tablets further comprise at least one glidant. In another embodiment, the tablets further comprise at least one lubricant. In another embodiment, the tablets further comprise at least one pore-forming agent. In another embodiment, the tablets further comprise at least one binder. In another embodiment, the tablets further comprise at least one gel-forming agent.

In some embodiments, the pharmaceutical compositions are in the form of a tablet, wherein said tablet comprises N-[5-(3,5-difluorobenzyl)-1H-indazol-3-yl]-4-(4-methyl-piperazin-1-yl)-2-(tetrahydro-pyran-4-ylamino)-benzamide, and at least one acidulant. In some embodiments, the at least one acidulant is selected from acetic acid, benzoic acid, betaine hydrochloride, citric acid, fumaric acid, glucoronic acid, lactic acid, (D) or (L) malic acid or a mixture thereof, maleic acid, mandelic acid, malonic acid, salicylic acid, stearic acid, succinic acid, p-toluenesulfonic acid, and (D) or (L) tartaric acid or a mixture thereof. In some embodiments, the at least one acidulant is selected from benzoic acid, betaine hydrochloride, citric acid, fumaric acid, (D) or (L) maleic acid or a mixture thereof, and (D) or (L) tartaric acid or a mixture thereof. In some embodiments, the at least one acidulant is selected from betaine hydrochloride, citric acid, fumaric acid, maleic acid, and (D) or (L) tartaric acid or a mixture thereof. In some embodiments, the at least one acidulant is betaine hydrochloride. In some embodiments, the at least one acidulant is citric acid. In some embodiments, the at least one acidulant is fumaric acid. In some embodiments, the at least one acidulant is maleic acid. In some embodiments, the at least one acidulant is (D) or (L) tartaric acid or a mixture thereof.

In some embodiments, the pharmaceutical compositions are in the form of a tablet, wherein said tablet comprises N-[5-(3,5-difluorobenzyl)-1H-indazol-3-yl]-4-(4-methyl-piperazin-1-yl)-2-(tetrahydro-pyran-4-ylamino)-benzamide, at least one acidulant, and magnesium stearate. In some embodiments the at least one acidulant is selected from acetic acid, benzoic acid, betaine hydrochloride, citric acid, fumaric acid, glucoronic acid, lactic acid, (D) or (L) malic acid or a mixture thereof, maleic acid, mandelic acid, malonic acid, salicylic acid, stearic acid, succinic acid, p-toluenesulfonic acid, and (D) or (L) tartaric acid or a mixture thereof. In some embodiments, the at least one acidulant is selected from benzoic acid, betaine hydrochloride, citric acid, fumaric acid, (D) or (L) maleic acid or a mixture thereof, and (D) or (L) tartaric acid or a mixture thereof. In some embodiments, the at least one acidulant is selected from betaine hydrochloride, citric acid, fumaric acid, maleic acid, and (D) or (L) tartaric acid or a mixture thereof. In some embodiments, the at least one acidulant is betaine hydrochloride. In some embodiments, the at least one acidulant is citric acid. In some embodiments, the at least one acidulant is fumaric acid. In some embodiments, the at least one acidulant is maleic acid. In some embodiments, the at least one acidulant is (D) or (L) tartaric acid or a mixture thereof.

In some embodiments, the pharmaceutical compositions are in the form of a capsule. In some embodiments, the capsule is a multi-layer capsule. In some embodiments, the capsule is a multi-layer capsule wherein one or more layers comprising N-[5-(3,5-difluorobenzyl)-1H-indazol-3-yl]-4-(4-methyl-piperazin-1-yl)-2-(tetrahydro-pyran-4-ylamino)-benzamide are separate from one or more layers comprising the at least one acidulant. In some embodiments, the capsule is a bi-layer capsule wherein a layer comprising N-[5-(3,5-difluorobenzyl)-1H-indazol-3-yl]-4-(4-methyl-piperazin-1-yl)-2-(tetrahydro-pyran-4-ylamino)-benzamide is separate from a layer comprising the at least one acidulant. In some embodiments any of the multi-layer capsules described herein further comprise at least one pharmaceutically acceptable excipient.

In some embodiments, the pharmaceutical compositions are in the form of a capsule, wherein said capsule comprises, consists of, or consists essentially of intragranular components and extragranular components within the capsule. In some embodiments, the intragranular components comprise N-[5-(3,5-difluorobenzyl)-1H-indazol-3-yl]-4-(4-methyl-piperazin-1-yl)-2-(tetrahydro-pyran-4-ylamino)-benzamide and at least one acidulant. In some embodiments, the intragranular components further comprise a filler, a binder, a disintegrant, or a lubricant, or any combination of two or more thereof. In some embodiments, the intragranular components further comprise lactose, hypromellose, crospovidone, or magnesium stearate, or any combination of two or more thereof. In some embodiments, the extragranular components comprise a filler, a disintegrant, a glidant, or a lubricant, or any combination of two or more thereof. In some embodiments, the extragranular components comprise microcrystalline cellulose, crospovidone, colloidal silicon dioxide, or magnesium stearate, or any combination of two or more thereof.

In some embodiments, the pharmaceutical compositions are in the form of a capsule, wherein said capsule comprises N-[5-(3,5-difluorobenzyl)-1H-indazol-3-yl]-4-(4-methyl-piperazin-1-yl)-2-(tetrahydro-pyran-4-ylamino)-benzamide and at least one acidulant. In some embodiments, the pharmaceutical compositions are in the form of a capsule, wherein said capsule comprises an admixture of N-[5-(3,5-difluorobenzyl)-1H-indazol-3-yl]-4-(4-methyl-piperazin-1-yl)-2-(tetrahydro-pyran-4-ylamino)-benzamide and at least one acidulant. In some embodiments any of the capsules described herein further comprise at least one pharmaceutically acceptable excipient.

In some embodiments, the pharmaceutical compositions are in the form of a capsule, wherein said capsule comprises N-[5-(3,5-difluorobenzyl)-1H-indazol-3-yl]-4-(4-methyl-piperazin-1-yl)-2-(tetrahydro-pyran-4-ylamino)-benzamide, at least one acidulant, and at least one filler. In another embodiment, the capsules further comprise at least one disintegrant. In another embodiment, the capsules further comprise at least one glidant. In another embodiment, the capsules further comprise at least one lubricant.

In some embodiments, the pharmaceutical compositions are in the form of a capsule, wherein said capsule comprises N-[5-(3,5-difluorobenzyl)-1H-indazol-3-yl]-4-(4-methyl-piperazin-1-yl)-2-(tetrahydro-pyran-4-ylamino)-benzamide, and at least one acidulant. In some embodiments, the at least one acidulant is selected from acetic acid, benzoic acid, betaine hydrochloride, citric acid, fumaric acid, glucoronic acid, lactic acid, (D) or (L) malic acid or a mixture thereof, maleic acid, mandelic acid, malonic acid, salicylic acid, stearic acid, succinic acid, p-toluenesulfonic acid, and (D) or (L) tartaric acid or a mixture thereof. In some embodiments, the at least one acidulant is selected from benzoic acid, betaine hydrochloride, citric acid, fumaric acid, (D) or (L) maleic acid or a mixture thereof, and (D) or (L) tartaric acid or a mixture thereof. In some embodiments, the at least one acidulant is selected from betaine hydrochloride, citric acid, fumaric acid, maleic acid, and (D) or (L) tartaric acid or a mixture thereof. In some embodiments, the at least acidulant is betaine hydrochloride. In some embodiments, the at least one acidulant is citric acid. In some embodiments, the at least one acidulant is fumaric acid. In some embodiments, the at least one acidulant is maleic acid. In some embodiments, the at least one acidulant is (D) or (L) tartaric acid or a mixture thereof.

In some embodiments, the pharmaceutical compositions are in the form of a capsule, wherein said capsule comprises N-[5-(3,5-difluorobenzyl)-1H-indazol-3-yl]-4-(4-methyl-piperazin-1-yl)-2-(tetrahydro-pyran-4-ylamino)-benzamide, at least one acidulant, and magnesium stearate. In some embodiments the at least one acidulant is selected from acetic acid, benzoic acid, betaine hydrochloride, citric acid, fumaric acid, glucoronic acid, lactic acid, (D) or (L) malic acid or a mixture thereof, maleic acid, mandelic acid, malonic acid, salicylic acid, stearic acid, succinic acid, p-toluenesulfonic acid, and (D) or (L) tartaric acid or a mixture thereof. In some embodiments, the at least one acidulant is selected from benzoic acid, betaine hydrochloride, citric acid, fumaric acid, (D) or (L) maleic acid or a mixture thereof, and (D) or (L) tartaric acid or a mixture thereof. In some embodiments, the at least one acidulant is selected from betaine hydrochloride, citric acid, fumaric acid, maleic acid, and (D) or (L) tartaric acid or a mixture thereof. In some embodiments, at one least acidulant is betaine hydrochloride. In some embodiments, the at least one acidulant is citric acid. In some embodiments, the at least one acidulant is fumaric acid. In some embodiments, the at least one acidulant is maleic acid. In some embodiments, the at least one acidulant is (D) or (L) tartaric acid or a mixture thereof.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg. Furthermore, the pharmaceutical compositions provided herein may contain N-[5-(3,5-difluorobenzyl)-1H-indazol-3-yl]-4-(4-methyl-piperazin-1-yl)-2-(tetrahydro-pyran-4-ylamino)-benzamide in an amount of about 50 mg, about 100 mg, about 150 mg, about 200 mg, about 250 mg, about 300 mg, about 350 mg, about 400 mg, about 450 mg, or about 500 mg. In some embodiments, the pharmaceutical compositions provided herein contain N-[5-(3,5-difluorobenzyl)-1H-indazol-3-yl]-4-(4-methyl-piperazin-1-yl)-2-(tetrahydro-pyran-4-ylamino)-benzamide in an amount of about 100 mg to about 200 mg. In some embodiments, the pharmaceutical compositions provided herein contain N-[5-(3,5-difluorobenzyl)-1H-indazol-3-yl]-4-(4-methyl-piperazin-1-yl)-2-(tetrahydro-pyran-4-ylamino)-benzamide in an amount of about 25 mg to about 800 mg.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

In some embodiments, the pharmaceutical composition further comprises lactose. In some embodiments, the lactose is present in the composition in an amount of about 15% w/w to about 35% w/w. This includes about 15, 16, 17, 18, 19, 20, 21, 22, 23, 24, 25, 26, 27, 28, 29, 30, 31, 32, 33, 34, and 35% w/v, including increments therein, and ranges between two of these values (including endpoints). In some embodiments, the lactose is present in the composition in an amount of about 25% w/w to about 30% w/w. In some embodiments, the lactose is anhydrous lactose.

In some embodiments, the pharmaceutical composition further comprises hypromellose (hydroxypropyl methylcellulose). In some embodiments, the hypromellose is present in the composition in an amount of about 1% w/w to about 10% w/w. This includes about 1, 2, 3, 4, 5, 6, 7, 8, 9, or 10% w/w, including increments therein, and ranges between two of these values (including endpoints). In some embodiments, the hypromellose is present in the composition in an amount of about 3% w/w to about 5% w/w.

In some embodiments, the pharmaceutical composition further comprises microcrystalline cellulose. In some embodiments, the microcrystalline cellulose is present in the composition in an amount of about 1% w/w to about 5% w/w. This includes about 1, 1.5, 2, 2.5, 3, 3.5, 4, 4.5, or 5% w/w, including increments therein, and ranges between two of these values (including endpoints). In some embodiments, the microcrystalline cellulose is present in the composition in an amount of about 2% w/w to about 4% w/w.

In some embodiments, the pharmaceutical composition further comprises crospovidone. In some embodiments, the crospovidone is present in the composition in an amount of about 1% w/w to about 10% w/w. This includes about 1, 1.5, 2, 2.5, 3, 3.5, 4, 4.5, 5, 5.5, 6, 6.5, 7, 7.5, 8, 8.5, 9, 9.5, or 10% w/w, including increments therein, and ranges between two of these values (including endpoints). In some embodiments, the crospovidone is present in the composition in an amount of about 4% w/w to about 7% w/w.

In some embodiments, the pharmaceutical composition further comprises colloidal silicon dioxide. In some embodiments, the colloidal silicon dioxide is present in the composition in an amount of about 0.5% w/w to about 5% w/w. This includes about 0.05, 0.10, 0.15, 0.20, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, or 5% w/w, including increments therein, and ranges between two of these values (including endpoints). In some embodiments, the colloidal silicon dioxide is present in the composition in an amount of about 0.1% w/w to about 1% w/w. In some embodiments, the colloidal silicon dioxide is present in the composition in an amount of about 0.1% w/w to about 0.5% w/w.

In some embodiments, the pharmaceutical composition further comprises magnesium stearate. In some embodiments, the magnesium stearate is present in the composition in an amount of about 0.1% w/w to about 5% w/w. This includes about 0.10, 0.15, 0.20, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, or 5% w/w, including increments therein, and ranges between two of these values (including endpoints). In some embodiments, the magnesium stearate is present in the composition in an amount of about 0.5% w/w to about 2% w/w.

In some embodiments, the pharmaceutical composition further comprises lactose, hypromellose, crospovidone, microcrystalline cellulose, colloidal silicon dioxide, or magnesium stearate, or any combination of two or more thereof. In some embodiments, the lactose is anhydrous lactose.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, tartaric acid, lactose, hypromellose (hydroxypropyl methylcellulose), crospovidone, and magnesium stearate. In some embodiments, the compositions comprise from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 25 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 50 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 800 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 750 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 500 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 300 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 250 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 200 mg of said N-[5-(3,5-difluorobenzyl)-1H-indazol-3-yl]-4-(4-methyl-piperazin-1-yl)-2-(tetrahydro-pyran-4-ylamino)-benzamide. In certain embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 475 mg, or about 500 mg, or about 525 mg, or about 550 mg, or about 575 mg, or about 600 mg, or about 625 mg, or about 650 mg, or about 700 mg, or about 750 mg, or about 800 mg, or about 850 mg, or about 900 mg, or about 950 mg, or about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 10 mg to about 100 mg of tartaric acid. This includes about 10 mg to about 90 mg, about 10 mg to about 80 mg, about 10 mg to about 70 mg, about 10 mg to about 60 mg, about 20 mg to about 100 mg, about 20 mg to about 90 mg, about 20 mg to about 80 mg, about 20 mg to about 70 mg, about 20 mg to about 60 mg, about 30 mg to about 100 mg, about 30 mg to about 90 mg, about 30 mg to about 80 mg, about 30 mg to about 70 mg, and about 30 mg to about 60 mg. In some embodiments, tartaric acid is present in the compositions in an amount of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg, including increments therein, or ranges between two of these values (including endpoints).

In some embodiments are provided pharmaceutical compositions, comprising, consisting of, or consisting essentially of N-[5-(3,5-difluorobenzyl)-1H-indazol-3-yl]-4-(4-methyl-piperazin-1-yl)-2-(tetrahydro-pyran-4-ylamino)-benzamide, tartaric acid, lactose, hypromellose (hydroxypropyl methylcellulose), microcrystalline cellulose, crospovidone, colloidal silicon dioxide, and magnesium stearate. In some embodiments, the compositions comprise from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 25 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 50 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 800 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 750 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 500 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 300 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 250 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 200 mg of said N-[5-(3,5-difluorobenzyl)-1H-indazol-3-yl]-4-(4-methyl-piperazin-1-yl)-2-(tetrahydro-pyran-4-ylamino)-benzamide. In certain embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 475 mg, or about 500 mg, or about 525 mg, or about 550 mg, or about 575 mg, or about 600 mg, or about 625 mg, or about 650 mg, or about 700 mg, or about 750 mg, or about 800 mg, or about 850 mg, or about 900 mg, or about 950 mg, or about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise about 10 mg to about 100 mg of tartaric acid. This includes about 10 mg to about 90 mg, about 10 mg to about 80 mg, about 10 mg to about 70 mg, about 10 mg to about 60 mg, about 20 mg to about 100 mg, about 20 mg to about 90 mg, about 20 mg to about 80 mg, about 20 mg to about 70 mg, about 20 mg to about 60 mg, about 30 mg to about 100 mg, about 30 mg to about 90 mg, about 30 mg to about 80 mg, about 30 mg to about 70 mg, and about 30 mg to about 60 mg. In some embodiments, tartaric acid is present in the compositions in an amount of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg, including increments therein, or ranges between two of these values (including endpoints).

In some embodiments are provided pharmaceutical compositions, comprising, consisting essentially of, or consisting of about 20% w/w to about 60% w/w N-[5-(3,5-difluorobenzyl)-1H-indazol-3-yl]-4-(4-methyl-piperazin-1-yl)-2-(tetrahydro-pyran-4-ylamino)-benzamide, about 5% w/w to about 20% w/w tartaric acid, about 15% w/w to about 35% w/w lactose, about 1% w/w to about 10% w/w hypromellose, about 1% w/w to about 5% w/w microcrystalline cellulose, about 1% w/w to about 10% w/w crospovidone, about 0.05% w/w to about 5% w/w colloidal silicon dioxide, and about 0.1% w/w to about 5% w/w magnesium stearate. In some embodiments are provided pharmaceutical compositions, comprising, consisting essentially of, or consisting of about 40% w/w to about 50% w/w N-[5-(3,5-difluorobenzyl)-1H-indazol-3-yl]-4-(4-methyl-piperazin-1-yl)-2-(tetrahydro-pyran-4-ylamino)-benzamide, about 10% w/w to about 15% w/w tartaric acid, about 25% w/w to about 30% w/w lactose, about 3% w/w to about 5% w/w hypromellose, about 2% w/w to about 4% w/w microcrystalline cellulose, about 4% w/w to about 7% w/w crospovidone, about 0.1% w/w to about 1% w/w colloidal silicon dioxide, and about 0.5% w/w to about 2% w/w magnesium stearate.

In some embodiments, a pharmaceutical compositions comprises, consists essentially of, or consists of N-[5-(3,5-difluorobenzyl)-1H-indazol-3-yl]-4-(4-methyl-piperazin-1-yl)-2-(tetrahydro-pyran-4-ylamino)-benzamide, tartaric acid, anhydrous lactose, hypromellose, microcrystalline cellulose, crospovidone, colloidal silicon dioxide, and magnesium stearate, wherein the composition is prepared in a method comprising, consisting essentially of, or consisting of:

adding N-[5-(3,5-difluorobenzyl)-1H-indazol-3-yl]-4-(4-methyl-piperazin-1-yl)-2-(tetrahydro-pyran-4-ylamino)-benzamide; anhydrous lactose; hypromellose; an intragranular portion of crospovidone; and tartaric acid together and blending to form a first admixture;

sieving the first admixture to form a sieved first admixture;

blending the sieved first admixture to form a second admixture;

sieving the second admixture to form a sieved second admixture;

blending the sieved second admixture to form a third admixture;

adding an intragranular portion of magnesium stearate to the third admixture and blending to form a fourth admixture;

compacting and milling the fourth admixture to form a fifth admixture;

adding microcrystalline cellulose, an extragranular portion of crospovidone, and colloidal silicon dioxide to the fifth admixture and blending to form a sixth admixture; and adding an extragranular portion of magnesium stearate to the sixth admixture and blending to form the pharmaceutical composition.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, fumaric acid, mannitol, pregelatinized starch, colloidal silicon dioxide, and magnesium stearate. In some embodiments, the compositions comprise from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 25 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 50 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 800 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 750 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 500 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 300 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 250 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 200 mg of said N-[5-(3,5-difluorobenzyl)-1H-indazol-3-yl]-4-(4-methyl-piperazin-1-yl)-2-(tetrahydro-pyran-4-ylamino)-benzamide. In certain embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 475 mg, or about 500 mg, or about 525 mg, or about 550 mg, or about 575 mg, or about 600 mg, or about 625 mg, or about 650 mg, or about 700 mg, or about 750 mg, or about 800 mg, or about 850 mg, or about 900 mg, or about 950 mg, or about 1000 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, betaine hydrochloride, isomalt, pregelatinized starch, colloidal silicon dioxide, and magnesium stearate. In some embodiments, the compositions comprise from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 25 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 50 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 800 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 750 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 500 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 300 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 250 mg of said N-[5-(3,5-difluorobenzyl)-1H-indazol-3-yl]-4-(4-methyl-piperazin-1-yl)-2-(tetrahydro-pyran-4-ylamino)-benzamide. In some embodiments, the compositions comprise from about 100 mg to about 200 mg of said N-[5-(3,5-difluorobenzyl)-1H-indazol-3-yl]-4-(4-methyl-piperazin-1-yl)-2-(tetrahydro-pyran-4-ylamino)-benzamide. In certain embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 475 mg, or about 500 mg, or about 525 mg, or about 550 mg, or about 575 mg, or about 600 mg, or about 625 mg, or about 650 mg, or about 700 mg, or about 750 mg, or about 800 mg, or about 850 mg, or about 900 mg, or about 950 mg, or about 1000 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide degrades in said pharmaceutical composition after said pharmaceutical composition is stored for 3 months in an open container at 40° C. and 75% relative humidity.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein more than about 98% of said N-[5-(3,5-difluorobenzyl)-1H-indazol-3-yl]-4-(4-methyl-piperazin-1-yl)-2-(tetrahydro-pyran-4-ylamino)-benzamide is present in said pharmaceutical composition after said pharmaceutical composition is stored for 3 months in an open container at 40° C. and 75% relative humidity.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide degrades in said pharmaceutical composition after said pharmaceutical composition is stored for 3 months in an open container at 60° C. and 75% relative humidity.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein more than about 98% of said N-[5-(3,5-difluorobenzyl)-1H-indazol-3-yl]-4-(4-methyl-piperazin-1-yl)-2-(tetrahydro-pyran-4-ylamino)-benzamide is present in said pharmaceutical composition after said pharmaceutical composition is stored for 3 months in an open container at 60° C. and 75% relative humidity.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one pharmaceutically acceptable excipient, wherein said pharmaceutical composition is in the form of a tablet or capsule, and wherein said tablet or capsule has a dissolution profile wherein at least about 30%, or at least about 40%, or at least about 50%, or at least about 60%, or at least about 70%, or at least about 75%, or at least about 80%, or at least about 85%, or at least about 90% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 60 minutes when tested in USP Apparatus Type I Basket Method at 50 rpm in 500 mL of sodium acetate buffer at a pH of 4.5 and at about 37° C. In some embodiments, the pharmaceutical composition further comprises at least one acidulant.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one pharmaceutically acceptable excipient, wherein said pharmaceutical composition is in the form of a tablet or capsule, and wherein said tablet or capsule has a dissolution profile wherein at least about 20%, or at least about 30%, or at least about 40%, or at least about 50%, or at least about 60%, or at least about 70% or at least about 75% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 45 minutes when tested in USP Apparatus Type I Basket Method at 50 rpm in 500 mL of sodium acetate buffer at a pH of 4.5 and at about 37° C. In some embodiments, the pharmaceutical composition further comprises at least one acidulant.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one pharmaceutically acceptable excipient, wherein said pharmaceutical composition is in the form of a tablet or capsule, and wherein said tablet or capsule has a dissolution profile wherein at least about 15%, or at least about 20%, or at least about 30%, or at least about 40%, or at least about 50% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 30 minutes when tested in USP Apparatus Type I Basket Method at 50 rpm in 500 mL of sodium acetate buffer at a pH of 4.5 and at about 37° C. In some embodiments, the pharmaceutical composition further comprises at least one acidulant.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one pharmaceutically acceptable excipient, wherein said pharmaceutical composition is in the form of a tablet or capsule, and wherein said tablet or capsule has a dissolution profile wherein at least about 10%, or at least about 15%, or at least about 20% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 15 minutes when tested in USP Apparatus Type I Basket Method at 50 rpm in 500 mL of sodium acetate buffer at a pH of 4.5 and at about 37° C. In some embodiments, the pharmaceutical composition further comprises at least one acidulant.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, at least one acidulant, and mannitol or isomalt. In some embodiments are provided pharmaceutical compositions comprising mannitol. In some embodiments are provided pharmaceutical compositions comprising isomalt.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, at least one acidulant, mannitol or isomalt, and starch. In some embodiments the weight to weight ratio of said mannitol or isomalt to said starch in said pharmaceutical composition is from about 1 to 1 to about 10 to 1, or from about 1 to 1 to about 7 to 1, or from about 1 to 1 to about 6 to 1, or from about 1 to 1 to about 5 to 1, or from about 1.5 to 1 to about 3 to 1, or from about 1.75 to 1 to about 3 to 1, or from about 1 to 1 to about 2.5 to 1, or from about 1 to 1 to about 2 to 1.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, at least one acidulant, mannitol or isomalt, and starch. In some embodiments the weight to weight ratio of said mannitol or isomalt to said starch in said pharmaceutical composition is about 10 to 1, or about 7 to 1, or about 6 to 1, or about 5 to 1, or about 4 to 1, or about 3 to 1, or about 2 to 1, or about 1.8 to 1, or about 1.5 to 1, or about 1 to 1.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, at least one acidulant and at least one pharmaceutically acceptable excipient. In some embodiments are provided pharmaceutical compositions wherein said at least one pharmaceutically acceptable excipient is selected from diluents, lubricants, binding agents, disintegrating agents, effervescing mixtures, dyestuffs, sweeteners, and wetting agents.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and 6 hours following said administration of said pharmaceutical composition to said subject. In some embodiments, the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is about 5 hours following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 5 hours and 12 hours following said administration of said pharmaceutical composition to said subject. In some embodiments, the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is about 8 hours following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2080 nM and about 2110 nM following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2080 nM and about 2560 nM following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between 80% to 125% of 2080 nM, based on a 90 percent confidence interval following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between 80% to 125% of 2560 nM, based on a 90 percent confidence interval following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 28,900 nM*hr and about 30,800 nM*hr following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is about 40,400 nM*hr following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 30,800 nM*hr at a 90% confidence interval following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 40,400 nM*hr at a 90% confidence interval following said administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2080 nM and about 2100 nM following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of about 2560 nM following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 28,900 nM*hr and about 30,800 nM*hr following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of about 40,400 nM*hr following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 6 hours following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 5 hours and about 12 hours following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2080 nM, based on a 90 percent confidence interval, following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2560 nM, based on a 90 percent confidence interval, following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 30,800 nM*hr, based on a 90 percent confidence interval, following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 40,400 nM*hr, based on a 90 percent confidence interval, following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering said N-[5-(3,5-difluorobenzyl)-1H-indazol-3-yl]-4-(4-methyl-piperazin-1-yl)-2-(tetrahydro-pyran-4-ylamino)-benzamide to a subject that exhibits no food effect.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, wherein said pharmaceutical composition exhibits no food effect when administered to a subject.

It is understood by those having ordinary skill in the art that references made to "pharmaceutical compositions provided herein," and the like, mean those pharmaceutical compositions that are described as embodiments herein. By way of example only, a method of treating a subject having cancer comprising administering to said subject a pharmaceutical composition as provided herein, means a method of treating a subject having cancer comprising administering to said subject any of the compositions described herein that comprise N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions provided herein for use as a medicament. In some embodiments, the medicament is for use in the treatment of abnormal cell growth in a mammal. In some embodiments, the abnormal cell growth is cancer. In some embodiments, the medicament is for use in the treatment of abnormal cell growth mediated by one or more of ALK, ROS1, TrkA, TrkB and TrkC in a mammal. In some embodiments, the medicament is for use in the treatment of abnormal cell growth mediated by at least one molecular alteration in one or more of ALK, ROS1, TrkA, TrkB and TrkC in a mammal. In some embodiments, the medicament is for use in the treatment of abnormal cell growth mediated by at least one molecular alteration in ALK in a mammal. In some embodiments, the medicament is for use in the treatment of abnormal cell growth mediated by at least one molecular alteration in ROS1 in a mammal. In some embodiments, the medicament is for use in the treatment of abnormal cell growth mediated by at least one molecular alteration in TrkA in a mammal. In some embodiments, the medicament is for use in the treatment of abnormal cell growth mediated by at least one molecular alteration in TrkB in a mammal. In some embodiments, the medicament is for use in the treatment of abnormal cell growth mediated by at least one molecular alteration in TrkC in a mammal. In some such embodiments, the molecular alteration is the EML4-ALK fusion protein. In some embodiments, the molecular alteration is the EML4-ALK fusion protein having at least one mutation. In some embodiments, the mutation is L1196M. In some embodiments, the mutation is C1156Y.

In some embodiments are provided methods for the treatment of abnormal cell growth in a mammal comprising administering to a mammal a therapeutically effective amount of one or more pharmaceutical compositions provided herein. In some embodiments, the abnormal cell growth is mediated by at least one molecular alteration in one or more of ALK, ROS1, TrkA, TrkB and TrkC in a mammal. In some embodiments, the abnormal cell growth is mediated by at least one molecular alteration in ALK in a mammal. In some embodiments, the abnormal cell growth is mediated by at least one molecular alteration in ROS1 in a mammal. In some embodiments, the abnormal cell growth is mediated by at least one molecular alteration in TrkA in a mammal. In some embodiments, the abnormal cell growth is mediated by at least one molecular alteration in TrkB in a mammal. In some embodiments, the abnormal cell growth is mediated by at least one molecular alteration in TrkC in a mammal. In some such embodiments, the molecular alteration is the EML4-ALK fusion protein. In some embodiments, the molecular alteration is the EML4-ALK fusion protein having at least one mutation. In some embodiments, the mutation is L1196M. In some embodiments, the mutation is C1156Y.

In some embodiments are provided methods for the treatment of abnormal cell growth in a mammal comprising administering to a mammal an amount of one or more pharmaceutical compositions provided herein, in combination with an amount of an anti-tumor agent, which amounts are together effective in treating said abnormal cell growth. In some embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In some embodiments are provided one or more pharmaceutical compositions provided herein for use in the treatment of abnormal cell growth in a mammal. In a further aspect, are disclosed the uses of one or more pharmaceutical compositions described herein for the treatment of abnormal cell growth in a mammal.

In yet another aspect, are disclosed uses of one or more pharmaceutical compositions described herein for the preparation of a medicament for the treatment of abnormal cell growth.

In frequent embodiments of the methods and uses described herein, the abnormal cell growth is cancer. In some embodiments, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof.

In some embodiments, the cancer is selected from the group consisting of non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer.

In some embodiments, the methods described herein further comprise administering to the mammal an amount of an anti-cancer therapeutic agent or a palliative agent, which amounts are together effective in treating said abnormal cell growth. In some such embodiments, one or more anti-cancer therapeutic agent are selected from anti-tumor agents, anti-angiogenesis agents, signal transduction inhibitors and anti-proliferative agents, which amounts are together effective in treating said abnormal cell growth.

In other embodiments, the uses described herein comprise the use of one or more pharmaceutical compositions provided herein in combination with one or more substances selected from anti-tumor agents, anti-angiogenesis agents, signal transduction inhibitors and antiproliferative agents.

In some embodiments, the pharmaceutical compositions described herein are adapted for use in combination with one or more substances selected from anti-tumor agents, anti-angiogenesis agents, signal transduction inhibitors and anti-proliferative agents.

Each of the embodiments of the pharmaceutical compositions provided herein can be combined with one or more other embodiments of the pharmaceutical compositions described herein that is not inconsistent with the embodiment(s) with which it is combined.

In addition, each of the embodiments provided herein envisions within its scope that the pharmaceutical compositions described may comprise N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt of N-[5-(3,5-difluorobenzyl)-1H-indazol-3-yl]-4-(4-methyl-piperazin-1-yl)-2-(tetrahydro-2H-pyran-4-ylamino)-benzamide.

In some embodiments are provided methods for treating diseases caused by and/or associated with deregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, FLT3, JAK2, IGF-R, ALK, PI3K, weel kinase, Src, Abl, Akt, MAPK, ILK, MK-2, IKK-2, Cdc7, Nek, Cdk/cyclin kinase family, more particularly Aurora 2, IGF-1R and ALK activity, and ROS1 activity, and further more particularly ALK activity and/or ROS1 activity, which comprises administering to a mammal in need thereof an effective amount of one or more pharmaceutical compositions provided herein.

In some embodiments are provided methods to treat a disease caused by and/or associated with dysregulated protein kinase activity selected from the group consisting of cancer and cell proliferative disorders.

In some embodiments are provided methods to treat specific types of cancer comprising carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epithelioid hemangioendothelioma, astrocytoma, meningioma, angiosarcoma, epithelioid hemangiothelioma, keratocanthomas, thyroid follicular cancer, Kaposi's sarcoma, and pancreatic cancer.

In some embodiments are provided methods to treat specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, pancreatic cancer, neuroblastoma, and medulloblastoma.

In some embodiments are provided methods to treat ALK+ anaplastic large cell lymphomas (ALCL) and possibly other indications in which the ALK activity might play a role, like neuroblastoma, rhabdomyosarcoma, glioblastoma, inflammatory myofibroblastic tumor, and some kind of melanomas, breast carcinomas, Ewings sarcomas, retinoblastomas and non-small cell lung carcinomas (NSCLC).

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering one or more pharmaceutical compositions provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering one or more pharmaceutical compositions provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering one or more pharmaceutical compositions provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering one or more pharmaceutical compositions provided herein.

In some embodiments, methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject one or more pharmaceutical compositions provided herein.

In some embodiments are provided methods to treat, reduce the symptoms of, ameliorate the symptoms of, delay the onset of, or otherwise pharmaceutically address pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject one or more pharmaceutical compositions provided herein.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 activity in a cell extract from a pancreatic cancerous or precancerous cell population.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering one or more pharmaceutical compositions provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering one or more pharmaceutical compositions provided herein.

In some embodiments are provided methods to treat, reduce the symptoms of, ameliorate the symptoms of, delay the onset of, or otherwise pharmaceutically address pancreatic cancer in a subject, and possibly other indications in such subject in which a defect in the modulation of ROS1, TrkA, TrkB, or TrkC activity, or a combination thereof, activity, or upregulation, misregulation or deletion thereof might play a role by administering to the subject one or more of the pharmaceutical compositions provided herein.

In some embodiments are provided methods to treat, reduce the symptoms of, ameliorate the symptoms of, delay the onset of, or otherwise pharmaceutically address pancreatic cancer in a subject, which cancer is associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject one or more pharmaceutical compositions provided herein.

In some embodiments are provided methods to treat, reduce the symptoms of, ameliorate the symptoms of, delay the onset of, or otherwise pharmaceutically address a condition in a subject selected from non-small cell lung cancer, papillary thyroid cancer, neuroblastoma, pancreatic cancer and colorectal cancer and possibly other indications in which a defect in the modulation of ALK, ROS1, TrkA, TrkB, or TrkC activity, or a combination thereof, or upregulation, misregulation or deletion thereof might play a role by administering to the subject one or more of the pharmaceutical compositions provided herein.

In some embodiments are provided methods to treat, reduce the symptoms of, ameliorate the symptoms of, delay the onset of, or otherwise pharmaceutically address a condition in a subject selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering to the subject one or more of the pharmaceutical compositions provided herein.

In some embodiments are provided methods to treat, reduce the symptoms of, ameliorate the symptoms of, delay the onset of, or otherwise pharmaceutically address a condition in a subject selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an subject, and administering to the subject one or more pharmaceutical compositions provided herein.

In some embodiments are provided methods to treat, reduce the symptoms of, ameliorate the symptoms of, delay the onset of, or otherwise pharmaceutically address a condition in a subject selected from non-small cell lung cancer, papillary thyroid cancer, neuroblastoma, pancreatic cancer and colorectal cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous cell in an subject, and administering to the subject one or more of the pharmaceutical compositions provided herein.

In some embodiments are provided methods to treat cell proliferative disorders such as, but not restricted to, benign prostate hyperplasia, familial adenomatosis polyposis, neuro-fibromatosis, psoriasis, atherosclerosis and conditions involving vascular smooth muscle proliferation or neointimal formation such as restenosis following angioplasty or surgery, pulmonary fibrosis, arthritis, glomerulonephritis, retinopathies comprising diabetic and neonatal retinopathies and age related macular degeneration, graft vessel disease, such as can occur following vessel or organ transplantation, acromegaly and disorders secondary to acromegaly as well as other hypertrophic conditions in which IGF/IGF-1R signaling is implicated, such as fibrotic lung disease, pathologies related to chronic or acute oxidative stress or hyperoxia induced tissue damage, and metabolic disorders in which elevated IGF levels or IGF-1R activity are implicated, such as obesity.

In some embodiments are provided methods of affecting tumor angiogenesis and metastasis inhibition.

In some embodiments, the methods provided herein further comprise subjecting the mammal in need thereof to a radiation therapy or chemotherapy regimen in combination with at least one cytostatic or cytotoxic agent. In some embodiments, the methods provided herein further comprise inhibiting the activity ALK protein which comprises contacting the said protein with an effective amount of one or more pharmaceutical compositions provided herein.

In some embodiments, the methods provided herein for inhibiting at least one of ALK, ROS1, TrkA, TrkB, or TrkC kinase activity, or a combination thereof, in a cell, comprising contacting said cell with an effective amount of one or more pharmaceutical compositions provided herein.

In some embodiments are provided pharmaceutical compositions comprising one or more pharmaceutical compositions provided herein and a pharmaceutically acceptable excipient, carrier or diluent.

Some embodiments provide methods of inhibiting ALK, ROS1, TrkA, TrkB, or TrkC activity, or a combination thereof, in a subject, comprising administering to said subject an effective amount of one or more pharmaceutical compositions provided herein.

Some embodiments provide methods of treating cancer in a subject in need thereof, the method comprising inhibiting ALK, ROS1, TrkA, TrkB, or TrkC activity, or a combination thereof, in said subject, by administering to said subject an effective amount of one or more pharmaceutical compositions provided herein.

Some embodiments provide methods of treating non-small cell lung cancer, papillary thyroid cancer, neuroblastoma, pancreatic cancer or colorectal cancer in a subject, comprising administering to said subject an effective amount of one or more pharmaceutical compositions provided herein.

Some embodiments provide methods of treating tumors in a subject, said methods comprising administering to the subject an effective amount of one or more pharmaceutical compositions provided herein.

Some embodiments provide methods wherein the tumors are caused by the presence of non-small cell lung cancer, papillary thyroid cancer, neuroblastoma, pancreatic cancer or colorectal cancer in the subject. Some embodiments provide methods wherein one or more of the cells comprising the tumors in the subject test positive for the presence of a gene that expresses at least one of ALK, ROS1, TrkA, TrkB, or TrkC kinase or one or more of the cells comprising the tumors in said subject demonstrates at least one of ALK, ROS1, TrkA, TrkB, or TrkC kinase activity.

Some embodiments provide methods wherein one or more of the cells comprising the tumors in the subject test positive for at least one gene rearrangement comprising the gene, or a fragment thereof, that expresses at least one of ALK, ROS1, TrkA, TrkB, or TrkC kinase. Some embodiments provide such methods wherein the cells test positive for at least one of ROS1, TrkA, TrkB, or TrkC kinases. Some embodiments provide methods wherein the cells test positive for ROS1 kinase. Some embodiments provide methods wherein the cells test positive for at least one of TrkA, TrkB and TrkC kinase. Some embodiments provide methods wherein the cells test positive for TrkA kinase. Some embodiments provide methods wherein the cells test positive for TrkB kinase. Some embodiments provide such methods wherein the cells test positive for TrkC kinase.

Some embodiments provide methods of treating cancer in a subject, the method comprising: (1) testing one or more cells comprising the tumors in the subject for the presence of at least one of ALK, ROS1, TrkA, TrkB, or TrkC kinase; and (2) administering to the subject an effective amount of one or more pharmaceutical compositions provided herein.

Some embodiments provide methods of treating cancer in a subject, the method comprising: (1) testing one or more cells comprising the tumors in the subject for the presence of at least one molecular alteration in ALK, ROS1, TrkA, TrkB, or TrkC kinase; and (2) administering to the subject an effective amount of one or more pharmaceutical compositions provided herein.

Some embodiments provide methods of treating cancer in a subject, wherein one or more cancerous cells in said subject express at least one of ROS1, TrkA, TrkB, or TrkC kinase, the method comprising administering to the subject an effective amount of one or more pharmaceutical compositions provided herein.

Some embodiments provide a method for treating a subject having cancer, wherein tumors from said subject are ROS1, TrkA, TrkB, or TrkC positive, a combination thereof, the method comprising administering to the subject an effective amount of one or more pharmaceutical compositions provided herein.

Some embodiments provide a method of treating a cancer subject, comprising (a) acquiring knowledge of the presence of at least one genetic alteration in at least one target gene in the cancer subject, wherein the at least one target gene is selected from ALK1, BDNF, NGF, NGFR, NTF3, NTF4, ROS1, SORT1, NTRK1, NTRK2, and NTRK3; (b) selecting one or more pharmaceutical compositions provided herein as a treatment for the cancer subject, based on the recognition that said pharmaceutical composition is effective in treating cancer subjects having said at least one genetic alteration in said at least one target gene; and (c) administering a therapeutically effective amount of one or more of said pharmaceutical compositions to said cancer subject.

Some embodiments provide a method of treating a cancer subject, comprising administering to said cancer subject a therapeutically effective amount of one or more pharmaceutical compositions provided herein, wherein prior to said administration of said one or more pharmaceutical compositions said cancer subject is known to possess at least one genetic alteration in at least one target gene selected from ALK1, BDNF, NGF, NGFR, NTF3, NTF4, ROS1, SORT1, NTRK1, NTRK2, and NTRK3.

Some embodiments provide a method of treating a cancer subject, wherein prior to said treatment said subject is known to possess at least one genetic alteration in at least one target gene, comprising administering to said cancer subject a therapeutically effective amount of one or more pharmaceutical compositions provided herein and wherein said at least one target gene is selected from ALK1, BDNF, NGF, NGFR, NTF3, NTF4, ROS1, SORT1, NTRK1, NTRK2, and NTRK3.

Some embodiments provide any of the methods described herein wherein the subject or subject is suffering from cancer and the cancer is selected from at least one of non-small cell lung cancer, papillary thyroid cancer, neuroblastoma, pancreatic cancer and colorectal cancer.

In one aspect, provided herein are methods for treating cancer in a subject, comprising (a) acquiring knowledge of the presence of one or more molecular alterations in a biological sample from the cancer subject, wherein the one or more molecular alterations is detected by an assay comprising one or more antibodies that bind to one or more of ALK, ROS1, TrkA, TrkB, and TrkC biomarkers; (b) selecting a chemotherapeutic agent as a treatment for the cancer subject wherein the assay detects the presence of one or more of molecular alterations, and wherein the selected chemotherapeutic agent is one or more of the pharmaceutical compositions provided herein, or a pharmaceutically acceptable salt thereof; and (c) administering a therapeutically effective amount of the one or more selected chemotherapeutic agents to the cancer subject.

In another aspect, provided herein are methods for selecting a cancer subject who is predicted to respond to the administration of a therapeutic regimen, comprising (a) acquiring knowledge of the presence of one or more molecular alterations in a biological sample from the cancer subject, wherein the one or more molecular alterations is detected by an assay comprising one or more antibodies that bind to one or more of ALK, ROS1, TrkA, TrkB, and TrkC biomarkers; and (b) selecting the subject as predicted to respond to the administration of a therapeutic regimen if the one or more molecular alterations is detected in one or more of the biomarkers, or selecting the subject as predicted to not respond to the administration of a therapeutic regimen if the one or more molecular alterations is not detected in the biomarkers. In the methods according to this aspect of the disclosure, the therapeutic regiment includes administering to the selected subject a therapeutically effective amount of one or more of the pharmaceutical compositions provided herein.

It will be appreciated that the actual dosages N-[5-(3,5-difluorobenzyl)-1H-indazol-3-yl]-4-(4-methyl-piperazin-1-yl)-2-(tetrahydro-pyran-4-ylamino)-benzamide will vary according the particular composition formulated, the mode of administration, and the particular site, subject or subject, and disease being treated. Those skilled in the art using conventional dosage-determination tests in view of the experimental data for N-[5-(3,5-difluorobenzyl)-1H-indazol-3-yl]-4-(4-methyl-piperazin-1-yl)-2-(tetrahydro-pyran-4-ylamino)-benzamide may ascertain optimal dosages for a given set of conditions. For oral administration, an exemplary daily dose generally employed will be from about 0.001 to about 1000 mg/kg, from about 0.1 mg to about 1000 mg of body weight, with courses of treatment repeated at appropriate intervals.

This amount will vary depending upon a variety of factors, comprising but not limited to the characteristics of the pharmaceutical compositions and formulations provided herein (comprising activity, pharmacokinetics, pharmacodynamics, and bioavailability thereof), the physiological condition of the subject treated (comprising age, sex, disease type and stage, general physical condition, responsiveness to a given dosage, and type of medication) or cells, the nature of the pharmaceutically acceptable carrier mg/kg or carriers in the formulation, and the route of administration. Further, an effective or therapeutically effective amount may vary depending on whether the one or more pharmaceutical compositions provided herein is administered alone or in combination with other drug(s), other therapy/therapies or other therapeutic method(s) or modality/modalities. One skilled in the clinical and pharmacological arts will be able to determine an effective amount or therapeutically effective amount through routine experimentation, namely by monitoring a cell's or subject's response to administration of the one or more pharmaceutical compositions and formulations provided herein and adjusting the dosage accordingly.

In some embodiments, a dose of N-[5-(3,5-difluorobenzyl)-1H-indazol-3-yl]-4-(4-methyl-piperazin-1-yl)-2-(tetrahydro-pyran-4-ylamino)-benzamide may range from about 0.1 mg/kg to about 100 mg/kg or more, depending on the factors mentioned above. In other alternatives, the dosage may range from about 0.1 mg/kg to about 100 mg/kg; or about 1 mg/kg to about 100 mg/kg; or about 5 mg/kg up to about 100 mg/kg. For topical applications such as, for example, treatment of various hair conditions, according to some alternatives provided herein, suitable dosage may range from about 1 mg/kg to about 10 g/kg; or about 10 mg/kg to about 1 g/kg; or about 50 mg/kg up to about 10 g/kg. Additional guidance with regard to this aspect can be found in, for example, Remington: The Science and Practice of Pharmacy, 21st Edition, Univ. of Sciences in Philadelphia (USIP), Lippincott Williams & Wilkins, Philadelphia, Pa., 2005.

Some embodiments include any of the methods described herein, wherein any of the pharmaceutical compositions provided herein that comprise N-[5-(3,5-difluorobenzyl)-1H-indazol-3-yl]-4-(4-methyl-piperazin-1-yl)-2-(tetrahydro-2H-pyran-4-ylamino)-benzamide are administered to a subject in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives ranges from about 200 mg/m$^2$ to about 1600 mg/m$^2$, or from about 200 mg/m$^2$ to about 1200 mg/m$^2$, or from about 200 mg/m$^2$ to about 1000 mg/m$^2$, or from about 400 mg/m$^2$ to about 1200 mg/m$^2$, or from about 400 mg/m$^2$ to about 1000 mg/m$^2$, or from about 800 mg/m$^2$ to about 1000 mg/m$^2$, or from about 800 mg/m$^2$ to about 1200 mg/m$^2$, or from about 800 mg/m$^2$ to about 1200 mg/m$^2$, or from about 800 mg/m$^2$ to about 1600 mg/m$^2$.

Some embodiments include any of the methods described herein, wherein any of the pharmaceutical compositions provided herein that comprise N-[5-(3,5-difluorobenzyl)-1H-indazol-3-yl]-4-(4-methyl-piperazin-1-yl)-2-(tetrahydro-2H-pyran-4-ylamino)-benzamide are administered to a subject in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 200 mg/m$^2$, about 300 mg/m$^2$, about 400 mg/m$^2$, about 500 mg/m$^2$, about 600 mg/m$^2$, about 700 mg/m$^2$, about 800 mg/m$^2$, about 900 mg/m$^2$, about 1000 mg/m$^2$, about 1100 mg/m$^2$, about 1200 mg/m$^2$, about 1300 mg/m$^2$, about 1400 mg/m$^2$, about 1500 mg/m$^2$, about 1600 mg/m$^2$, about 1700 mg/m$^2$, about 1800 mg/m$^2$, about 1900 mg/m$^2$, or about 2000 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 200 mg/m$^2$, about 300 mg/m$^2$, about 400 mg/m$^2$, about 500 mg/m$^2$, about 600 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 200 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 300 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 400 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 500 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 600 mg/m$^2$.

Some embodiments include any of the methods described herein, wherein any of the pharmaceutical compositions provided herein that comprise N-[5-(3,5-difluorobenzyl)-1H-indazol-3-yl]-4-(4-methyl-piperazin-1-yl)-2-(tetrahydro-2H-pyran-4-ylamino)-benzamide are administered to a subject in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 200 mg, about 300 mg, about 400 mg, about 500 mg, about 600 mg, about 700 mg, about 800 mg, about 900 mg, or about 1000 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 200 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 300 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 400 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 500 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 600 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 700 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 800 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 900 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives is about 1000 mg.

Some embodiments include any of the methods described herein, wherein any of the pharmaceutical compositions provided herein that comprise N-[5-(3,5-difluorobenzyl)-1H-indazol-3-yl]-4-(4-methyl-piperazin-1-yl)-2-(tetrahydro-2H-pyran-4-ylamino)-benzamide are administered to a subject once per day in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives per day is about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 200 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 300 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 400 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 500 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 600 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 700 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 800 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 900 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide the subject receives once per day is about 1000 mg.

Those of ordinary skill in the art will understand that with respect to pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide provided herein the particular pharmaceutical composition, the dosage, and the number of doses given per day to a mammal requiring such treatment, are all choices within the knowledge of one of ordinary skill in the art and can be determined without undue experimentation.

Accordingly, while certain dose and administration regimens are exemplified herein, these examples in no way limit the dose and administration regimen that may be provided to a subject in practicing the presently disclosed methods.

It is to be noted that dosage values may vary with the type and severity of the condition to be alleviated, and may include single or multiple doses. It is to be further understood that for any particular subject, specific dosage regimens should be adjusted over time according to the subject need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. The embodiments provided herein are intended to encompass intra-subject dose-escalation as determined by the skilled artisan. Determining appropriate dosages and regimens for administration of the chemotherapeutic agent are well-known in the relevant art and would be understood to be encompassed by the skilled artisan once provided the teachings provided herein.

Implementations of the methods of the present disclosure can include one or more of the following features. In some embodiments, the selected chemotherapeutic agent one or more of the pharmaceutical compositions provided herein. In some embodiments, the assay includes one or more antibodies that bind to at least two of ALK, ROS1, TrkA, TrkB and TrkC biomarkers. In some embodiments, the one or more molecular alterations detected in the biological sample involve at least two, at least three, or at least four of the biomarkers. In some embodiments, the knowledge of the presence of the one or more molecular alterations in the biological sample is acquired from an assay that includes contacting the biological sample with one or more antibodies or fragments thereof specific for the biomarkers. In some embodiments, the specific antibodies are monoclonal antibodies. In some embodiments, the specific antibodies include at least one of D5F3®, D4D5®, C17F1®, and combinations thereof. In some embodiments, the biological sample is contacted with one or more of the specific antibodies simultaneously. In some embodiments, the biological sample is sequentially contacted with the specific antibodies. In some embodiments, the one or more molecular alterations results in elevated expression of one or more of the ALK, ROS1, TrkA, TrkB, and TrkC biomarkers. In some embodiments, the knowledge of the one or more molecular alterations is acquired from an assay wherein determining whether the expression of one or more biomarker is elevated includes: (a) determining the expression level of the one or more biomarkers in the biological sample; and (b) comparing the determined expression level to a reference expression level. In some embodiments, the knowledge of the one or more molecular alterations is acquired from an antibody-based assay. In some embodiments, the antibody-based assay is selected from the group consisting of ELISA, immunohistochemistry, western blotting, mass spectrometry, flow cytometry, protein-microarray, immunofluorescence, and a multiplex detection assay. In some embodiments, the antibody-based assay includes an immunohistochemistry analysis.

In some embodiments, implementations of the methods provided herein further include acquiring knowledge of a genetic alteration in the cancer of the subject from a second analytical assay prior to the administering step, wherein the second analytical assay is selected from the group consisting of capillary electrophoresis, nucleic acid sequencing, polypeptide sequencing, restriction digestion, nucleic acid amplification-based assays, nucleic acid hybridization assay, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), and a kinase activity assay. In some embodiments, the cancer is cancer is selected from the group consisting of anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, and papillary thyroid cancer. In some embodiments, the knowledge of the one or more molecular alterations is obtained from an assay performed simultaneously on a plurality of biological samples. In some embodiments, the plurality of biological samples includes at least 6, 12, 24, 48, 96, 200, 384, 400, 500, 1000, 1500, or 3000 samples. In some embodiments, the one or more molecular alterations is selected from a genetic mutation, a gene amplification, a gene rearrangement, a single-nucleotide variation (SNV), a deletion, an insertion, an InDel mutation, a single nucleotide point mutation (SNP), an epigenetic alteration, a splicing variant, an RNA/protein overexpression, an aberrant RNA/protein expression, and any combination thereof. In some embodiments, the one or more molecular alterations include an insertion of a heterologous nucleic acid sequence within a coding sequence of a biomarker gene. In some embodiments, the insertion forms a chimeric nucleic acid sequence that encodes a fusion peptide. In some embodiments, the acquiring knowledge of the one or more molecular alterations further includes determining a nucleic acid sequence and/or an amino acid sequence comprising the one or more molecular alterations.

Some embodiments provide a pharmaceutical composition comprising one or more pharmaceutical compositions provided herein in combination with one or more chemotherapeutic agents or radiotherapy, such as radiotherapy as commonly administered to treat, ameliorate the symptoms of, or prevent or delay the onset of cancer. Such agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

Some embodiments provide a product or kit comprising one or more pharmaceutical compositions provided herein and one or more chemotherapeutic agents, as a combined preparation for simultaneous, separate or sequential use in anticancer therapy.

Some embodiments provide one or more pharmaceutical compositions as provided herein for use as a medicament.

Some embodiments provide the use of one or more pharmaceutical compositions as provided herein in the manufacture of a medicament with antitumor activity.

Some embodiments include any of the methods described herein, wherein said cancer is selected from non-small cell lung cancer, papillary thyroid cancer, neuroblastoma, pancreatic cancer and colorectal cancer. Some embodiments are any of the methods described herein wherein said cancer is non-small cell lung cancer. Some embodiments include any of the methods described herein, wherein said cancer is said cancer is papillary thyroid cancer. Some embodiments include any of the methods described herein, wherein said cancer is wherein said cancer is neuroblastoma. Some embodiments include any of the methods described herein, wherein said cancer is wherein said cancer is pancreatic cancer. Some embodiments include any of the methods described herein, wherein said cancer is wherein said cancer is colorectal cancer.

The pharmaceutically acceptable carrier may comprise a conventional pharmaceutical carrier or excipient. Suitable pharmaceutical carriers include inert diluents or fillers, glidants, lubricants, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. In some embodiments, the excipient comprises pregelatinized starch. In some embodiments, the pharmaceutical compositions comprise a glidant. In some embodiments, the pharmaceutical compositions comprise colloidal silicon dioxide. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols.

To treat or prevent diseases or conditions mediated by ALK, ROS1, TrkA, TrkB, or TrkC, or a combination thereof, a pharmaceutical composition provided herein is administered by combining a therapeutically effective amount of N-[5-(3,5-difluorobenzyl)-1H-indazol-3-yl]-4-(4-methyl-piperazin-1-yl)-2-(tetrahydro-pyran-4-ylamino)-benzamide and at least one acidulant. Optionally, such pharmaceutical compositions may comprise one or more pharmaceutically suitable carriers, which may be selected, for example, from diluents, excipients and auxiliaries that facilitate processing of N-[5-(3,5-difluorobenzyl)-1H-indazol-3-yl]-4-(4-methyl-piperazin-1-yl)-2-(tetrahydro-pyran-4-ylamino)-benzamide into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, N-[5-(3,5-difluorobenzyl)-1H-indazol-3-yl]-4-(4-methyl-piperazin-1-yl)-2-(tetrahydro-pyran-4-ylamino)-benzamide may be dissolved in an aqueous solution of an organic or inorganic acid, such as a 0.3 M solution of succinic acid or citric acid. If a soluble salt form is not available, N-[5-(3,5-difluorobenzyl)-1H-indazol-3-yl]-4-(4-methyl-piperazin-1-yl)-2-(tetrahydro-pyran-4-ylamino)-benzamide may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, N-[5-(3,5-difluorobenzyl)-1H-indazol-3-yl]-4-(4-methyl-piperazin-1-yl)-2-(tetrahydro-pyran-4-ylamino)-benzamide is dissolved in DMSO and diluted with water. The pharmaceutical composition may also be in the form of a solution of a salt form of N-[5-(3,5-difluorobenzyl)-1H-indazol-3-yl]-4-(4-methyl-piperazin-1-yl)-2-(tetrahydro-pyran-4-ylamino)-benzamide in an appropriate aqueous vehicle such as water or isotonic saline or dextrose solution.

Proper formulation is dependent upon the route of administration selected. For injection, N-[5-(3,5-difluorobenzyl)-1H-indazol-3-yl]-4-(4-methyl-piperazin-1-yl)-2-(tetrahydro-pyran-4-ylamino)-benzamide may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, N-[5-(3,5-difluorobenzyl)-1H-indazol-3-yl]-4-(4-methyl-piperazin-1-yl)-2-(tetrahydro-pyran-4-ylamino)-benzamide may be formulated by combining it with pharmaceutically acceptable carriers known in the art. Such carriers enable N-[5-(3,5-difluorobenzyl)-1H-indazol-3-yl]-4-(4-methyl-piperazin-1-yl)-2-(tetrahydro-pyran-4-ylamino)-benzamide to be formulated as tablets, pills, dragees, capsules, powders, granules, liquids, gels, syrups, slurries, suspensions and the like, for oral ingestion by a subject to be treated. Pharmaceutical preparations for oral use can be obtained using a solid excipient in admixture with N-[5-(3,5-difluorobenzyl)-1H-indazol-3-yl]-4-(4-methyl-piperazin-1-yl)-2-(tetrahydro-pyran-4-ylamino)-benzamide, optionally grinding the resulting mixture, and processing the mixture of granules after adding suitable auxiliaries, if desired, to obtain tablets or dragee cores. Suitable excipients include: fillers such as sugars, comprising isomalt, lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, microcrystalline cellulose or polyvinylpyrrolidone (PVP). In some embodiments, the filler is mannitol, isomalt, hypromellose (hydroxypropylmethylcellulose), or microcrystalline cellulose. In some embodiments, the filler is mannitol. In some embodiments, the filler is isomalt. In some embodiments, the filler is microcrystalline cellulose. In some embodiments, the filler is lactose. In some embodiments, the filler is anhydrous lactose. If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings.

Pharmaceutical preparations that can be used orally include push-fit capsules made of gelatin, as well as soft, sealed capsules made of gelatin and a plasticizer, such as glycerol or sorbitol. The push-fit capsules can contain N-[5-(3,5-difluorobenzyl)-1H-indazol-3-yl]-4-(4-methyl-piperazin-1-yl)-2-(tetrahydro-pyran-4-ylamino)-benzamide in admixture with fillers such as lactose, binders such as starches, and/or lubricants such as talc or magnesium stearate, and, optionally, stabilizers. In soft capsules, N-[5-(3,5-difluorobenzyl)-1H-indazol-3-yl]-4-(4-methyl-piperazin-1-yl)-2-(tetrahydro-pyran-4-ylamino)-benzamide may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

The pharmaceutical compositions provided herein are useful for the treatment of cancers comprising but not limited to cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues comprising connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of cancer when used herein in connection with pharmaceutical compositions provided herein include cancer selected from lung cancer (NSCLC and SCLC), cancer of the head or neck, ovarian cancer, colon cancer, rectal cancer, prostate cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

In some embodiments, the pharmaceutical compositions provided herein are useful for the treatment of cancers, comprising Spitz melanoma, perineural invasion, pulmonary large cell neuroendocrine carcinoma, uterine carcinoma, juvenile breast cancer, nasopharyngeal carcinoma, adenoid cystic cancer, meduallary thyroid cancer, salivary cancer, congenital infantile fibrosarcoma, mesoblastic nephroma, esophageal cancer (squamous), diffuse large B-cell lymphoma, papillary thyroid cancer, and mammary analogue secretory carcinoma.

In some embodiments are provided methods for treating diseases caused by and/or associated with deregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, FLT3, JAK2, IGF-R, ALK, PI3K, weel kinase, Src, Abl, Akt, MAPK, ILK, MK-2, IKK-2, Cdc7, Nek, Cdk/cyclin kinase family, more particularly Aurora 2, IGF-1R and ALK activity, and ROS1 activity, and further more particularly ALK activity and/or ROS1 activity, which comprises administering to a mammal in need thereof an effective amount of a pharmaceutical composition provided herein.

In some embodiments disclosed herein are directed to treat a disease caused by and/or associated with dysregulated protein kinase activity selected from the group consisting of cancer and cell proliferative disorders.

In some embodiments are provided methods to treat specific types of cancer comprising carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epithelioid hemangioendothelioma, astrocytoma, meningioma, angiosarcoma, epithelioid hemangiothelioma, keratocanthomas, thyroid follicular cancer, Kaposi's sarcoma, and pancreatic cancer.

Some embodiments disclosed herein are directed to treating specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, pancreatic cancer, and medulloblastoma.

In some embodiments are provided methods of treating ALK+ Anaplastic Large Cell Lymphomas (ALCL) and possibly other indications in which the ALK activity might play a role, like Neuroblastoma, Rhabdomyosarcoma, Glioblastoma, Inflammatory Myofibroblastic Tumor, and some kind of Melanomas, Breast Carcinomas, Ewings sarcomas, Retinoblastomas and Non-Small Cell Lung Carcinomas (NSCLC).

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a by administering a pharmaceutical compositions as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein.

In some embodiments are provided methods to treat, reduce the symptoms of, ameliorate the symptoms of, delay the onset of, or otherwise pharmaceutically address pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject a pharmaceutical composition as provided herein.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 transcript accumulation in an RNA population from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC activity in a cell extract from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC transcript accumulation in an RNA population from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein.

In some embodiments are provided methods to treat, reduce the symptoms of, ameliorate the symptoms of, delay the onset of, or otherwise pharmaceutically address pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject a pharmaceutical composition as provided herein.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 transcript accumulation in an RNA population from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC activity in a cell extract from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC transcript accumulation in an RNA population from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ALK, ROS1, TrkA, TrkB, or TrkC activity, or a combination thereof, or upregulation, misregulation or deletion thereof might play a role by administering pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an subject, and administering to the subject a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an subject, and administering to the subject a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an subject, and administering to the subject a pharmaceutical composition as provided herein.

In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous cell in an subject, and administering to the subject a pharmaceutical composition as provided herein.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an subject comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an subject comprises assaying for ROS1 transcript accumulation in an RNA population from a cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an subject comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an subject comprises assaying for ALK, ROS1, TrkA, TrkB, or TrkC activity in a cell extract from a cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an subject comprises assaying for ALK, ROS1, TrkA, TrkB, or TrkC transcript accumulation in an RNA population from a cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an subject comprises determining the nucleic acid sequence such as the genomic deoxyribonucleic acid sequence in a cell or cells or a cell population comprising a cell or cells from a cancerous or precancerous cell populations.

In some embodiments are provided methods for inhibiting at least one of ALK, ROS1, TrkA, TrkB, or TrkC kinase activity, or a combination thereof, in a cell, comprising contacting said cell with an effective amount of N-[5-(3,5-difluorobenzyl)-1H-indazol-3-yl]-4-(4-methyl-piperazin-1-yl)-2-(tetrahydro-2H-pyran-4-ylamino)-benzamide. Some embodiments provide methods of inhibiting at least one of ALK, ROS1, TrkA, TrkB, or TrkC kinase activity, or a combination thereof, in a cell, by contacting the cell with an effective amount of N-[5-(3,5-difluorobenzyl)-1H-indazol-3-yl]-4-(4-methyl-piperazin-1-yl)-2-(tetrahydro-2H-pyran-4-ylamino)-benzamide. Some embodiments provide methods of inhibiting at least one of ALK, ROS1, TrkA, TrkB, or TrkC kinase activity, or a combination thereof, in a cell, comprising contacting said cell with an effective amount of a compound which is N-[5-(3,5-difluorobenzyl)-1H-indazol-3-yl]-4-(4-methyl-piperazin-1-yl)-2-(tetrahydro-2H-pyran-4-ylamino)-benzamide. In some embodiments, the N-[5-(3,5-difluorobenzyl)-1H-indazol-3-yl]-4-(4-methyl-piperazin-1-yl)-2-(tetrahydro-2H-pyran-4-ylamino)-benzamide is delivered to the cell in the form of a pharmaceutical composition as provided herein.

Some embodiments provide methods of inhibiting ALK, ROS1, TrkA, TrkB, or TrkC activity, or a combination thereof, in a subject, comprising administering to said subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide methods of treating cancer in a subject in need thereof, the method comprising inhibiting ALK, ROS1, TrkA, TrkB, or TrkC activity, or a combination thereof, in said subject, by administering to said subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide methods of treating non-small cell lung cancer, papillary thyroid cancer, neuroblastoma, pancreatic cancer or colorectal cancer in a subject, comprising administering to said subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide methods of treating tumors in a subject, said methods comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide methods wherein the tumors are caused by the presence of non-small cell lung cancer, papillary thyroid cancer, neuroblastoma, pancreatic cancer or colorectal cancer in the subject. Some embodiments provide methods wherein one or more of the cells comprising the tumors in the subject test positive for the presence of a gene that expresses at least one of ALK, ROS1, TrkA, TrkB, or TrkC kinase or one or more of the cells comprising the tumors in said subject demonstrates at least one of ALK, ROS1, TrkA, TrkB, or TrkC kinase activity.

Some embodiments provide methods wherein one or more of the cells comprising the tumors in the subject test positive for at least one gene rearrangement comprising the gene, or a fragment thereof, that expresses at least one of ALK, ROS1, TrkA, TrkB, or TrkC kinase. Some embodiments provide such methods wherein the cells test positive for at least one of ROS1, TrkA, TrkB, or TrkC kinases. Some embodiments provide methods wherein the cells test positive for ROS1 kinase. Some embodiments provide methods wherein the cells test positive for at least one of TrkA, TrkB and TrkC kinase. Some embodiments provide methods wherein the cells test positive for TrkA kinase. Some embodiments provide methods wherein the cells test positive for TrkB kinase. Some embodiments provide such methods wherein the cells test positive for TrkC kinase.

Some embodiments provide methods of treating cancer in a subject, the method comprising: (1) testing one or more cells comprising the tumors in the subject for the presence of at least one of ALK, ROS1, TrkA, TrkB, or TrkC kinase; and (2) administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide if said one or more cells tests positive for at least one of ALK, ROS1, TrkA, TrkB, or TrkC kinase.

Some embodiments provide methods of treating cancer in a subject, the method comprising: (1) testing one or more cells comprising the tumors in the subject for the presence of at least one of ROS1, TrkA, TrkB, or TrkC kinase; and (2) administering to the subject a pharmaceutical formulation as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide if said one or more cells tests positive for at least one of ROS1, TrkA, TrkB, or TrkC kinase.

Some embodiments provide methods of treating cancer in a subject, wherein one or more cancerous cells in said subject express at least one of ROS1, TrkA, TrkB, or TrkC kinase, the method comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, Some embodiments provide methods of treating cancer in a subject, wherein one or more cancerous cells in said subject express at least one of ROS1, TrkA, TrkB, or TrkC kinase, the method comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide a method for treating a subject having cancer, wherein tumors from said subject are ALK, ROS1, TrkA, TrkB, or TrkC positive, or a combination thereof, the method comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide a method for treating a subject having ALK, ROS1, TrkA, TrkB, or TrkC positive cancer, or a combination thereof, the method comprising administering to the subject a pharmaceutical formulation as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide a method of treating a cancer subject, comprising (a) acquiring knowledge of the presence of at least one genetic alteration in at least one target gene in the cancer subject, wherein the at least one target gene is selected from ALK1, BDNF, NGF, NGFR, NTF3, NTF4, ROS1, SORT1, NTRK1, NTRK2, and NTRK3; and (b) administering a pharmaceutical composition as provided herein to said cancer subject, said pharmaceutical composition comprising a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide a method of treating a cancer subject, comprising administering to said cancer subject a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, wherein prior to said administration of said pharmaceutical composition, said cancer subject is known to possess at least one genetic alteration in at least one target gene selected from ALK1, BDNF, NGF, NGFR, NTF3, NTF4, ROS1, SORT1, NTRK1, NTRK2, and NTRK3.

Some embodiments provide a method of treating cancer in a subject, comprising administering to said cancer subject known to possess at least one genetic alteration in at least one target gene selected from ALK1, BDNF, NGF, NGFR, NTF3, NTF4, ROS1, SORT1, NTRK1, NTRK2, and NTRK3 a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide a method of treating a cancer subject, wherein said cancer subject is known to possess at least one genetic alteration in at least one target gene, comprising administering to said cancer subject a pharmaceutical compositions comprising a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, and wherein said target gene is selected from ALK1, BDNF, NGF, NGFR, NTF3, NTF4, ROS1, SORT1, NTRK1, NTRK2, and NTRK3.

Some embodiments provide a method of treating a cancer subject, wherein prior to said treatment said subject is known to possess at least one genetic alteration in at least one target gene, comprising administering to said cancer subject a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, and wherein said target gene is selected from ALK1, BDNF, NGF, NGFR, NTF3, NTF4, ROS1, SORT1, NTRK1, NTRK2, and NTRK3.

Some embodiments provide a method of treating a cancer subject, comprising administering to said cancer subject a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, and wherein prior to said pharmaceutical composition being administered to said subject, said subject is known to possess at least one genetic alteration in at least one target gene selected from ALK1, BDNF, NGF, NGFR, NTF3, NTF4, ROS1, SORT1, NTRK1, NTRK2, and NTRK3.

Some embodiments provide a method for treating a cancer subject, comprising (a) acquiring knowledge of the presence of at least one genetic alteration in at least one target gene selected from ALK1, BDNF, NGF, NGFR, NTF3, NTF4, ROS1, SORT1, NTRK1, NTRK2, and NTRK3; and (b) administering to said subject a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide.

Some embodiments provide any of the methods described herein wherein the subject or subject is suffering from cancer and the cancer is selected from at least one of non-small cell lung cancer, papillary thyroid cancer, neuroblastoma, pancreatic cancer and colorectal cancer. Some embodiments provide any of the methods described herein wherein the subject or subject is suffering from non-small cell lung cancer. Some embodiments provide any of the methods described herein wherein the subject or subject is suffering from papillary thyroid cancer. Some embodiments provide any of the methods described herein wherein the subject or subject is suffering from neuroblastoma. Some embodiments provide any of the methods described herein wherein the subject or subject is suffering from pancreatic cancer. Some embodiments provide any of the methods described herein wherein the subject or subject is suffering from colorectal cancer.

In some embodiments, the pharmaceutical compositions provided herein may be used in combination with one or more additional anti-cancer agents which are described below. When a combination therapy is used, the one or more additional anti-cancer agents may be administered sequentially or simultaneously with the pharmaceutical compositions provided herein. In some embodiments, the additional anti-cancer agent is administered to a mammal (e.g., a human) prior to administration of the pharmaceutical compositions provided herein. In some embodiments, the additional anti-cancer agent is administered to the mammal after administration of the pharmaceutical compositions provided herein. In some embodiments, the additional anti-cancer agent is administered to the mammal (e.g., a human) simultaneously with the administration of pharmaceutical compositions provided herein.

Some embodiments also relate to pharmaceutical compositions for the treatment of abnormal cell growth in a mammal, comprising a human, which comprises an amount of one or more pharmaceutical compositions provided herein comprising hydrates, solvates and polymorphs of N-[5-(3,5-difluorobenzyl)-1H-indazol-3-yl]-4-(4-methyl-piperazin-1-yl)-2-(tetrahydro-pyran-4-ylamino)-benzamide in combination with one or more (preferably one to three) anti-cancer agents selected from the group consisting of anti-angiogenesis agents and signal transduction inhibitors and a pharmaceutically acceptable carrier, wherein the amounts of N-[5-(3,5-difluorobenzyl)-1H-indazol-3-yl]-4-(4-methyl-piperazin-1-yl)-2-(tetrahydro-pyran-4-ylamino)-benzamide and the combination anti-cancer agents when taken as a whole is therapeutically effective for treating said abnormal cell growth.

In some embodiments, the anti-cancer agent used in conjunction with the pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKC-beta inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent®), bevacizumab (Avastin®), axitinib (AG 13736), SU 14813 (Pfizer), and AG 13958 (Pfizer).

Additional anti-angiogenesis agents include vatalanib (CGP 79787), Sorafenib (Nexavar®), pegaptanib octasodium (Macugen®), vandetanib (Zactima®), PF-0337210 (Pfizer), SU 14843 (Pfizer), AZD 2171 (AstraZeneca), ranibizumab (Lucentis®), Neovastat® (AE 941), tetrathiomolybdata (Coprexa®), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex®) and UCN 01 (Kyowa Hakko).

Other examples of anti-angiogenesis agents which can be used in conjunction with one or more pharmaceutical compositions described herein include celecoxib (Celebrex®), parecoxib (Dynastat®), deracoxib (SC 59046), lumiracoxib (Preige®), valdecoxib (Bextra®), rofecoxib (Vioxx®), iguratimod (Careram®), IP 751 (Invedus), SC-58125 (Pharmacia) and etoricoxib (Arcoxia®).

Other anti-angiogenesis agents include exisulind (Aptosyn®), salsalate (Amigesic®), diflunisal (Dolobid®), ibuprofen (Motrin®), ketoprofen (Orudis®) nabumetone (Relafen®), piroxicam (Feldene®), naproxen (Aleve®, Naprosyn®) diclofenac (Voltaren®), indomethacin (Indocin®), sulindac (Clinoril®), tolmetin (Tolectin®), etodolac (Lodine®), ketorolac (Toradol®), and oxaprozin (Daypro®).

Other anti-angiogenesis agents include ABT 510 (Abbott), apratastat (TMI 005), AZD 8955 (AstraZeneca), incyclinide (Metastat®), and PCK 3145 (Procyon).

Other anti-angiogenesis agents include acitretin (Neotigason®), plitidepsin (Aplidine®), cilengtide (EMD 121974), combretastatin A4 (CA4P), fenretinide (4 HPR), halofuginone (Tempostatin®), Panzem® (2-methoxyestradiol), PF-03446962 (Pfizer), rebimastat (BMS 275291), catumaxomab (Removab®), lenalidomide (Revlimid®) squalamine (EVIZON®), thalidomide (Thalomid®), Ukrain® (NSC 631570), Vitaxin® (MEDI 522), and zoledronic acid (Zometa®).

In some embodiments, the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, ALK inhibitors, ROS1 inhibitors, TrkA inhibitors, TrkB inhibitors, TrkC inhibitors, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa®), cetuximab (Erbitux®), erlotinib (Tarceva®), trastuzumab (Herceptin®), sunitinib (Sutent®) imatinib (Gleevec®), and PD325901 (Pfizer).

Additional examples of signal transduction inhibitors which may be used in conjunction with one or more pharmaceutical compositions provided herein include BMS 214662 (Bristol-Myers Squibb), lonafarnib (Sarasar®), pelitrexol (AG 2037), matuzumab (EMD 7200), nimotuzumab (TheraCIM h-R3®), panitumumab (Vectibix®), Vandetanib (Zactima®), pazopanib (SB 786034), ALT 110 (Alteris Therapeutics), BMW 2992 (Boehringer Ingelheim), and Cervene® (TP 38).

Other examples of signal transduction inhibitor include PF-2341066 (Pfizer), PF-299804 (Pfizer), canertinib (CI 1033), pertuzumab (Omnitarg®), Lapatinib (Tycerb®), pelitinib (EKB 569), miltefosine (Miltefosin®), BMS 599626 (Bristol-Myers Squibb), Lapuleucel-T (Neuvenge®), NeuVax® (E75 cancer vaccine), Osidem® (IDM 1), mubritinib (TAK-165), CP-724,714 (Pfizer), panitumumab (Vectibix®), lapatinib (Tycerb®), PF-299804 (Pfizer), pelitinib (EKB 569), and pertuzumab (Omnitarg®).

Other examples of signal transduction inhibitors include ARRY 142886 (Array Biopharm), everolimus (Certican®), zotarolimus (Endeavor®), temsirolimus (Torisel®), AP 23573 (ARIAD), and VX 680 (Vertex).

Additionally, other signal transduction inhibitors include XL 647 (Exelixis), sorafenib (Nexavar®), LE-AON (Georgetown University), and GI-4000 (GlobeImmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), AG 024322 (Pfizer), LOXO-101 (Loxo Oncology), crizotinib, and ceritinib.

In some embodiments, the pharmaceutical compositions provided herein are used together with classical antineoplastic agents. Classical antineoplastic agents include but are not limited to hormonal modulators such as hormonal, antihormonal, androgen agonist, androgen antagonist and antiestrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

Examples of classical antineoplastic agents used in combination therapy with one or more pharmaceutical compositions provided herein optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with pharmaceutical compositions provided herein include, but are not limited to, suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, paclitaxel, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In some embodiments, the pharmaceutical compositions provided herein are used together with dihydrofolate reductase inhibitors (such as methotrexate and NeuTrexin (trimetrexate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda®), cytosine arabinoside, Gemzar® (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with one or more pharmaceutical compositions provided herein optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta®), DMXAA (Antisoma), ibandronic acid, L-asparaginase, pegaspargase (Oncaspar®), Efaproxiral (Efaproxyn®—radiation therapy)), bexarotene (Targretin®), Tesmilifene (DPPE—enhances efficacy of cytotoxics)), Theratope® (Biomira), Tretinoin (Vesanoid®), tirapazamine (Trizaone®), motexafin gadolinium (Xcytrin®) Cotara® (mAb), and NBI-3001 (Protox Therapeutics), polyglutamate-paclitaxel (Xyotax®) and combinations thereof.

Further examples of classical antineoplastic agents used in combination therapy with one or more pharmaceutical compositions provided herein optionally with one or more other agents include, but are not limited to, as Advexin (ING 201), TNFerade (GeneVec, one or more compounds which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Some embodiments relate to a method for the treatment of breast cancer in a human in need of such treatment. In some embodiments, the method includes, for example, administering to said human an amount of one or more pharmaceutical compositions provided herein in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

Some embodiments provide a method of treating colorectal cancer in a mammal, such as a human, in need of such treatment, by administering an amount of one or more pharmaceutical compositions provided herein in combination with one or more (preferably one to three) anti-cancer agents. Examples of particular anti-cancer agents include those typically used in adjuvant chemotherapy, such as FOLFOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, bacillus Calmette-Guerin (BCG), bevacizumab (Avastin), BIO-117, BIO-145, BMS-184476, BMS-275183, BMS-528664, bortezomib (Velcade), C-1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615) epothilone B (EPO-906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (CI-1042), oxaliplatin (Eloxatin), panitumumab (ABX-EGF, Vectibix), pelitinib (EKB-569), pemetrexed (Alimta), PD-325901, PF-0337210, PF-2341066, RAD-001 (Everolimus), RAV-12, Resveratrol, Rexin-G, S-1 (TS-1), seliciclib, SN-38 liposome, Sodium stibogluconate (SSG), sorafenib (Nexavar), SU-14813, sunitinib (Sutent), temsirolimus (CCI 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Some embodiments provide methods for the treatment of renal cell carcinoma in a human in need of such treatment, comprising administering to said human an amount of pharmaceutical compositions provided herein in combination with one or more (preferably one to three) anti-cancer agents selected from the group consisting of capecitabine (Xeloda), interferon alpha, interleukin-2, bevacizumab (Avastin), gemcitabine (Gemzar), thalidomide, cetuximab (Erbitux), vatalanib (PTK-787), Sutent, AG-13736, SU-11248, Tarceva, Iressa, Lapatinib and Gleevec, wherein the amounts of the active agent together with the amounts of the combination anticancer agents is effective in treating renal cell carcinoma.

Some embodiments provide methods for the treatment of melanoma in a human in need of such treatment, comprising administering to said human an amount of pharmaceutical compositions provided herein, in combination with one or more (preferably one to three) anti-cancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325,901, Axitinib, bevacizumab (Avastin), thalidomide, sorafanib, vatalanib (PTK-787), Sutent, CpG-7909, AG-13736, Iressa, Lapatinib and Gleevec, wherein the amounts of the pharmaceutical compositions provided herein together with the amounts of the combination anticancer agents is effective in treating melanoma.

Some embodiments provide methods for the treatment of lung cancer in a human in need of such treatment, comprising administering to said human an amount of one or more pharmaceutical compositions provided herein in combination with one or more (preferably one to three) anti-cancer agents selected from the group consisting of capecitabine (Xeloda), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, and Paraplatin (carboplatin), wherein the amounts of the active agent together with the amounts of the combination anticancer agents is effective in treating lung cancer.

The presence of at least one genetic alteration in at least one target gene in a cancer subject, wherein the at least one target gene is selected from ALK1, BDNF, NGF, NGFR, NTF3, NTF4, ROS1, SORT1, NTRK1, NTRK2, and NTRK3 may be detected by use of an assay that includes one or more antibodies that bind to at least two, three, four, or all of ALK, ROS1, TrkA, TrkB and TrkC biomarkers. The one or more molecular alterations detected in the biological sample may involve at least two, at least three, or at least four of the biomarkers. The knowledge of the presence of the one or more molecular alterations in the biological sample may be acquired from an assay that includes contacting the biological sample with one or more antibodies or fragments thereof that are specific for the biomarkers. In some instances, the specific antibodies are monoclonal antibodies. In some instances, the specific antibodies include at least one of D5F3®, D4D5®, C17F1®, and combinations thereof. In some instances, the biological sample is contacted with one or more of the specific antibodies simultaneously. In some instances, the biological sample is sequentially contacted with the specific antibodies. In some instances, the one or more molecular alterations results in elevated expression of one or more of the ALK, ROS1, TrkA, TrkB, and TrkC biomarkers. In some instances, the knowledge of the one or more molecular alterations is acquired from an assay wherein determining whether the expression of one or more biomarker is elevated includes: (a) determining the expression level of the one or more biomarkers in the biological sample; and (b) comparing the determined expression level to a reference expression level.

As used herein, the term "reference level" refers to known expression level of the target biomarker(s) in a control person or subject. In some instances, the reference expression level is the expression level of the target biomarker(s) in a healthy person or subject. In some instances, the reference expression level is the expression level of the target biomarker(s) in a population of healthy control cells. In some instances, the reference expression level is the expression level of the target biomarker(s) in a control person or subject that has been previously determined to possess one or more molecular alterations. In some instances, the reference expression level is the expression level of the target biomarker(s) in a population of control cells that have been previously determined to possess one or more molecular alterations.

In some instances, the knowledge of the one or more molecular alterations is acquired from an antibody-based assay. The antibody-based assay can generally be any antibody-based assay, and can be, for example, ELISA, immunohistochemistry, western blotting, mass spectrometry, flow cytometry, protein-microarray, immunofluorescence, and a multiplex detection assay. In some instances, the antibody-based assay includes an immunohistochemistry analysis.

In some instances, identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC activity in a cell extract from a pancreatic cancerous or precancerous cell population. In some instances, identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC transcript accumulation in an RNA population from a pancreatic cancerous or precancerous cell population. In some instances, identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

The term "microarray," as used herein, means an ordered arrangement of array elements (for example, small samples of a biological sample from a subject such as tissue samples) mounted on a solid support capable of binding other molecule species or antibodies. The array elements are arranged so that there are preferably at least one or more different array elements.

The term "solid support," as used herein, means the well-understood solid materials to which various components such as, for example, proteins and nucleic acids, are physically attached, thereby immobilizing the components. The term "solid support," as used herein, means a non-liquid substance. A solid support can be, but is not limited to, a membrane, sheet, gel, glass, plastic or metal. Immobilized components may be associated with a solid support by covalent bonds and/or via non-covalent attractive forces such as hydrogen bond interactions, hydrophobic attractive forces and ionic forces, for example.

In some instances, the microarrays suitable for the methods provided herein have a density of at least 1, 2, 4, 6, 8, 10 spots/cm$^2$, preferably at least 10, 20, 30, 40, 50, 60, 70, 80, 90, 100, 110, 120, 130, 140, 150, 160, 170, 180, 190, 200, more preferably at least 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000 spots/cm$^2$.

In some instances, it is contemplated that the spots on the array may each represent a different species of biomarkers or that the multiple spots on the array may represent the same species of biomarkers. In some instances, the spots each represent an array element of differing identity or characteristics.

In some instances, implementations of the methods according to this and other aspects of the present disclosure further include acquiring knowledge of a genetic alteration in the cancer of the subject from a second analytical assay prior to the administering step. The second analytical assay can generally be any analytical assay known to those having ordinary skill in the art, and can be for example an antibody-based assay, a nucleotide-based assay, or an enzymatic activity assay. Non-limiting examples of suitable second analytical assays include capillary electrophoresis, nucleic acid sequencing, polypeptide sequencing, restriction digestion, nucleic acid amplification-based assays, nucleic acid hybridization assay, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), and a kinase activity assay. Other examples of suitable second analytical assays include ELISA, immunohistochemistry, Western blotting, mass spectrometry, flow cytometry, protein-microarray, immunofluorescence, and multiplex detection assay.

In some instances, FISH analysis is used to identify the chromosomal rearrangement resulting in the one or more molecular alterations such as the fusion genes or gene products as described herein. For example, to perform FISH, at least a first probe tagged with a first detectable label can be designed to target a first gene of a fusion gene, such as in one or more exons of the gene and at least a second probe tagged with a second detectable label can be designed to target a second gene of the fusion gene, such as in one or more exons of the genes (for example, the exons containing the part of the protein that includes the tyrosine kinase domain). The at least one first probe and the at least one second probe will be closer together in a subject who carries the fusion compared to a subject who does not carry the fusion gene or gene product. In some instances, a variation of a FISH assay, for example, "break-apart FISH", is used to evaluate a subject selected by a method provided herein. By this method, at least one probe targeting the fusion junction and at least one probe targeting a subject gene of the fusion, e.g., at one or more exons and or introns of the gene, are utilized. In normal cells, both probes will be observed (or a secondary color will be observed due to the close proximity of the two genes of the gene fusion), and only the single gene probe will be observed when the translocation occurs or the probes, having differing colors, will be separated such that one of ordinary skill in the art observing the probes can determine that a relevant gene fusion or deletion is present in the sample. Generally, FISH assays are performed using formalin-fixed, paraffin-embedded tissue sections that are placed on slides. The DNA from the tissue sample sections is denatured to single-stranded form and subsequently allowed to hybridize with the appropriate DNA probes that can be designed and prepared using methods and techniques known to those having ordinary skill in the art. Following hybridization, any unbound probe may be removed by a series of washes and the nuclei of the cells are counterstained with DAPI (4',6 diamidino-2-phenylindole), a DNA-specific stain that fluoresces blue. Hybridization of the probe or probes are viewed using a fluorescence microscope equipped with appropriate excitation and emission filters, allowing visualization of the fluorescent signals.

For example, a break-apart FISH assay may be used to detect multiple types of rearrangements involving the ALK gene locus. In the method, tumor cells from some subjects having non-small cell lung cancer (NSCLC), display an ALK-positive FISH pattern as detected using single interference filter sets comprising green (FITC), red (Texas red), and blue (4',6-diamidino-2-phenylindole) as well as dual (red/green) and triple (blue, red, green) band-pass filters. A fusion of the ALK gene is visualized as split orange and green signals, single orange signals, or single orange and single green signals.

Relevant molecular alterations with respect to ROS1, TrkA, TrkB and TrkC in biological samples derived from cancer subjects using the same methods as described above, but by modifying the reagents, probes and other materials used in the assays in ways that are appropriate to the target molecular alteration and as can be readily determined by those having ordinary skill in the art.

Other variations of the FISH method known in the art are suitable for evaluating a subject selected in accordance with the methods provided herein.

In some instances of the methods provided herein, the cancer is selected from the group consisting of anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, and papillary thyroid cancer. In some instances are provided such methods, wherein the knowledge of the presence of the one or more molecular alterations is obtained from an assay performed simultaneously on a plurality of biological samples. In some instances, the plurality of biological samples may be assayed in a multitest platform.

As used herein, the term "multitest platform" is intended to encompass any suitable means to contain one or more reaction mixtures, suspensions, or detection reactions. As such, the outcomes of a number of screening events can be assembled onto one surface, resulting in a "multitest platform" having, or consisting of multiple elements or parts to do more than one experiment simultaneously. It is intended that the term "multitest platform" encompasses protein chips, microtiter plates, multi-well plates, microcards, test tubes, petri plates, trays, slides, and the like. In some instances, multiplexing can further include simultaneously conducting a plurality of screening events in each of a plurality of separate biological samples. For example, the number of biological samples analyzed can be based on the number of spots on a slide and the number of tests conducted in each spot (as described in greater detail in Example 2). In another example, the number of biological samples analyzed can be based on the number of wells in a multi-well plate and the number of tests conducted in each well. For example, 6-well, 12-well, 24-well, 48-well, 96-well, 384-well, 1536-well or 3456-well microtiter plates can be useful in the presently disclosed methods, although it will be appreciated by those in the art, not each microtiter well need contain a subject biological sample. Depending on the size of the microtiter plate and the number of the subject biological samples in each well, very high numbers of tests can be run simultaneously. Although multiplexing has been exemplified in Example 2 with respect to micro-slides, it will be understood that other formats can be used for multiplexing.

In some instances are provided such methods, wherein the plurality of biological samples includes at least 6, 12, 24, 48, 96, 200, 384, 400, 500, 1000, 1250, 1500, or 3000 samples.

In some instances are provided such methods, wherein the one or more molecular alterations is selected from a genetic mutation, a gene amplification, a gene rearrangement, a single-nucleotide variation (SNV), a deletion, an insertion, an InDel mutation, a single nucleotide point mutation (SNP), an epigenetic alteration, a splicing variant, an RNA/protein overexpression, and an aberrant RNA/protein expression. In some instances are provided such methods, wherein the genetic alteration includes an insertion of a heterologous nucleic acid sequence within a coding sequence of a biomarker gene. In some instances are provided such methods, wherein the insertion forms a chimeric nucleic acid sequence that encodes a fusion peptide.

In some instances are provided such methods, wherein the acquiring knowledge of the one or more molecular alterations further comprises determining a nucleic acid sequence and/or an amino acid sequence comprising the one or more molecular alterations. In some instances, the nucleic acid sequence comprising the one or more molecular alterations from a selected cancer subject tumor is sequenced. In some instances, the sequence is determined by a next generation sequencing method.

Some embodiments provide a pharmaceutical composition comprising a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide in combination with one or more chemotherapeutic agents or radiotherapy, such as radiotherapy as commonly administered to treat, ameliorate the symptoms of, or prevent or delay the onset of cancer. Such agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

Some embodiments provide a product or kit comprising a pharmaceutical composition as provided herein comprising N-[5-(3,5-difluorobenzyl)-1H-indazol-3-yl]-4-(4-methyl-piperazin-1-yl)-2-(tetrahydro-2H-pyran-4-ylamino)-benzamide and one or more chemotherapeutic agents, as a combined preparation for simultaneous, separate or sequential use in anticancer therapy.

Some embodiments include any of the methods described herein, wherein said cancer is selected from non-small cell lung cancer, papillary thyroid cancer, neuroblastoma, pancreatic cancer and colorectal cancer. Some embodiments are any of the methods described herein wherein said cancer is non-small cell lung cancer. Some embodiments include any of the methods described herein, wherein said cancer is said cancer is papillary thyroid cancer. Some embodiments include any of the methods described herein, wherein said cancer is wherein said cancer is neuroblastoma. Some embodiments include any of the methods described herein, wherein said cancer is wherein said cancer is pancreatic cancer.

Some embodiments include any of the methods described herein, wherein said cancer is wherein said cancer is colorectal cancer.

Some embodiments relate to any of the pharmaceutical compositions provided herein for use as a medicament. Some embodiments relate to the use of any of the pharmaceutical compositions provided herein for the manufacture of a medicament for the treatment of abnormal cell growth.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 5 hours, or between about 2.5 hours and about 4.7 hours, or between about 2.4 hours and about 4.7 hours, or between about 2.6 hours and about 4.8 hours, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 5 hours, or between about 2.5 hours and about 4.7 hours, or between about 2.4 hours and about 4.7 hours, or between about 2.6 hours and about 4.8 hours, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4 hours and about 8 hours, or between about 4.6 hours and about 5.4 hours, or between about 4.5 hours and about 7.2 hours, or between about 4.2 hours and about 6.7 hours, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4 hours and about 8 hours, or between about 4.6 hours and about 5.4 hours, or between about 4.5 hours and about 7.2 hours, or between about 4.2 hours and about 6.7 hours, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and about 3500 nM, or between about 1500 nM and about 2800 nM, or between about 1490 nM and about 3030 nM, or between about 1670 nM and about 2930 nM, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and about 3500 nM, or between about 1500 nM and about 2800 nM, or between about 1490 nM and about 3030 nM, or between about 1670 nM and about 2930 nM, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM, or between about 1810 nM and about 3070 nM, or between about 2210 nM and about 2990 nM, or between about 1990 nM and about 2810 nM, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM, or between about 1810 nM and about 3070 nM, or between about 2210 nM and about 2990 nM, or between about 1990 nM and about 2810 nM, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,100 nM*hr and about 71,700 nM*hr, or between about 32,500 nM*hr and about 79,700 nM*hr, or between about 37,100 nM*hr and about 77,300 nM*hr, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,100 nM*hr and about 71,700 nM*hr, or between about 32,500 nM*hr and about 79,700 nM*hr, or between about 37,100 nM*hr and about 77,300 nM*hr, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 38,900 nM*hr and about 78,700 nM*hr, or between about 58,900 nM*hr and about 84,700 nM*hr, or between about 51,300 nM*hr and about 77,500 nM*hr, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 38,900 nM*hr and about 78,700 nM*hr, or between about 58,900 nM*hr and about 84,700 nM*hr, or between about 51,300 nM*hr and about 77,500 nM*hr, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,700 nM*hr and about 72,900 nM*hr, or between about 33,200 nM*hr and about 81,200 nM*hr, or between about 37,800 nM*hr and about 78,800 nM*hr, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3- yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,700 nM*hr and about 72,900 nM*hr, or between about 33,200 nM*hr and about 81,200 nM*hr, or between about 37,800 nM*hr and about 78,800 nM*hr, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 39,100 nM*hr and about 79,700 nM*hr, or between about 59,400 nM*hr and about 87,200 nM*hr, or between about 51,700 nM*hr and about 79,700 nM*hr, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 39,100 nM*hr and about 79,700 nM*hr, or between about 59,400 nM*hr and about 87,200 nM*hr, or between about 51,700 nM*hr and about 79,700 nM*hr, following said administration of said pharmaceutical composition to said subject. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 5 hours, or between about 2.5 hours and about 4.7 hours, or between about 2.4 hours and about 4.7 hours, or between about 2.6 hours and about 4.8 hours, following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 5 hours, or between about 2.5 hours and about 4.7 hours, or between about 2.4 hours and about 4.7 hours, or between about 2.6 hours and about 4.8 hours, following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4 hours and about 8 hours, or between about 4.6 hours and about 5.4 hours, or between about 4.5 hours and about 7.2 hours, or between about 4.2 hours and about 6.7 hours, following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5- difluorobenzyl)-1H-indazol-3-yl]-4-(4-methyl-piperazin-1-yl)-2-(tetrahydro-pyran-4-ylamino)-benzamide in the plasma of said subject is between about 4 hours and about 8 hours, or between about 4.6 hours and about 5.4 hours, or between about 4.5 hours and about 7.2 hours, or between about 4.2 hours and about 6.7 hours, following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and about 3500 nM, or between about 1500 nM and about 2800 nM, or between about 1490 nM and about 3030 nM, or between about 1670 nM and about 2930 nM, following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and about 3500 nM, or between about 1500 nM and about 2800 nM, or between about 1490 nM and about 3030 nM, or between about 1670 nM and about 2930 nM, following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM, or between about 1810 nM and about 3070 nM, or between about 2210 nM and about 2990 nM, or between about 1990 nM and about 2810 nM, following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM, or between about 1810 nM and about 3070 nM, or between about 2210 nM and about 2990 nM, or between about 1990 nM and about 2810 nM, following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,100 nM*hr and about 71,700 nM*hr, or between about 32,500 nM*hr and about 79,700 nM*hr, or between about 37,100 nM*hr and about 77,300 nM*hr, following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,100 nM*hr and about 71,700 nM*hr, or between about 32,500 nM*hr and about 79,700 nM*hr, or between about 37,100 nM*hr and about 77,300 nM*hr, following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 38,900 nM*hr and about 78,700 nM*hr, or between about 58,900 nM*hr and about 84,700 nM*hr, or between about 51,300 nM*hr and about 77,500 nM*hr, following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 38,900 nM*hr and about 78,700 nM*hr, or between about 58,900 nM*hr and about 84,700 nM*hr, or between about 51,300 nM*hr and about 77,500 nM*hr, following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,700 nM*hr and about 72,900 nM*hr, or between about 33,200 nM*hr and about 81,200 nM*hr, or between about 37,800 nM*hr and about 78,800 nM*hr, following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,700 nM*hr and about 72,900 nM*hr, or between about 33,200 nM*hr and about 81,200 nM*hr, or between about 37,800 nM*hr and about 78,800 nM*hr, following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 39,100 nM*hr and about 79,700 nM*hr, or between about 59,400 nM*hr and about 87,200 nM*hr, or between about 51,700 nM*hr and about 79,700 nM*hr, following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said acidulant is tartaric acid, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 39,100 nM*hr and about 79,700 nM*hr, or between about 59,400 nM*hr and about 87,200 nM*hr, or between about 51,700 nM*hr and about 79,700 nM*hr, following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 5 hours, or between about 2.5 hours and about 4.7 hours, or between about 2.4 hours and about 4.7 hours, or between about 2.6 hours and about 4.8 hours, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and about 5 hours, or between about 2.5 hours and about 4.7 hours, or between about 2.4 hours and about 4.7 hours, or between about 2.6 hours and about 4.8 hours, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4 hours and about 8 hours, or between about 4.6 hours and about 5.4 hours, or between about 4.5 hours and about 7.2 hours, or between about 4.2 hours and about 6.7 hours, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4 hours and about 8 hours, or between about 4.6 hours and about 5.4 hours, or between about 4.5 hours and about 7.2 hours, or between about 4.2 hours and about 6.7 hours, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and about 3500 nM, or between about 1500 nM and about 2800 nM, or between about 1490 nM and about 3030 nM, or between about 1670 nM and about 2930 nM, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and about 3500 nM, or between about 1500 nM and about 2800 nM, or between about 1490 nM and about 3030 nM, or between about 1670 nM and about 2930 nM, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM, or between about 1810 nM and about 3070 nM, or between about 2210 nM and about 2990 nM, or between about 1990 nM and about 2810 nM, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM, or between about 1810 nM and about 3070 nM, or between about 2210 nM and about 2990 nM, or between about 1990 nM and about 2810 nM, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,100 nM*hr and about 71,700 nM*hr, or between about 32,500 nM*hr and about 79,700 nM*hr, or between about 37,100 nM*hr and about 77,300 nM*hr, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,100 nM*hr and about 71,700 nM*hr, or between about 32,500 nM*hr and about 79,700 nM*hr, or between about 37,100 nM*hr and about 77,300 nM*hr, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 38,900 nM*hr and about 78,700 nM*hr, or between about 58,900 nM*hr and about 84,700 nM*hr, or between about 51,300 nM*hr and about 77,500 nM*hr, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 38,900 nM*hr and about 78,700 nM*hr, or between about 58,900 nM*hr and about 84,700 nM*hr, or between about 51,300 nM*hr and about 77,500 nM*hr, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,700 nM*hr and about 72,900 nM*hr, or between about 33,200 nM*hr and about 81,200 nM*hr, or between about 37,800 nM*hr and about 78,800 nM*hr, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr, or between about 34,700 nM*hr and about 72,900 nM*hr, or between about 33,200 nM*hr and about 81,200 nM*hr, or between about 37,800 nM*hr and about 78,800 nM*hr, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 39,100 nM*hr and about 79,700 nM*hr, or between about 59,400 nM*hr and about 87,200 nM*hr, or between about 51,700 nM*hr and about 79,700 nM*hr, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject at a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr, or between about 39,100 nM*hr and about 79,700 nM*hr, or between about 59,400 nM*hr and about 87,200 nM*hr, or between about 51,700 nM*hr and about 79,700 nM*hr, following said administration of said pharmaceutical composition to said subject, wherein said pharmaceutical composition is in the form of a capsule. In some embodiments, the at least one acidulant is an organic acidulant. In some embodiments, the at least one acidulant is selected from tartaric acid, maleic acid, fumaric acid, citric acid, and betaine hydrochloride. In some embodiments, the least one acidulant is fumaric acid. In some embodiments, the at least one acidulant is tartaric acid. In some embodiments, the said at least one acidulant is maleic acid. In some embodiments, the said at least one acidulant is citric acid. In some embodiments, the said at least one acidulant is betaine hydrochloride.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 5 hours, or between about 2.5 hours and about 4.7 hours, or between about 2.4 hours and about 4.7 hours, or between about 2.6 hours and about 4.8 hours, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 5 hours, or between about 2.5 hours and about 4.7 hours, or between about 2.4 hours and about 4.7 hours, or between about 2.6 hours and about 4.8 hours, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 8 hours, or between about 4.6 hours and about 5.4 hours, or between about 4.5 hours and about 7.2 hours, or between about 4.2 hours and about 6.7 hours, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 8 hours, or between about 4.6 hours and about 5.4 hours, or between about 4.5 hours and about 7.2 hours, or between about 4.2 hours and about 6.7 hours, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1200 nM and about 3500 nM, or between about 1500 nM and about 2800 nM, or between about 1490 nM and about 3030 nM, or between about 1670 nM and about 2930 nM, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1200 nM and about 3500 nM, or between about 1500 nM and about 2800 nM, or between about 1490 nM and about 3030 nM, or between about 1670 nM and about 2930 nM, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1500 nM and about 3500 nM, or between about 1810 nM and about 3070 nM, or between about 2210 nM and about 2990 nM, or between about 1990 nM and about 2810 nM, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1500 nM and about 3500 nM, or between about 1810 nM and about 3070 nM, or between about 2210 nM and about 2990 nM, or between about 1990 nM and about 2810 nM, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 30,000 nM*hr and about 85,000 nM*hr, or between about 34,100 nM*hr and about 71,700 nM*hr, or between about 32,500 nM*hr and about 79,700 nM*hr, or between about 37,100 nM*hr and about 77,300 nM*hr, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 30,000 nM*hr and about 85,000 nM*hr, or between about 34,100 nM*hr and about 71,700 nM*hr, or between about 32,500 nM*hr and about 79,700 nM*hr, or between about 37,100 nM*hr and about 77,300 nM*hr, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 35,000 nM*hr and about 90,000 nM*hr, or between about 38,900 nM*hr and about 78,700 nM*hr, or between about 58,900 nM*hr and about 84,700 nM*hr, or between about 51,300 nM*hr and about 77,500 nM*hr, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 35,000 nM*hr and about 90,000 nM*hr, or between about 38,900 nM*hr and about 78,700 nM*hr, or between about 58,900 nM*hr and about 84,700 nM*hr, or between about 51,300 nM*hr and about 77,500 nM*hr, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 30,000 nM*hr and about 85,000 nM*hr, or between about 34,700 nM*hr and about 72,900 nM*hr, or between about 33,200 nM*hr and about 81,200 nM*hr, or between about 37,800 nM*hr and about 78,800 nM*hr, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 30,000 nM*hr and about 85,000 nM*hr, or between about 34,700 nM*hr and about 72,900 nM*hr, or between about 33,200 nM*hr and about 81,200 nM*hr, or between about 37,800 nM*hr and about 78,800 nM*hr, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 35,000 nM*hr and about 90,000 nM*hr, or between about 39,100 nM*hr and about 79,700 nM*hr, or between about 59,400 nM*hr and about 87,200 nM*hr, or between about 51,700 nM*hr and about 79,700 nM*hr, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 35,000 nM*hr and about 90,000 nM*hr, or between about 39,100 nM*hr and about 79,700 nM*hr, or between about 59,400 nM*hr and about 87,200 nM*hr, or between about 51,700 nM*hr and about 79,700 nM*hr, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 5 hours following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 5 hours following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 6 hours following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 6 hours following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 8 hours following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 8 hours following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 7 hours following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 7 hours following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1500 nM and about 2800 nM following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1500 nM and about 2800 nM following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1490 nM and about 3030 nM following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1490 nM and about 3030 nM following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1670 nM and about 2930 nM following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1670 nM and about 2930 nM following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1810 nM and about 3070 nM following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1810 nM and about 3070 nM following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2210 nM and about 2990 nM following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2210 nM and about 2990 nM following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1990 nM and about 2810 nM following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1990 nM and about 2810 nM following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 34,100 nM*hr and about 71,700 nM*hr following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 34,100 nM*hr and about 71,700 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 32,500 nM*hr and about 79,700 nM*hr following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 32,500 nM*hr and about 79,700 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 37,100 nM*hr and about 77,300 nM*hr following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 37,100 nM*hr and about 77,300 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 38,900 nM*hr and about 78,700 nM*hr following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 38,900 nM*hr and about 78,700 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 58,900 nM*hr and about 84,700 nM*hr following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 58,900 nM*hr and about 84,700 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 51,300 nM*hr and about 77,500 nM*hr following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 51,300 nM*hr and about 77,500 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 34,700 nM*hr and about 72,900 nM*hr following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 34,700 nM*hr and about 72,900 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 33,200 nM*hr and about 81,200 nM*hr following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 33,200 nM*hr and about 81,200 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 37,800 nM*hr and about 78,800 nM*hr following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 37,800 nM*hr and about 78,800 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 39,100 nM*hr and about 79,700 nM*hr following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 39,100 nM*hr and about 79,700 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 59,400 nM*hr and about 87,200 nM*hr following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 59,400 nM*hr and about 87,200 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 51,700 nM*hr and about 79,700 nM*hr following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject of between about 51,700 nM*hr and about 79,700 nM*hr following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.6 hours, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.6 hours, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.5 hours, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.5 hours, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.7 hours, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.7 hours, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5 hours, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5 hours, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5.8 hours, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5.8 hours, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5.4 hours, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5.4 hours, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2150 nM, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2150 nM, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2260 nM, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2260 nM, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2300 nM, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2300 nM, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2440 nM, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2440 nM, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2600 nM, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2600 nM, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2400 nM, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2400 nM, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 52,900 nM*hr, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 52,900 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 56,100 nM*hr, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 56,100 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 57,200 nM*hr, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 57,200 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 58,800 nM*hr, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 58,800 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 71,800 nM*hr, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 71,800 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 64,400 nM*hr, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(0 to 120) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 64,400 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 53,800 nM*hr, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 53,800 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 57,200 nM*hr, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 57,200 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 58,300 nM*hr, based on a 90 percent confidence interval, following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 58,300 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydropyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydropyran-4-ylamino)-benzamide in the plasma of a subject that is between 80% to 125% of 59,400 nM*hr, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 59,400 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 73,300 nM*hr, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 73,300 nM*hr, based on a 90 percent confidence interval, following administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 65,700 nM*hr, based on a 90 percent confidence interval, following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide; and (b) means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 65,700 nM*hr, based on a 90 percent confidence interval, following administration of said pharmaceutical composition to said subject.

EXAMPLES

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

As will be understood by one skilled in the art, for any and all purposes, such as in terms of providing a written description, all ranges provided herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each subject member. Thus, for example, a group having 1-3 articles refers to groups having 1, 2, or 3 articles. Similarly, a group having 1-5 articles refers to groups having 1, 2, 3, 4, or 5 articles, and so forth.

Example 1

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and fumaric acid was prepared as follows.

| Component | Target amount per dosage unit (mg) | % w/w | Target weight per batch (g) | Actual weight per batch (g) |
| --- | --- | --- | --- | --- |
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 44.44 | 66.67 | 66.67 |
| Fumaric acid | 50.0 | 11.11 | 16.67 | 16.67 |
| Isomalt | 173.0 | 38.44 | 57.67 | 57.67 |
| Pregelatinized starch, NF (Starch 1500) | 22.50 | 5.00 | 7.50 | 7.50 |
| Colloidal silicon dioxide (Cab-O-Sil ®) | 2.25 | 0.50 | 0.75 | 0.7542 |
| Magnesium stearate, NF (HyQual ® 5712 Powder) | 2.25 | 0.50 | 0.75 | 0.75 |
| Total | 450.00 | 100.00 | 150.00 | 150.01 |

N-[5-(3,5-difluorobenzyl)-1H-indazol-3-yl]-4-(4-methyl-piperazin-1-yl)-2-(tetrahydro-2H-pyran-4-ylamino)-benzamide was milled and the resulting materials were passed through a 60-mesh screen. The specified amount of fumaric acid was ground using a mortar and pestle and the resulting materials were passed through a 60-mesh screen. The fumaric acid was added to a V-blender and was blended for about 30 seconds, after which the N-[5-(3,5-difluorobenzyl)-1H-indazol-3-yl]-4-(4-methyl-piperazin-1-yl)-2-(tetrahydro-2H-pyran-4-ylamino)-benzamide was added to the blender and the resulting mixture was blended for about one minute at 25 rpm. About one-half of the isomalt (estimated by sight), the pregelatinized starch, and the colloidal silicon dioxide were added to the blender and the resulting mixture was blended for about 3 minutes. The remainder of the isomalt was added along with the magnesium stearate to a large weighing boat, the mixture was stirred. The resulting mixture of isomalt and magnesium stearate was then added to the blender and the mixture was blended for about 3 minutes at 25 rpm. The mixture was removed from the blender, screened through a 40-mesh screen and placed into a plastic bag. Bisected, modified oval tablets were prepared from the mixture using tooling with dimensions of 0.3200× 0.5800. Some sticking issues were observed with this tooling, so it was switched to tooling for a caplet having dimensions of 0.25×0.75, which resulted in tablets that were less susceptible to sticking. Tablets were then prepared by wiping the tooling with magnesium stearate on a swab after each tableting run. Generally, the flow of the powder prior to tableting was somewhat poor and it required stirring, but compression of the tablets was acceptable when the tooling was wiped each time with magnesium stearate.

Example 2

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and glycine hydrochloride was prepared as follows.

| Component | Target amount per dosage unit (mg) | % w/w | Target weight per batch (g) | Actual weight per batch (g) |
|---|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 44.44 | 66.67 | 66.67 |
| Glycine hydrochloride | 48.00 | 10.67 | 16.00 | 16.00 |
| Isomalt | 175.0 | 38.89 | 58.33 | 58.33 |
| Pregelatinized starch, NF (Starch 1500) | 22.50 | 5.00 | 7.50 | 7.50 |
| Colloidal silicon dioxide (Cab-O-Sil ®) | 2.25 | 0.50 | 0.75 | 0.7542 |
| Magnesium stearate, NF (HyQual ® 5712 Powder) | 2.25 | 0.50 | 0.75 | 0.75 |
| Total | 450.00 | 100.00 | 150.00 | 150.00 |

Glycine hydrochloride was ground in a mortar and pestle. N-[5-(3,5-difluorobenzyl)-1H-indazol-3-yl]-4-(4-methyl-piperazin-1-yl)-2-(tetrahydro-2H-pyran-4-ylamino)-benzamide was milled, but was not screened. Approximately the same volumes of isomalt and magnesium stearate were added to a weighing boat and stirred together. Approximately the same volumes of isomalt and colloidal silicon dioxide were added to a weighing boat. The mixture of isomalt and colloidal silicon dioxide were added to a plastic bag, along with the remaining isomalt, pregelatinized starch, and glycine hydrochloride. The resulting mixture was mixed briefly in the plastic bag, after which time the N-[5-(3,5-difluorobenzyl)-1H-indazol-3-yl]-4-(4-methyl-piperazin-1-yl)-2-(tetrahydro-2H-pyran-4-ylamino)-benzamide was added to the plastic bag and the resulting mixture was mixed in the plastic bag by hand for about one minute. The resulting mixture in the plastic bag was screened through a 40-mesh screen and was added to a V-blender. The mixture of magnesium stearate and isomalt from the weighing boat were also added to the V-blender and the resulting mixture was blended at about 25 rpm for about 10 minutes.

Tablets were prepared from the above mixture using tooling for caplets having dimensions measuring 0.2500× 0.7500. Sticking and capping occurred on the first two tablets. The tableting tooling was cleaned and swabbed with magnesium stearate, but tablet sticking was still significant and the weight of the resulting tablets varied significantly. The flow of the powder entering the tableting tooling was sensitive to the head space in the hopper.

Example 3

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride was prepared as follows.

| Component | Target amount per dosage unit (mg) | % w/w | Target weight per batch (g) | Actual weight per batch (g) |
|---|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 44.44 | 66.67 | 66.67 |
| Betaine hydrochloride | 66.50 | 14.78 | 22.17 | 22.17 |
| Isomalt | 156.50 | 34.78 | 52.17 | 52.17 |
| Pregelatinized starch, NF (Starch 1500) | 22.50 | 5.00 | 7.50 | 7.50 |
| Colloidal silicon dioxide (Cab-O-Sil ®) | 2.25 | 0.50 | 0.75 | 0.75 |
| Magnesium stearate, NF (HyQual ® 5712 Powder) | 2.25 | 0.50 | 0.75 | 0.75 |
| Total | 450.00 | 100.00 | 150.00 | 150.00 |

The betaine hydrochloride was ground in a mortar and pestle before use. The N-[5-(3,5-difluorobenzyl)-1H-indazol-3-yl]-4-(4-methyl-piperazin-1-yl)-2-(tetrahydro-2H-pyran-4-ylamino)-benzamide was milled before use. Approximately the same volumes of isomalt and magnesium stearate were added to a weighing boat and stirred together. Approximately the same volumes of isomalt and colloidal silicon dioxide were added to a weighing boat and stirred together in a plastic bag. The remaining isomalt, pregelatinized starch and betaine hydrochloride were added to a plastic bag and briefly mixed together. All the N-[5-(3,5-difluorobenzyl)-1H-indazol-3-yl]-4-(4-methyl-piperazin-1-yl)-2-(tetrahydro-2H-pyran-4-ylamino)-benzamide was added to the plastic bag and the resulting mixture was mixed by hand in the plastic bag for about one minute. The resulting mixture in the plastic bag was screened through a 40-mesh screen and was added to a V-blender. The mixture of magnesium stearate and isomalt from the weighing boat were also added to the V-blender and the resulting mixture was blended at about 25 rpm for about 3 minutes.

Tablets were prepared from the above mixture using tooling for caplets having dimensions measuring 0.2500× 0.750. The flow of the powder in the hopper was improved and wiping of the tooling with magnesium stearate was only infrequently required.

Example 4

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride was prepared as follows.

| Component | Target amount per dosage unit (mg) | % w/w | Target weight per batch (g) | Actual weight per batch (g) |
|---|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 57.14 | 85.71 | 85.71 |
| Betaine hydrochloride | 66.50 | 19.00 | 28.50 | 28.50 |
| Isomalt | 37.50 | 10.71 | 16.07 | 16.07 |
| Microcrystalline cellulose, NF (Avicel ® PH-200 LM) | 24.90 | 7.11 | 10.67 | 10.67 |
| Pregelatinized starch, NF (Starch 1500) | 17.50 | 5.00 | 7.50 | 7.50 |
| Colloidal silicon dioxide (Cab-O-Sil ®) | 1.80 | 0.51 | 0.77 | 0.77 |
| Magnesium stearate, NF (HyQual ® 5712 Powder) | 1.80 | 0.51 | 0.77 | 0.77 |
| Total | 350.00 | 100.00 | 150.00 | 150.00 |

The betaine hydrochloride was ground in a mortar and pestle before use. The N-[5-(3,5-difluorobenzyl)-1H-indazol-3-yl]-4-(4-methyl-piperazin-1-yl)-2-(tetrahydro-2H-pyran-4-ylamino)-benzamide was milled before use. Approximately the same volumes of isomalt and magnesium stearate were added to a weighing boat and stirred together. Approximately the same volumes of isomalt and colloidal silicon dioxide were added to a weighing boat and stirred together in a plastic bag. The remaining isomalt, pregelatinized starch, microcrystalline cellulose and betaine hydrochloride were added to a plastic bag and briefly mixed together. All the N-[5-(3,5-difluorobenzyl)-1H-indazol-3-yl]-4-(4-methyl-piperazin-1-yl)-2-(tetrahydro-2H-pyran-4-ylamino)-benzamide was added to the plastic bag and the resulting mixture was mixed by hand in the plastic bag for about two minutes. The resulting mixture in the plastic bag was screened through a 40-mesh screen and was added to a V-blender. The mixture of magnesium stearate and isomalt from the weighing boat were also added to the V-blender and the resulting mixture was blended for about 3 minutes at 25 rpm.

Tablets were prepared from the above mixture using tooling for caplets having dimensions measuring 0.2500× 0.7500. The flow of the powder in the hopper was generally poor and frequent stirring in the hopper was required.

Example 5

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride was prepared as follows.

| Component | Target amount per dosage unit (mg) | % w/w | Target weight per batch (g) | Actual weight per batch (g) |
|---|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 44.44 | 66.67 | 66.67 |
| Betaine hydrochloride | 66.50 | 14.78 | 22.17 | 22.17 |
| Isomalt | 91.00 | 20.22 | 30.33 | 30.33 |
| microcrystalline cellulose, NF (Avicel ® PH-200 LM) | 61.00 | 13.56 | 20.33 | 20.33 |
| Croscarmellose sodium (Ac-Di-Sol ® SD-711) | 4.50 | 1.00 | 1.50 | 1.50 |
| Pregelatinized starch, NF (Starch 1500) | 22.50 | 5.00 | 7.50 | 7.50 |
| Colloidal silicon dioxide (Cab-O-Sil ®) | 2.25 | 0.50 | 0.75 | 0.75 |
| Magnesium stearate, NF (HyQual ® 5712 Powder) | 2.25 | 0.50 | 0.75 | 0.75 |
| Total | 450.00 | 100.00 | 150.00 | 150.00 |

The betaine hydrochloride was ground in a mortar and pestle before use. The N-[5-(3,5-difluorobenzyl)-1H-indazol-3-yl]-4-(4-methyl-piperazin-1-yl)-2-(tetrahydro-2H-pyran-4-ylamino)-benzamide was milled before use. Approximately the same volumes of isomalt and magnesium stearate were added to a weighing boat and stirred together. Approximately the same volumes of isomalt and colloidal silicon dioxide were added to a weighing boat and stirred together in a plastic bag. The remaining isomalt, pregelatinized starch, microcrystalline cellulose, croscarmellose sodium, and betaine hydrochloride were added to a plastic bag and mixed together for about one minute. All the N-[5-(3,5-difluorobenzyl)-1H-indazol-3-yl]-4-(4-methyl-piperazin-1-yl)-2-(tetrahydro-2H-pyran-4-ylamino)-benzamide was added to the plastic bag and the resulting mixture was mixed by hand in the plastic bag. The resulting mixture in the plastic bag was screened through a 40-mesh screen and was added to a V-blender. The mixture of magnesium stearate and isomalt from the weighing boat were also added to the V-blender and the resulting mixture was blended for about 3 minutes at 25 rpm.

Tablets were prepared from the above mixture using tooling for caplets having dimensions measuring 0.2500× 0.7500. The sticking of the powder to the tooling was an issue and required the use of magnesium stearate for each compression and the powder had to be stirred in the hopper twice during compression (tablets #3 and #29).

Example 6

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride was prepared as follows.

| Component | Target amount per dosage unit (mg) | % w/w | Target weight per batch (g) | Actual weight per batch (g) |
|---|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 44.44 | 66.67 | 66.67 |
| Betaine hydrochloride | 66.50 | 14.78 | 22.17 | 22.17 |
| Isomalt | 94.00 | 20.889 | 31.33 | 31.33 |

-continued

| Component | Target amount per dosage unit (mg) | % w/w | Target weight per batch (g) | Actual weight per batch (g) |
|---|---|---|---|---|
| microcrystalline cellulose, NF (Avicel ® PH-200 LM) | 62.50 | 13.89 | 20.83 | 20.83 |
| Pregelatinized starch, NF (Starch 1500) | 22.50 | 5.00 | 7.50 | 7.50 |
| Colloidal silicon dioxide (Cab-O-Sil ®) | 2.25 | 0.50 | 0.75 | 0.75 |
| Magnesium stearate, NF (HyQual ® 5712 Powder) | 2.25 | 0.50 | 0.75 | 0.75 |
| Total | 450.00 | 100.00 | 150.00 | 150.00 |

The betaine hydrochloride was ground in a mortar and pestle before use. The N-[5-(3,5-difluorobenzyl)-1H-indazol-3-yl]-4-(4-methyl-piperazin-1-yl)-2-(tetrahydro-2H-pyran-4-ylamino)-benzamide was milled before use. Approximately the same volumes of isomalt and magnesium stearate were added to a weighing boat and stirred together. Approximately the same volumes of isomalt and colloidal silicon dioxide were added to a weighing boat and stirred together in a plastic bag. The remaining isomalt, pregelatinized starch, microcrystalline cellulose, and betaine hydrochloride were added to a plastic bag and mixed together for about one minute. All the N-[5-(3,5-difluorobenzyl)-1H-indazol-3-yl]-4-(4-methyl-piperazin-1-yl)-2-(tetrahydro-2H-pyran-4-ylamino)-benzamide was added to the plastic bag and the resulting mixture was mixed by hand in the plastic bag. The resulting mixture in the plastic bag was screened through a 40-mesh screen and was added to a V-blender. The mixture of magnesium stearate and isomalt from the weighing boat were also added to the V-blender and the resulting mixture was blended for about 3 minutes at 25 rpm.

Tablets were prepared from the above mixture using tooling for caplets having dimensions measuring 0.2500× 0.7500. The sticking of the powder to the tooling was an issue and required swabbing of the tooling with magnesium stearate on every tablet compression. In addition, the weight of the resulting tablets was variable and required some stirring of the powder in the hopper.

Example 7

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride was prepared as follows.

| Component | Target amount per dosage unit (mg) | % w/w | Target weight per batch (g) | Actual weight per batch (g) |
|---|---|---|---|---|
| First Layer | | | | |
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 44.44 | 66.67 | 66.67 |
| Isomalt | 78.25 | 17.39 | 26.08 | 26.08 |
| Pregelatinized starch, NF (Starch 1500) | 11.25 | 2.50 | 3.75 | 3.75 |
| Colloidal silicon dioxide (Cab-O-Sil ®) | 2.25 | 0.50 | 0.75 | 0.75 |
| Magnesium stearate, NF (HyQual ® 5712 Powder) | 2.25 | 0.50 | 0.75 | 0.75 |
| Total | 292.88 | 65.08 | 97.63 | 97.63 |
| Second Layer | | | | |
| Betaine hydrochloride | 66.50 | 14.78 | 22.17 | 22.17 |
| Isomalt | 78.25 | 17.39 | 26.08 | 26.08 |
| Pregelatinized starch, NF (Starch 1500) | 11.25 | 2.50 | 3.75 | 3.75 |
| Magnesium stearate, NF (HyQual ® 5712 Powder) | 1.13 | 0.25 | 0.38 | 0.38 |
| Total for second layer | 157.12 | | | |
| Overall total | 450.00 | 100.00 | 150.00 | 150.00 |

The betaine hydrochloride was ground in a mortar and pestle before use. The N-[5-(3,5-difluorobenzyl)-1H-indazol-3-yl]-4-(4-methyl-piperazin-1-yl)-2-(tetrahydro-2H-pyran-4-ylamino)-benzamide was milled before use. Approximately the same volumes of isomalt and magnesium stearate were added to a weighing boat and stirred together for layer #1. Approximately the same volumes of isomalt and colloidal silicon dioxide were added to a weighing boat and stirred together for layer #1.

For layer #2, the betaine hydrochloride, isomalt, and pregelatinized starch were added to a plastic bag, mixed by hand and then added to a V-blender. About the same volume of isomalt and magnesium were mixed together by stirring and the resulting mixture was also added to the V-blender and the mixture was blended for about 3 minutes at 25 rpm.

For layer #1, the mixture of colloidal silicon dioxide and isomalt were added to a plastic bag and mixed by shaking. To the bag were added the remaining isomalt, pregelatinized starch and the mixture was shaken. All of the N-[5-(3,5-difluorobenzyl)-1H-indazol-3-yl]-4-(4-methyl-piperazin-1-yl)-2-(tetrahydro-2H-pyran-4-ylamino)-benzamide was added to the bag, the bag was shaken and the resulting mixture was added to a V-blender. The pre-mixed isomalt and magnesium stearate was added to the V-blender. The resulting mixture was removed from the blender, screened through a 40-mesh screen, added back into the blender and blended for about 3 minutes at 25 rpm.

The blends were weighed out for subject layers for each tablet using tooling measuring 0.2500×0.7500: first layer was about 292.88 mg and the second layer was about 157.12 mg. The tablets were compressed using a Carver press with a force of about 400 pounds for the first layer and about 1400 pounds for the finished tablet. Magnesium stearate was dusted onto the upper and lower punches prior to loading the powder into each.

Example 8

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and fumaric acid was prepared as follows.

| Component | Amount per Capsule (mg) |
|---|---|
| N-[5-(3,5-difluorobenzyl)-1H-indazol-3-yl]-4-(4-methyl-piperazin-1-yl)-2-(tetrahydro-2H-pyran-4-ylamino) benzamide | 200.0 |
| Fumaric acid | 50.0 |
| Pre-gelatinized starch | 70.0 |
| Mannitol | 125.5 |
| Fumed silica | 2.25 |
| Magnesium stearate | 2.25 |
| Total | 450 |

N-[5-(3,5-difluorobenzyl)-1H-indazol-3-yl]-4-(4-methyl-piperazin-1-yl)-2-(tetrahydro-2H-pyran-4-ylamino)-benzamide was screened through 60 mesh sieve, the designated amount was weighed, and was transferred to a blend container. The fumaric acid was milled so that it flowed through a 60-mesh screen, the desired amount was weighed and was transferred to a blend container. The two components were mixed for approximately 1 minute. The pre-gelatinized starch, fumed silica, and a half portion of the mannitol were added to the blend container. The resulting mixture was blended for approximately 1 minute and was screened through a 40-mesh screen. The magnesium stearate and the remainder of the mannitol were added to a separate container, blended for approximately 1 minute, screened through a 40-mesh screen, added to the first mixture and the combined mixture was blended for about 5 minutes.

The resulting mixture was filled into #00 capsules. All capsules were filled in small-scale capsule filling trays apparatus. Capsule filling was based on volumetric filling and dependent on the tap density of the blend material. The 200 mg dose capsules were filled into size #00 capsule shells and required strong tapping of the apparatus to achieve the final fill weight.

Capsule dosage strengths of 50 mg and 100 were also prepared. The blend composition for all strengths of the capsules is the same as above, but the capsule fill weight was adjusted proportionally to achieve the required dosage strength.

The 100 mg dosage strength capsule was prepared by filling the blend described above into size #1 capsules, and the 50 mg dosage strength capsule was filled into size #3 capsules. Packing density was greatest for the 200 mg strength in size #00 capsules, and required correspondingly more tapping of the powder to fill the capsules to the desired weight. Packing density was the least for the 50 mg strength.

| Strength | Capsule Size | Fill wt. (mg) | Capsule Volume (cc) | Packing Density (g/cc) | Tapping Required for Filling |
|---|---|---|---|---|---|
| 200 mg | #00 | 450 | 0.95 | 474 | Strong |
| 100 mg | #1 | 225 | 0.5 | 450 | Medium |
| 50 mg | #3 | 112.5 | 0.3 | 375 | Slight |

Representative samples of the 200 mg capsules prepared using the procedures above were tested for drug release using the USP Apparatus Type I Basket Method under the conditions described below.

| Dissolution Parameters | |
|---|---|
| Media | 0.05M sodium acetate, adjusted to pH 4.5 |
| Volume | 500 mL |
| Stirring speed | 50 rpm |
| Bath Temperature | 37° C. |
| Apparatus | Baskets |
| Sample volume | 5 mL |
| Samples Time points | 15, 30, 45, 60, 120 minutes |
| Detection | UV at 300 nM |

Representative samples of the 200 mg capsules were tested using the conditions described above and provided the following dissolution results that represent the average percent drug release (based on measured amount of N-[5-(3,5-difluorobenzyl)-1H-indazol-3-yl]-4-(4-methyl-piperazin-1-yl)-2-(tetrahydro-2H-pyran-4-ylamino)-benzamide contained in the media compared to the total amount of N-[5-(3,5-difluorobenzyl)-1H-indazol-3-yl]-4-(4-methyl-piperazin-1-yl)-2-(tetrahydro-2H-pyran-4-ylamino)-benzamide contained in the capsules. The results below represent the average dissolution data for two capsules that were tested.

| Dissolution (%, Average of 2 Capsules prepared according to Example 8) | | | | | | |
|---|---|---|---|---|---|---|
| | Time (min) | | | | | |
| | 0 | 15 | 30 | 45 | 60 | 120 |
| % release of N-[5-(3,5-difluorobenzyl)-1H-indazol-3-yl]-4-(4-methyl-piperazin-1-yl)-2-(tetrahydro-2H-pyran-4-ylamino) benzamide from 200 mg capsules prepared according to Example 8 | 0% | 23% | 54% | 78% | 90% | 96% |

Representative 200 mg capsules prepared according to Example 11 were tested under the same dissolution conditions as above and provided the following dissolution results that represent the average percent drug release (based on measured amount of N-[5-(3,5-difluorobenzyl)-1H-indazol-3-yl]-4-(4-methyl-piperazin-1-yl)-2-(tetrahydro-2H-pyran-4-ylamino)-benzamide contained in the media compared to the total amount of N-[5-(3,5-difluorobenzyl)-1H-indazol-3-yl]-4-(4-methyl-piperazin-1-yl)-2-(tetrahydro-2H-pyran-4-ylamino)-benzamide contained in the capsules. The results below represent the average dissolution data for two capsules that were tested.

| Dissolution (%, Average of 2 Capsules prepared according to Example 11) | | | | | | |
|---|---|---|---|---|---|---|
| | Time (min) | | | | | |
| | 0 | 15 | 30 | 45 | 60 | 120 |
| % release of N-[5-(3,5-difluorobenzyl)-1H-indazol-3-yl]-4-(4-methyl-piperazin-1-yl)-2-(tetrahydro-2H-pyran-4-ylamino)-benzamide from 200 mg capsules prepared according to Example 11 | 0% | 6% | 9% | 13% | 16% | 18% |

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and at least one acidulant released a greater amount of N-[5-(3,5-difluorobenzyl)-1H-indazol-3-yl]-4-(4-methyl-piperazin-1-yl)-2-(tetrahydro-2H-pyran-4-ylamino)-benzamide into the dissolution medium under the similar conditions and at about the same measured time points as a pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide, but not comprising at least one acidulant.

Example 9

The suitability of maleic acid, fumaric acid, citric acid and tartaric acid in admixture with N-[5-(3,5-difluorobenzyl)-1H-indazol-3-yl]-4-(4-methyl-piperazin-1-yl)-2-(tetrahydro-2H-pyran-4-ylamino)-benzamide was investigated.

Dry powder mixtures of each acid in a 1:1 weight ratio with N-[5-(3,5-difluorobenzyl)-1H-indazol-3-yl]-4-(4-methyl-piperazin-1-yl)-2-(tetrahydro-2H-pyran-4-ylamino)-benzamide were prepared. The mixtures were prepared in duplicate for each sample, and stored in open top, 4 mL glass vials at (1) 60° C./dry heat and (2) 40° C. and 75% relative humidity (RH). Control samples were included which contained only N-[5-(3,5-difluorobenzyl)-1H-indazol-3-yl]-4-(4-methyl-piperazin-1-yl)-2-(tetrahydro-2H-pyran-4-ylamino)-benzamide.

After 13 days of storage it was observed that the admixtures comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric, citric, and maleic acid at the 40° C. and 75% RH condition had partially or completely liquefied. In contrast, the admixture comprising fumaric acid and N-[5-(3,5-difluorobenzyl)-1H-indazol-3-yl]-4-(4-methyl-piperazin-1-yl)-2-(tetrahydro-2H-pyran-4-ylamino)-benzamide and the control samples remained dry at 40° C. and 75% RH remained dry. All admixture samples and the control samples stored at the 60° C. and dry heat condition remained as dry powders.

The excipient compatibility samples and controls were analyzed by high-performance liquid chromatography (HPLC) after three months storage at both conditions to evaluate purity and degradation of N-[5-(3,5-difluorobenzyl)-1H-indazol-3-yl]-4-(4-methyl-piperazin-1-yl)-2-(tetrahydro-2H-pyran-4-ylamino)-benzamide. The HPLC traces analyses were conducted on an Agilent 1100 LC, equipped with Agilent Diode Array Detector and Chemstation Software using the conditions found in the table below.

| Column: | Waters SunFire ™ C18, 3.5 μm, 150 × 4.6 mm, part no. 186002554, or equivalent. |
|---|---|
| Column temp.: | 10° C. |
| Flow rate: | 1 mL/min. |
| Injection volume: | 10 μL |
| Detection wavelengths: | 303 nM for and N-[5-(3,5-difluorobenzyl)-1H-indazol-3-yl]-4-(4-methyl-piperazin-1-yl)-2-(tetrahydro-2H-pyran-4-ylamino) benzamide and related substances |
| Sample storage temp.: | Room temperature |
| Run time: | 22 minutes |
| Mobile Phases: | A: 70% water: 30% Acetonitrile, 0.1% trifluoroacetic acid (TFA) v/v<br>B: 30% water: 70% Acetonitrile, 0.1% TFA v/v |

| Gradient program | | |
|---|---|---|
| Time (min) | A (%) | B (%) |
| 0 | 90 | 10 |
| 9 | 77 | 23 |
| 14 | 32 | 68 |
| 15 | 32 | 68 |
| 15.10 | 90 | 10 |

The results as measured by HPLC are found below.

| Sample | Condition | % UV Purity | Most abundant impurity (relative retention) | Most abundant impurity (area %) |
|---|---|---|---|---|
| Tartaric Acid | 40° C./75% RH | 99.1% | 0.93 | 0.16% |
| | 60° C. Dry Heat | 99.4% | 0.84 | 0.13% |
| Citric Acid | 40° C./75% RH | 98.6% | 0.78 | 0.14% |
| | 60° C. Dry Heat | 98.3% | 0.89 | 0.45% |
| Maleic Acid | 40° C./75% RH | 44.6% | 0.83 | 51.3% |
| | 60° C. Dry Heat | 80.4% | 0.85 | 11.4% |
| Fumaric Acid | 40° C./75% RH | 98.0% | 0.85 | 1.3% |
| | 60° C. Dry Heat | 99.2% | 0.84 | 0.18% |
| Control | 40° C./75% RH | 99.2% | 0.84 | 0.13% |
| | 60° C. Dry Heat | 99.3% | 0.84 | 0.13% |

The admixture of maleic acid and N-[5-(3,5-difluorobenzyl)-1H-indazol-3-yl]-4-(4-methyl-piperazin-1-yl)-2-(tetrahydro-2H-pyran-4-ylamino)-benzamide showed poor chemical stability as degradation was observed at both storage conditions. The compatibility of N-[5-(3,5-difluorobenzyl)-1H-indazol-3-yl]-4-(4-methyl-piperazin-1-yl)-2-(tetrahydro-2H-pyran-4-ylamino)-benzamide and citric acid showed only slight increases in impurities at both storage conditions. An increase in the impurity at 0.85 RRT was seen for the fumaric acid sample (1.3% vs. 0.13% for the control) stored at the 40° C./75% RH condition, whereas the sample stored at 60° C. showed only slight increase in impurities compared to the control. The admixture of tartaric acid and N-[5-(3,5-difluorobenzyl)-1H-indazol-3-yl]-4-(4-methyl-piperazin-1-yl)-2-(tetrahydro-2H-pyran-4-ylamino)-benzamide showed excellent chemical stability with no or very little increase in impurity levels.

Although the admixture of N-[5-(3,5-difluorobenzyl)-1H-indazol-3-yl]-4-(4-methyl-piperazin-1-yl)-2-(tetrahydro-2H-pyran-4-ylamino)-benzamide and tartaric acid showed acceptable chemical stability, the admixture demonstrated unacceptable physical instability due to absorption of moisture. In contrast, the admixture of N-[5-(3,5-difluorobenzyl)-1H-indazol-3-yl]-4-(4-methyl-piperazin-1-yl)-2-(tetrahydro-2H-pyran-4-ylamino)-benzamide and fumaric acid did not demonstrate hygroscopicity and maintained and maintained an acceptable level of chemical stability.

Example 10

Hereinafter Referred to as Pharmaceutical Composition "F2"

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and fumaric acid was prepared as follows.

| Component | Amount per Capsule (mg) | Amount per batch (g) |
|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 128.00 |
| Fumaric acid, NF | 50.0 | 32.00 |
| Pre-gelatinized starch | 70.0 | 44.80 |
| Mannitol | 125.5 | 80.32 |
| Colloidal silicon dioxide, NF | 2.25 | 1.44 |
| Magnesium stearate | 2.25 | 1.44 |
| Total | 450 | 288.0 |

The N-[5-(3,5-difluorobenzyl)-1H-indazol-3-yl]-4-(4-methyl-piperazin-1-yl)-2-(tetrahydro-2H-pyran-4-ylamino)-benzamide was screened through a 60-mesh sieve and was transferred to the batch mixing container. The fumaric acid was milled in a ball mill at 30 revolutions per second for about 2 minutes, screened through a 60-mesh sieve and then transferred to the batch mixing container. The mixture of N-[5-(3,5-difluorobenzyl)-1H-indazol-3-yl]-4-(4-methyl-piperazin-1-yl)-2-(tetrahydro-2H-pyran-4-ylamino)-benzamide and fumaric acid were mixed by hand for about one minute, after which time the pre-gelatinized starch, colloidal silicon dioxide and one-half of the amount of required mannitol were added to the batch container. The resulting mixture was mixed by hand for about one minute. The magnesium stearate and mannitol were pre-blended through a 40-mesh sieve and then combined with materials in the batch mixing container. The final mixture was blended by hand for approximately 5 minutes.

The resulting mixture was filled into gelatin capsule shells, opaque white, size #00. The body and cap of the capsules were separated, the capsule bodies were placed into a capsule device, ensuring the top of the capsule body was flush with the surface of the filling device by moving the spacer of the device. The powder blend was poured onto the surface of the filling device, volumetrically filling the body of the capsules, and scraping the excess powder evenly until all capsule bodies are filled. The powder was firmly tamped into the shells one time using a tamper. Additional powder blend was added to fill the remainder of the capsule and any excess powder was scraped off. The tamping, filling, and scraping procedures were repeated for each capsule until the desired capsule fill weight was achieved. The filled capsules were collected in a 10-mesh sieve and were de-dusted by agitating them lightly.

The filled capsule weight range acceptance limits were set at 93% to 107%. The average weight of the empty capsule shells was 119.4 mg. The low capsule weight limit was set at (0.93×450 mg)+119.4 mg=538 mg. The high capsule weight limit was set at (1.07×450 mg)+119.4 mg=601 mg. Only those capsules meeting the weight limits were used in the study described in Example 12.

Example 11

Hereinafter Referred to as Pharmaceutical Composition "F1"

Hard gelatin capsules comprising 50 mg, 100 mg, and 200 mg of N-[5-(3,5-difluorobenzyl)-1H-indazol-3-yl]-4-(4-methyl-piperazin-1-yl)-2-(tetrahydro-2H-pyran-4-ylamino)-benzamide, but not comprising at least one acidulant, are prepared as follows.

The required amounts of active ingredient and excipients are weighed into the warehouse dispensing area. The weight of N-[5-(3,5-difluorobenzyl)-1H-indazol-3-yl]-4-(4-methyl-piperazin-1-yl)-2-(tetrahydro-2H-pyran-4-ylamino)-benzamide and the mannitol are adjusted according to the active desired potency of the dosage form. (1) Manually pre-mix N-[5-(3,5-difluorobenzyl)-1H-indazol-3-yl]-4-(4-methyl-piperazin-1-yl)-2-(tetrahydro-2H-pyran-4-ylamino)-benzamide and colloidal silicon dioxide into a polyethylene (PE) bag. (2) The resulting mixture from step 1 is passed through a 0.500 mm screen size sieve, along with a portion of the pregelatinized starch and mannitol and the resulting materials are collected in a blender. (3) The resulting mixture from step 2 is further mixed for about 20 minutes at 20-25 rpm. (4) The pregelatinized starch and magnesium stearate and are pre-mixed together and are passed through a 0.500 mm screen size sieve. (5) The material from step 4 are mixed together with the materials from step 3 and mixed for about 20 minutes at 20-25 rpm. (6) The blend resulting from step 5 is filled into hard gelatin capsules using an automatic capsule filling machine. Representative formulations of capsules comprising 50 mg, 100 mg or 200 mg of N-[5-(3,5-difluorobenzyl)-1H-indazol-3-yl]-4-(4-methyl-piperazin-1-yl)-2-(tetrahydro-2H-pyran-4-ylamino)-benzamide are shown below.

50 mg capsule representative batch formulation (50 mg F1)

| Components | Function | Batch formula 50 mg (6,000 capsules) | Amount per capsule 50 mg |
|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | Active ingredient | 300 g | 50 mg |
| Mannitol | Filler | 255.00 g | 42.50 mg |
| Pregelatinized starch | Filler | 102.75 g | 17.125 mg |
| Colloidal silicon dioxide | Glidant | 10.50 g | 1.750 mg |
| Magnesium stearate | Lubricant | 6.75 g | 1.125 mg |
| Total | | 675.00 g | 112.50 mg |

100 mg capsule representative batch formulation (100 mg F1)

| Components | Function | Batch formula 100 mg (3,600 capsules) | Amount per capsule 100 mg |
|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | Active ingredient | 360.0 g | 100.00 mg |
| Mannitol | Filler | 306.00 g | 85.00 mg |
| Pregelatinized starch | Filler | 123.30 g | 34.25 mg |
| Colloidal silicon dioxide | Glidant | 12.60 g | 3.50 mg |
| Magnesium stearate | Lubricant | 8.10 g | 2.25 mg |
| Total | | 810.00 g | 225.00 mg |

| 200 mg capsule representative batch formulation (200 mg F1) | | | |
|---|---|---|---|
| Components | Function | Batch formula 200 mg (4,100 capsules) | Amount per capsule 200 mg |
| N-[5-(3,5-difluorobenzyl)-1H-indazol-3-yl]-4-(4-methyl-piperazin-1-yl)-2-(tetrahydro-2H-pyran-4-ylamino)-benzamide | Active ingredient | 820.00 g | 200.00 mg |
| Mannitol | Filler | 697.00 g | 170.00 mg |
| Pregelatinized starch | Filler | 280.85 g | 68.50 mg |
| Colloidal silicon dioxide | Glidant | 28.70 g | 7.00 mg |
| Magnesium stearate | Lubricant | 18.45 g | 4.50 mg |
| Total | | 1845.00 g | 450.00 mg |

Example 12

Comparative Pharmacokinetic Study of F1 and F2 Formulations

A comparative pharmacokinetic study in healthy, human subjects was conducted comparing a 200 mg dosage strength of pharmaceutical composition F1 (as described in Example 11) with a 200 mg dosage strength pharmaceutical composition F2 (as described in Example 10).

Pharmaceutical compositions F1 and F2, along with and lansoprazole, were administered orally with approximately 240 mL of water, according to the randomization scheme. Lansoprazole was administered as 30 mg lansoprazole delayed-release capsules.

Subjects were randomized into two groups, A and B. Periods 1 and 2 were conducted as a crossover design under fasting conditions where all subjects received F1 and F2. In Period 3, subjects received the same N-[5-(3,5-difluorobenzyl)-1H-indazol-3-yl]-4-(4-methyl-piperazin-1-yl)-2-(tetrahydro-2H-pyran-4-ylamino)-benzamide formulation as they received in Period 2, but under fed conditions. A representative summary of Periods 1, 2, and 3 and the pharmaceutical compositions subjects in groups A and B will receive in each Period is found below.

| Subject Group | Period 1 (fasted) | Period 2 (fasted) | Period 3 (fed) |
|---|---|---|---|
| A | F1 | F2 | F2 |
| B | F2 | F1 | F1 |

In each period, multiple oral daily doses of lansoprazole were administered for 9 consecutive days with a single oral dose of N-[5-(3,5-difluorobenzyl)-1H-indazol-3-yl]-4-(4-methyl-piperazin-1-yl)-2-(tetrahydro-2H-pyran-4-ylamino)-benzamide administered concomitantly on Day 4 under fasting (Periods 1 and 2) or fed (Period 3) conditions. PK sampling for N-[5-(3,5-difluorobenzyl)-1H-indazol-3-yl]-4-(4-methyl-piperazin-1-yl)-2-(tetrahydro-2H-pyran-4-ylamino)-benzamide and its metabolite, M5, was conducted for 120 hours following N-[5-(3,5-difluorobenzyl)-1H-indazol-3-yl]-4-(4-methyl-piperazin-1-yl)-2-(tetrahydro-2H-pyran-4-ylamino)-benzamide administration.

The washout period was at least 8 days between each dose of N-[5-(3,5-difluorobenzyl)-1H-indazol-3-yl]-4-(4-methyl-piperazin-1-yl)-2-(tetrahydro-2H-pyran-4-ylamino)-benzamide.

In order to ensure a full panel of subjects (up to 24 subjects in each study part), prior to N-[5-(3,5-difluorobenzyl)-1H-indazol-3-yl]-4-(4-methyl-piperazin-1-yl)-2-(tetrahydro-2H-pyran-4-ylamino)-benzamide dosing on day 4, subjects, including standbys (3 replacement subjects in each dosing group to account for possible dropouts following the safety evaluations on day 3) received a dose of lansoprazole on days 1 to 3. Lansoprazole administration on days 1 to 9 was conducted in the morning, approximately 1.5 hours prior to administration of either F1 or F2 at hour 0 on day 4.

Subjects were randomized and received 3 out of 4 treatments in one of the following sequences: ABD or BAC (i.e., Periods 1 and 2 were conducted as a crossover design under fasting conditions [Treatments A and B]). In Period 3, subjects received the same N-[5-(3,5-difluorobenzyl)-1H-indazol-3-yl]-4-(4-methyl-piperazin-1-yl)-2-(tetrahydro-2H-pyran-4-ylamino)-benzamide formulation as they received in Period 2, but under fed conditions [Treatment C or D]). Each subject received each of the 3 assigned treatments on one occasion.

Treatments A and C utilized 200 mg strength F1 capsules.
Treatments B and D utilized 200 mg F2 capsules.
Treatments A, B, C, and D were as follows:

Treatment A: 30 mg lansoprazole (1×30 mg capsule), for 9 consecutive days (within ±1 hour of dosing time on Day 1), with 800 mg F1 (4×200 mg capsules) administered under fasting conditions 1.5 hours after administration of lansoprazole on Day 4.

Treatment B: 30 mg lansoprazole (1×30 mg capsule), for 9 consecutive days (within ±1 hour of dosing time on Day 1), with 800 mg F2 (4×200 mg capsules) administered under fasting conditions 1.5 hours after administration of lansoprazole on Day 4.

Treatment C: 30 mg lansoprazole (1×30 mg capsule), for 9 consecutive days (within ±1 hour of dosing time on Day 1), with 800 mg F1 (4×200 mg capsules) administered 30 minutes after the start of a high-fat breakfast on Day 4. On Day 4, lansoprazole was administered approximately 1 hour prior to the start of the high-fat meal.

Treatment D: 30 mg lansoprazole (1×30 mg capsule) following an overnight fast, for 9 days (within ±1 hour of dosing time on Day 1), with 800 mg F2 (4×200 mg capsules) administered 30 minutes after the start of a high-fat breakfast on Day 4. On Day 4, lansoprazole was administered approximately 1 hour prior to the start of the high-fat meal.

For all procedures scheduled post-N-[5-(3,5-difluorobenzyl)-1H-indazol-3-yl]-4-(4-methyl-piperazin-1-yl)-2-(tetrahydro-2H-pyran-4-ylamino) benzamide dosing, time points were relative to the time of N-[5-(3,5-difluorobenzyl)-1H-indazol-3-yl]-4-(4-methyl-piperazin-1-yl)-2-(tetrahydro-2H-pyran-4-ylamino)-benzamide dosing (i.e., Hour 0 on Day 4).

For all subjects, blood samples were collected in blood collection tubes containing sodium heparin at scheduled time points. Sampling time-points were relative to the time of N-[5-(3,5-difluorobenzyl)-1H-indazol-3-yl]-4-(4-methyl-piperazin-1-yl)-2-(tetrahydro-2H-pyran-4-ylamino)-benzamide dosing (i.e., Hour 0 on Day 4). Blood sampling for pharmacokinetic measurements were scheduled for the following times (in hours) (all time points were measured as relative to N-[5-(3,5-difluorobenzyl)-1H-indazol-3-yl]-4-(4-methyl-piperazin-1-yl)-2-(tetrahydro-2H-pyran-4-ylamino)-benzamide dosing, i.e., hour 0 on day 4 of the study): 0, 0.5, 1, 2, 3, 4, 5, 6, 8, 12, 24, 36, 48, 72, 96, and 120.

Subject plasma samples were analyzed for the presence of N-[5-(3,5-difluorobenzyl)-1H-indazol-3-yl]-4-(4-methyl-piperazin-1-yl)-2-(tetrahydro-2H-pyran-4-ylamino)-benzamide and a metabolite of N-[5-(3,5-difluorobenzyl)-1H-indazol-3-yl]-4-(4-methyl-piperazin-1-yl)-2-(tetrahydro-2H-pyran-4-ylamino)-benzamide using analytical methods known to those of ordinary skill in the art.

All subjects who received at least one dose of N-[5-(3,5-difluorobenzyl)-1H-indazol-3-yl]-4-(4-methyl-piperazin-1-yl)-2-(tetrahydro-2H-pyran-4-ylamino)-benzamide and had evaluable PK data made up the PK Population and was used for all PK analyses. The following PK parameters were calculated for N-[5-(3,5-difluorobenzyl)-1H-indazol-3-yl]-4-(4-methyl-piperazin-1-yl)-2-(tetrahydro-2H-pyran-4-ylamino)-benzamide in plasma, as appropriate: $AUC_{0-t}$, $AUC_{0-inf}$, AUC % extrap, $C_{max}$, $T_{max}$, t½, CL/F, and Vz/F.

The PK parameters $AUC_{0-t}$, $AUC_{0-inf}$ and $C_{max}$ for N-[5-(3,5-difluorobenzyl)-1H-indazol-3-yl]-4-(4-methyl-piperazin-1-yl)-2-(tetrahydro-2H-pyran-4-ylamino)-benzamide were analyzed using analysis of variance (ANOVA) model to calculate the geometric least squares mean (LSM) ratio using natural log-transformed data. A 90% confidence interval (CI) was constructed around the ratio of the geometric mean for the three PK parameters for N-[5-(3,5-difluorobenzyl)-1H-indazol-3-yl]-4-(4-methyl-piperazin-1-yl)-2-(tetrahydro-2H-pyran-4-ylamino)-benzamide.

Formulation F1 was used as the reference for all relative bioavailability analysis. Fasted dosing was used as the reference for food effect analysis. The following assessments were done: (1) the relative bioavailability of N-[5-(3,5-difluorobenzyl)-1H-indazol-3-yl]-4-(4-methyl-piperazin-1-yl)-2-(tetrahydro-2H-pyran-4-ylamino)-benzamide in two formulations under fasting conditions were evaluated by comparing Treatment B versus Treatment A; and (2) the effect of food on each of the two N-[5-(3,5-difluorobenzyl)-1H-indazol-3-yl]-4-(4-methyl-piperazin-1-yl)-2-(tetrahydro-2H-pyran-4-ylamino)-benzamide formulations F1 and F2, were evaluated by comparing (a) for F1, Treatment C versus Treatment A (within the same treatment sequence), and (b) for F2, Treatment D versus Treatment B (within the same treatment sequence).

The results of the study are shown in the tables below. All values, except $T_{max}$, are reported as the mean value (% CV). The $T_{max}$ values are reported as the median value and the range. For example, for formulation F1, the median $T_{max}$ for 23 subjects in the fasted state was about 5 hours, with a range of about 2 hours to about 8 hours.

Additional analysis was conducted to evaluate fixed dosing by body weight, or adjusted dosing based on body surface area. At 800 mg fixed dose, a total of 23 healthy subjects were evaluated with body weights ranging from 55 to 106 kg (median 74 kg) and BSA ranging from 1.57 to 2.28 mg/m² (median 1.79 mg/m²). Total exposure of N-[5-(3,5-difluorobenzyl)-1H-indazol-3-yl]-4-(4-methyl-piperazin-1-yl)-2-(tetrahydro-2H-pyran-4-ylamino)-benzamide did not correlate with body weight or body surface area, suggesting the viability of fixed dosing.

Example 13

Referred to Herein as "F2A"

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride was prepared as follows.

| Component | Target amount per dosage unit (mg) | Target weight per batch (g) | Actual weight per batch (g) |
|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 222.22 | 222.23 |
| Betaine hydrochloride | 82.00 | 91.11 | 91.11 |
| Isomalt | 124.00 | 137.78 | 137.78 |
| Pregelatinized starch, NF (Starch 1500) | 35.00 | 38.89 | 38.89 |
| Colloidal silicon dioxide | 4.50 | 5.00 | 5.00 |
| Magnesium stearate, NF | 4.50 | 5.00 | 5.00 |
| Total | 450.00 | 500.00 | 500.01 |

The N-[5-(3,5-difluorobenzyl)-1H-indazol-3-yl]-4-(4-methyl-piperazin-1-yl)-2-(tetrahydro-2H-pyran-4-ylamino)-benzamide was screened through a 60-mesh sieve and was transferred to the batch mixing container. The betaine hydrochloride was ground with a mortar and pestle, screened through a 60-mesh sieve and then transferred to the batch mixing container. The mixture of N-[5-(3,5-difluorobenzyl)-1H-indazol-3-yl]-4-(4-methyl-piperazin-1-yl)-2-(tetrahydro-2H-pyran-4-ylamino)-benzamide and betaine hydrochloride were mixed by hand for about one minute, after

| | | | | Formulation F1 | | | | | | Formulation F2 | | | | |
|---|---|---|---|---|---|---|---|---|---|---|---|---|---|---|
| Period | Food | | N | $T_{max}$* (hr) | $C_{max}$ (nM) | $AUC_{0-24}$ (nM·hr) | $AUC_\infty$ (nM·hr) | $t_{1/2}$ (hr) | N | $T_{max}$* (hr) | $C_{max}$ (nM) | $AUC_{0-24}$ (nM·hr) | $AUC_\infty$ (nM·hr) | $t_{1/2}$ (hr) |
| 1 & 2 | Fasted | Mean | 23 | 5 | 623 | 9390 | 26700 | 29.7 | 24 | 5 | 2110 | 28900 | 59600 | 25.2 |
| | | CV % | | (2-8) | 107 | 118 | 108 | 67.9 | | (2-6) | 24 | 24.3 | 31.3 | 29.8 |

| | | | | Formulation F1 | | | | | | Formulation F2 | | | | |
|---|---|---|---|---|---|---|---|---|---|---|---|---|---|---|
| Period | Food | | N | $T_{max}$* (hr) | $C_{max}$ (nM) | $AUC_{0-24}$ (nM·hr) | $AUC_\infty$ (nM·hr) | $t_{1/2}$ (hr) | N | $T_{max}$* (hr) | $C_{max}$ (nM) | $AUC_{0-24}$ (nM·hr) | $AUC_\infty$ (nM·hr) | $t_{1/2}$ (hr) |
| 2 | Fasted | Mean | 11 | 5 | 637 | 8760 | 26600 | 33.1 | 12 | 5 | 2080 | 30800 | 68800 | 29.2 |
| | | CV % | | (2-8) | 84.8 | 89.2 | 84.6 | 86.4 | | (4-6) | 21.4 | 21.7 | 27.9 | 17.9 |
| 3 | Fed | Mean | 11 | 8 | 2550 | 37300 | 88600 | 28.1 | 12 | 8 | 2560 | 40400 | 102000 | 27 |
| | | CV % | | (5-12) | 35.5 | 30 | 32.6 | 26.8 | | (5-12) | 20.1 | 19.5 | 28.3 | 16.6 | which time the pre-gelatinized starch, colloidal silicon dioxide and one-half of the amount of required isomalt were added to the batch container. The resulting mixture was mixed by hand for about one minute. The magnesium stearate and the remaining isomalt were pre-blended through a 40-mesh sieve and then combined with materials in the batch mixing container. The final mixture was blended by hand for approximately 5 minutes.

The resulting mixture was filled into gelatin capsule shells, opaque white, size #00. The body and cap of the capsules were separated, the capsule bodies were placed into a capsule device, ensuring the top of the capsule body was flush with the surface of the filling device by moving the spacer of the device. The powder blend was poured onto the surface of the filling device, volumetrically filling the body of the capsules, and scraping the excess powder evenly until all capsule bodies are filled. The powder was firmly tamped into the shells one time using a tamper. Additional powder blend was added to fill the remainder of the capsule and any excess powder was scraped off. The tamping, filling, and scraping procedures were repeated for each capsule until the desired capsule fill weight was achieved. The filled capsules were collected in a 10-mesh sieve and were de-dusted by agitating them lightly.

The filled capsule weight range acceptance limits were set at 93% to 107%. The average weight of the empty capsule shells was 119.4 mg. The low capsule weight limit was set at (0.93×450 mg)+119.4 mg=538 mg. The high capsule weight limit was set at (1.07×450 mg)+119.4 mg=601 mg. Only those capsules meeting the weight limits were used in subsequent studies.

Example 14

Comparative Pharmacokinetic Study of F2A

A comparative pharmacokinetic study in healthy, human subjects was conducted comparing a single dose of F2A with or without the PPI lansoprazole to determine the effects, if any, of the PPI.

Pharmaceutical composition F2A was administered orally at a dosage of 800 mg (four 200 mg F2A capsules) with approximately 240 mL of water to healthy individuals under fasted conditions. Subjects were randomized into two groups, E and F. Periods 1 and 2 were conducted as a crossover design under fasting conditions where all subjects received F2A under fasted conditions, but in Period 1 Group A was administered of lansoprazole and Group B was not administered lansoprazole. In Period 2, Group A was not administered lansoprazole and Group B was administered lansoprazole. In Period 3, the subjects continued the same treatment from Period 2, but under fed conditions. A representative summary of Periods 1, 2, and 3 and the pharmaceutical compositions subjects in groups A and B will receive in each Period is found below.

Subjects were randomized and received 3 out of 4 treatments in one of the following sequences: EFH or FEG (i.e., Periods 1 and 2 were conducted as a crossover design under fasting conditions [Treatments E and F]). In Period 3, subjects received the same N-[5-(3,5-difluorobenzyl)-1H-indazol-3-yl]-4-(4-methyl-piperazin-1-yl)-2-(tetrahydro-2H-pyran-4-ylamino)-benzamide formulation as they received in Period 2, but under fed conditions [Treatment G or H]). Each subject received each of the 3 assigned treatments on one occasion.

Treatment E: 800 mg of F2A (4×200 mg capsules) under fasting conditions on Day 4.

Treatment F: 30 mg lansoprazole (1×30 mg capsule) for 8 consecutive days (within ±1 hour of dosing time on Day 1), with 800 mg F2A (4×200 mg capsules) administered under fasting conditions 1.5 hours after administration of lansoprazole on Day 4.

Treatment G: 800 mg F2A (4×200 mg capsules) administered 30 minutes after the start of a high-fat breakfast on Day 4.

Treatment H: 30 mg lansoprazole (1×30 mg capsule) for 9 consecutive days (within ±1 hour of dosing time on Day 1), with 800 mg F2A (4×200 mg capsules) administered 30 minutes after the start of a high-fat breakfast on Day 4. On Day 4, lansoprazole is administered approximately 1 hour prior to the start of the high-fat meal.

| Subject Group | Period 1 (fasted) | Period 2 (fasted) | Period 3 (fed) |
|---|---|---|---|
| E | F2A no lansoprazole | F2A w/lansoprazole | F2A w/lansoprazole |
| F | F2A w/lansoprazole | F2A no lansoprazole | F2A no lansoproazole |

In each period, up to 12 of the 24 subjects received doses of lansoprazole, which were administered to determine the effect of the PPI based on the above scheme with a single oral dose of N-[5-(3,5-difluorobenzyl)-1H-indazol-3-yl]-4-(4-methyl-piperazin-1-yl)-2-(tetrahydro-2H-pyran-4-ylamino)-benzamide administered concomitantly on Day 4 of each period either under fasting (Periods 1 and 2) or fed (Period 3) conditions. Plasma pharmacokinetic sampling for N-[5-(3,5-difluorobenzyl)-1H-indazol-3-yl]-4-(4-methyl-piperazin-1-yl)-2-(tetrahydro-2H-pyran-4-ylamino)-benzamide and its metabolite, M5, was conducted for 120 hours following N-[5-(3,5-difluorobenzyl)-1H-indazol-3-yl]-4-(4-methyl-piperazin-1-yl)-2-(tetrahydro-2H-pyran-4-ylamino)-benzamide administration.

The washout period was at least 8 days between each dose of N-[5-(3,5-difluorobenzyl)-1H-indazol-3-yl]-4-(4-methyl-piperazin-1-yl)-2-(tetrahydro-2H-pyran-4-ylamino)-benzamide.

The washout period was at least 8 days between each dose of N-[5-(3,5-difluorobenzyl)-1H-indazol-3-yl]-4-(4-methyl-piperazin-1-yl)-2-(tetrahydro-2H-pyran-4-ylamino)-benzamide.

For all procedures scheduled post-N-[5-(3,5-difluorobenzyl)-1H-indazol-3-yl]-4-(4-methyl-piperazin-1-yl)-2-(tetrahydro-2H-pyran-4-ylamino) benzamide dosing, time points were relative to the time of N-[5-(3,5-difluorobenzyl)-1H-indazol-3-yl]-4-(4-methyl-piperazin-1-yl)-2-(tetrahydro-2H-pyran-4-ylamino)-benzamide dosing (i.e., Hour 0 on Day 4).

For all subjects, 16 mg ondansetron is administered without water on Day 4 of each period prior to N-[5-(3,5-difluorobenzyl)-1H-indazol-3-yl]-4-(4-methyl-piperazin-1-yl)-2-(tetrahydro-2H-pyran-4-ylamino) benzamide dosing, as a prophylactic antiemetic measure.

For all subjects, blood samples were collected in blood collection tubes containing sodium heparin at scheduled time points. Sampling time-points were relative to the time of N-[5-(3,5-difluorobenzyl)-1H-indazol-3-yl]-4-(4-methyl-piperazin-1-yl)-2-(tetrahydro-2H-pyran-4-ylamino)-benzamide dosing (i.e., Hour 0 on Day 4). Blood sampling for pharmacokinetic measurements were scheduled for the following times (in hours) (all time points were measured as relative to N-[5-(3,5-difluorobenzyl)-1H-indazol-3-yl]-4-(4-methyl-piperazin-1-yl)-2-(tetrahydro-2H-pyran-4-ylamino)- benzamide dosing, i.e., hour 0 on day 4 of the study): 0, 0.5, 1, 2, 3, 4, 5, 6, 8, 12, 24, 36, 48, 72, 96, and 120.

Subject plasma samples were analyzed for the presence of N-[5-(3,5-difluorobenzyl)-1H-indazol-3-yl]-4-(4-methyl-piperazin-1-yl)-2-(tetrahydro-2H-pyran-4-ylamino)-benzamide and a metabolite of N-[5-(3,5-difluorobenzyl)-1H-indazol-3-yl]-4-(4-methyl-piperazin-1-yl)-2-(tetrahydro-2H-pyran-4-ylamino)-benzamide using analytical methods known to those of ordinary skill in the art.

All subjects who received at least one dose of N-[5-(3,5-difluorobenzyl)-1H-indazol-3-yl]-4-(4-methyl-piperazin-1-yl)-2-(tetrahydro-2H-pyran-4-ylamino)-benzamide and had evaluable PK data made up the PK Population and was used for all PK analyses. The following PK parameters were calculated for N-[5-(3,5-difluorobenzyl)-1H-indazol-3-yl]-4-(4-methyl-piperazin-1-yl)-2-(tetrahydro-2H-pyran-4-ylamino)-benzamide in plasma, as appropriate: $AUC_{0-t}$, $AUC_{0-inf}$, AUC % extrap, $C_{max}$, $T_{max}$, $t_{1/2}$, CL/F, and Vz/F.

The PK parameters $AUC_{0-t}$, $AUC_{0-inf}$, and $C_{max}$ for N-[5-(3,5-difluorobenzyl)-1H-indazol-3-yl]-4-(4-methyl-piperazin-1-yl)-2-(tetrahydro-2H-pyran-4-ylamino)-benzamide were analyzed using analysis of variance (ANOVA) model to calculate the geometric least squares mean (LSM) ratio using natural log-transformed data. A 90% confidence interval (CI) was constructed around the ratio of the geometric mean for the three PK parameters for N-[5-(3,5-difluorobenzyl)-1H-indazol-3-yl]-4-(4-methyl-piperazin-1-yl)-2-(tetrahydro-2H-pyran-4-ylamino)-benzamide. Formulation 2A was used as the reference for all relative bioavailability analysis.

The results of the study are shown in the tables below. All values, except $T_{max}$, are reported as the mean value (% CV). The $T_{max}$ values are reported as the median value and the range.

| Dose | N | | $T_{max}$ | $C_{max}$ | $AUC_\infty$ |
|------|---|---|-----------|-----------|--------------|
| No PPI | 22 | Mean | 4.0 | 2670 | 66000 |
|        |    | % CV | (2-5) | 24.0 | 28.8 |
| W PPI  | 22 | Mean | 4.5 | 1500 | 39400 |
|        |    | % CV | (3-6) | 30.7 | 35.2 |

Following a single dose of F2A at 800 mg (4×200 mg F2A capsules) to healthy subjects under fasted conditions, F2A was readily absorbed, with detectable F2A in circulation at 0.5 hr post-dose and reaching median $T_{max}$ at 4.5 hr with lansoprazole, and 5 hr without lansoprazole. Mean terminal half-life ($t_{1/2}$) was approximately 24 hours, supporting a once daily dosing regimen. FIG. 1 depicts a graphical illustration comparing the effect of lansoprazole. As seen in FIG. 1, and as shown in the table above, a clear PPI effect is observed when using F2A with lansoprazole under fasted conditions, where the $AUC_\infty$ is approximately 67% higher without lansoprazole.

In addition to comparing the effects of lansoprazole, the above study was used to determine the effect of food with F2A treatment by comparing Period 2 with Period 3 for each treatment group. Group A received no lansoprazole under fasting conditions in Period 2, and no lansoprazole under fed conditions in Period 3. The table below shows the food effect without lansoprazole. See also FIG. 2 and FIG. 3.

| | % CV Comparison | | Average $AUC_\infty$ | |
|---|---|---|---|---|
| | No PPI | PPI | No PPI | PPI |
| Fasted | 24 | 32 | 61600 | 44300 |
| Fed | 32 | 32 | 82800 | 95800 |

Figure 2:
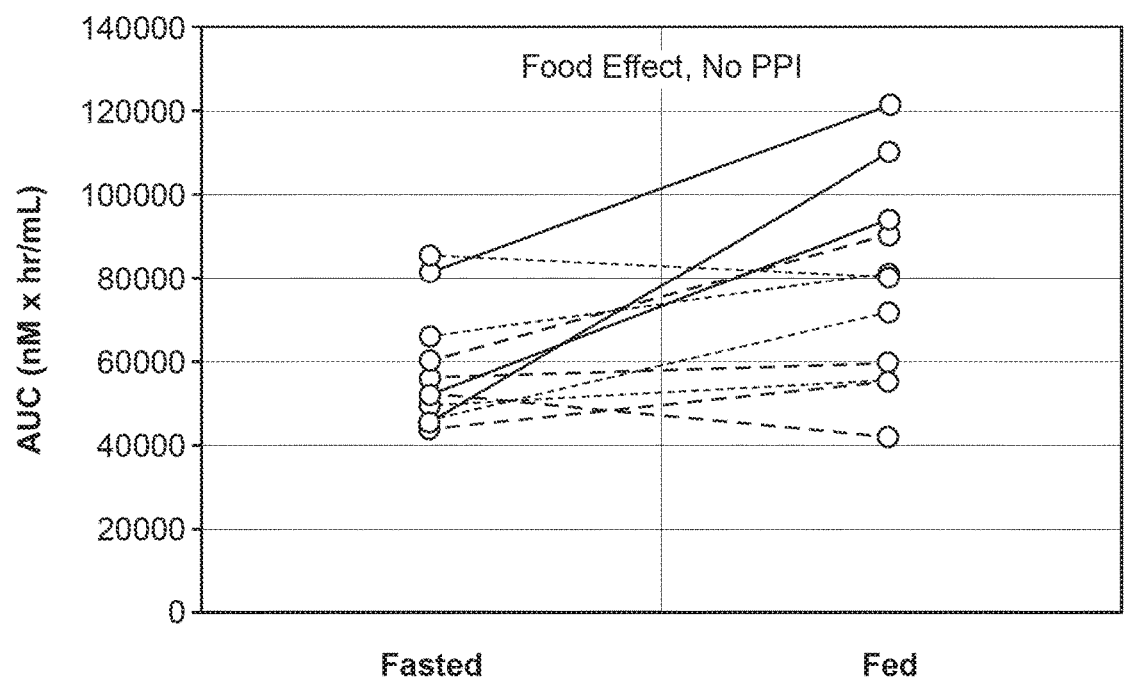
FIG. 2 is a graphical illustration of the effect of food on bioavailability (area under the curve, AUC) of N-[5-(3,5-difluorobenzyl)-1H-indazol-3-yl]-4-(4-methyl-piperazin-1-yl)-2-(tetrahydro-pyran-4-ylamino)-benzamide, measured in nM*hr/mL. The F2A formulation was administered under fed or fasted conditions without a PPI.

The data indicate that when F2A is administered without lansoprazole, the $AUC_\infty$ is approximately 25% higher under fed conditions compared to fasted conditions. In addition, the individual difference of $AUC_\infty$ was up to 2.5 times greater under fed conditions compared to fasted conditions (FIG. 2).

The effect of PPI co-administration was also evaluated for the F2A formulation. Mean steady-state exposure of F2A was approximately 40% lower in subjects were co-administered a PPI, compared to subjects administered F2A alone. The table below summarizes the effect of co-administration of PPI on F2A exposure in healthy subjects under fasted conditions.

| | | GeoLSM | | Geomean Ratio (%) | CI90% | |
|---|---|---|---|---|---|---|
| Parameter | N | w PPI | no PPI | (w PPI/no PPI) | Lower | Upper |
| $C_{max}$ (nm) | 22 | 1439 | 2609 | 55 | 49 | 62 |
| $AUC_{inf}$ (nM · hr) | 22 | 37498 | 62972 | 60 | 52 | 68 |

The food effect was also evaluated for the F2A formulation, both with and without co-administration of a PPI. Without PPI, minimal food effect was observed, with a fed/fasted geometric mean ratio of 131%. With co-administration of a PPI, a higher fed/fasted geometric mean ratio of 213% was observed. However, the difference in food effect was significantly reduced compared to a similar study of the F1 formulation (~4×) as summarized in the table below.

| PPI | Parameter | N | GeoLSM Fed | Fasted | Geomean Ratio (%) (Fed/Fasted) | CI90% Lower | Upper |
|---|---|---|---|---|---|---|---|
| No PPI | $C_{max}$ (nm) | 12 | 2468 | 2477 | 100 | 88.1 | 114 |
|        | $AUC_{inf}$ (nM · hr) | 12 | 79019 | 60113 | 131 | 108 | 160 |
| W PPI  | $C_{max}$ (nm) | 9 | 2199 | 1480 | 149 | 122 | 180 |
|        | $AUC_{inf}$ (nM · hr) | 9 | 91392 | 42457 | 215 | 169 | 269 |

In summary, formulation F2A greatly reduced the inter-subject variability and food effect compared to formulation F1. In addition, co-administration of a PPI with formulation F2A results in a 40% reduction of F2A exposure.

Figure 3:
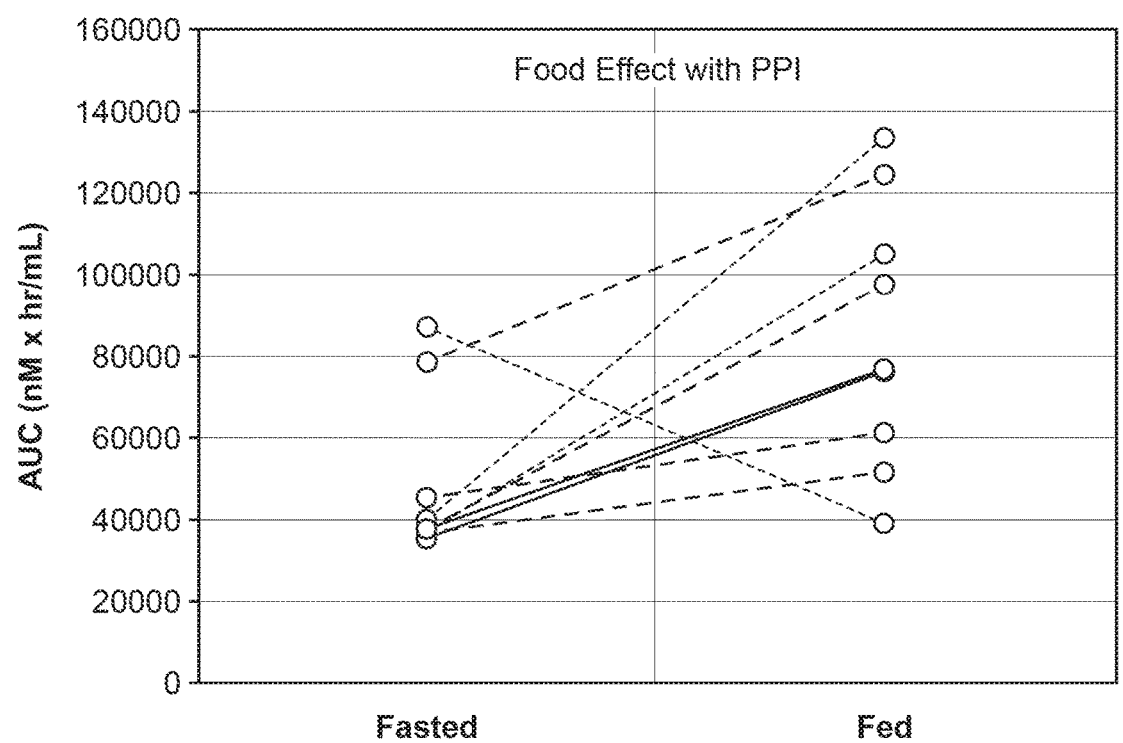
FIG. 3 is a graphical illustration of the effect of food on bioavailability (area under the curve, AUC) of N-[5-(3,5-difluorobenzyl)-1H-indazol-3-yl]-4-(4-methyl-piperazin-1-yl)-2-(tetrahydro-pyran-4-ylamino)-benzamide, measured in nM*hr/mL. The F2A formulation was administered under fed or fasted conditions with a PPI.

The data also show that when F2A is administered with lansoprazole, the $AUC_\infty$ is approximately 80% greater under fed conditions compared to fasted conditions. The individual difference of $AUC_\infty$ can be up to 3 times greater in fed conditions compared to fasted conditions, as is shown in FIG. 3.

The full results of the study are shown in the tables below. All values, except $T_{max}$, are reported as the mean value (% CV). The $T_{max}$ values are reported as the median value and the range.

| | | | | Formulation F2A without PPI | | | | | | Formulation F2A with PPI | | | | |
|---|---|---|---|---|---|---|---|---|---|---|---|---|---|---|
| Period | Food | | N | $T_{max}$* (hr) | $C_{max}$ (nM) | $AUC_{0-24}$ (nM · hr) | $AUC_\infty$ (nM · hr) | $t_{1/2}$ (hr) | N | $T_{max}$* (hr) | $C_{max}$ (nM) | $AUC_{0-24}$ (nM · hr) | $AUC_\infty$ (nM · hr) | $t_{1/2}$ (hr) |
| 1 | Fasted | Mean | 10 | 3.5 | 2860 | 38300 | 71400 | 23.7 | 12 | 3.0 | 1490 | 19000 | 35200 | 23.1 |
| | | CV % | | (2-5) | 28.8 | 27.3 | 32.1 | 15.5 | | (3-5) | 36.1 | 32.5 | 36.4 | 20.6 |
| 2 | Fasted | Mean | 12 | 4.0 | 2510 | 34300 | 61600 | 23.2 | 10 | 5.0 | 1520 | 22200 | 44300 | 24.5 |
| | | CV % | | (3-5) | 16.2 | 17.1 | 23.8 | 12.1 | | (3-6) | 24.8 | 26.2 | 31.6 | 18.8 |
| 1 & 2 | Fasted | Mean | 22 | 4.0 | 2670 | 36100 | 66000 | 23.4 | 22 | 4.5 | 1500 | 20400 | 39400 | 23.8 |
| | | CV % | | (2-5) | 24.0 | 23.0 | 28.8 | 13.5 | | (3-6) | 30.7 | 29.8 | 35.2 | 19.5 |

| | | | | Formulation F2A | | | | |
|---|---|---|---|---|---|---|---|---|
| Period | Food | | N | $T_{max}$* (hr) | $C_{max}$ (nM) | $AUC_{0-24}$ (nM · hr) | $AUC_\infty$ (nM · hr) | $t_{1/2}$ (hr) |
| 2 | Fasted | Mean | 10 | 5.0 | 1520 | 22200 | 44300 | 24.5 |
| | | CV % | | (3-6) | 24.8 | 26.2 | 31.6 | 18.8 |
| 3 | Fed | Mean | 11 | 12 | 2270 | 36600 | 95800 | 28.1 |
| | | CV % | | (8-12) | 26.6 | 30 | 31.8 | 26.8 |

Figure 4:
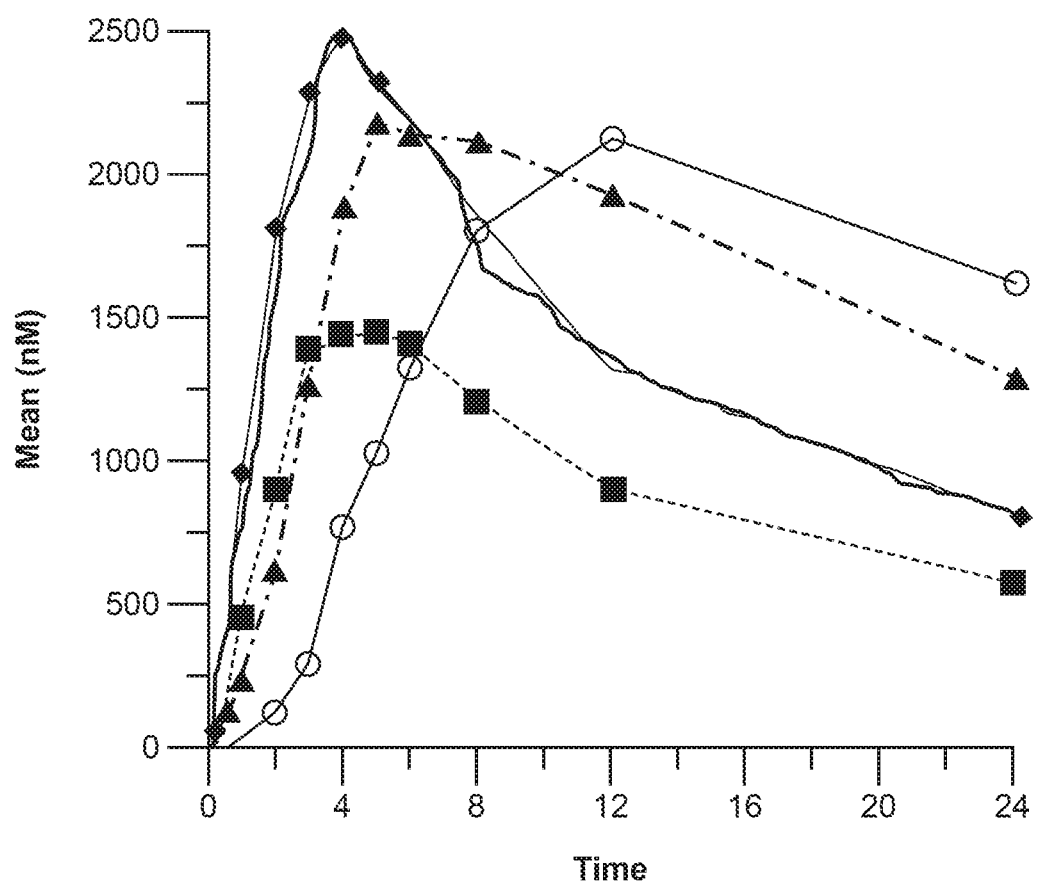
FIG. 4 is a graphical illustration of the mean plasma levels (in nanomolar) over time of N-[5-(3,5-difluorobenzyl)-1H-indazol-3-yl]-4-(4-methyl-piperazin-1-yl)-2-(tetrahydro-pyran-4-ylamino)-benzamide after treatment with F2A. Diamonds (♦) indicate administration of F2A under fasting conditions without a PPI. Squares (■) indicate administration of F2A under fasted conditions with a PPI. Triangles (▲) indicate administration of F2A under fed conditions without a PPI. Circles (○) indicate administration of F2A under fed conditions with a PPI.

FIG. 4 summarizes the PK data for F2A under fed conditions with a PPI.

Example 15

Formulation Comparison

The pharmacokinetic data for administration of formulations F1 (pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide not comprising at least one acidulant), F2 (pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide with fumaric acid as an acidulant) and F2A (pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide with betaine hydrochloric acid as an acidulant) under fasted or fed conditions with a PPI are compared in the table below.

| FASTED | | | | |
|---|---|---|---|---|
| | % CV Comparison | | Exposure | |
| | $C_{max}$ | $AUC_\infty$ | $C_{max}$ | $AUC_\infty$ |
| F1 | 107 | 108 | 623 | 26700 |
| F2 | 24 | 31 | 2110 | 59600 |
| F2A | 31 | 35 | 1500 | 39400 |

| FED | | | | |
|---|---|---|---|---|
| | % CV Comparison | | Exposure | |
| | $C_{max}$ | $AUC_\infty$ | $C_{max}$ | $AUC_\infty$ |
| F1 | 36 | 30 | 2550 | 88600 |
| F2 | 20 | 28 | 2560 | 102000 |
| F2A | 27 | 32 | 2270 | 95800 |

In general, exposure is higher under fed conditions, and high-fat is better than medium-fat conditions. In addition, exposure is higher without the administration of a PPI. Both F2 and F2A improved inter-subject variability significantly compared to F1 under fasted dosing in the presence of a PPI, and exposure trends are higher for F2A than for F1, but not to a statistically significant level. All three formulations provide similar inter-subject variability and absolute exposure under fed conditions, when a high-fat meal was used.

Example 16

Dose Comparisons

Pharmacokinetic parameters were evaluated for dosing with food for formulation F1 following continuous dosing of F1 at doses of 100, 200, 400, and 800 mg/m²/day. As shown in the table below, F1 exposure (Cmax and AUC) increased with the dose in a dose-proportional manner between 100 mg/m² and 400 mg/m². Exposure trended approximately two times higher compared with Day 1 at each dose level. At 800 mg/m², exposure of F1 is comparable to 400 mg/m² dosing, and showed similar accumulation on Day 14. Lower exposure was seen on Day 28 as compared to Day 14, likely due to a combination of research variables.

| Dose | Day | N | Subject | $T_{max}$[a] (h) | $C_{max}$ (nM) | $AUC_{0-24}$ (nM · h) |
|---|---|---|---|---|---|---|
| 100 mg/m² | 1 | 5 | Mean | 6 | 549 | 7500 |
| | | | CV % | 4-8 | 37.5 | 28.6 |
| | 28 | 3 | Mean | 4 | 1140 | 20400 |
| | | | CV % | 2-8 | 19.6 | 24.4 |
| 200 mg/m² | 1 | 5 | Mean | 6 | 1450 | 21000 |
| | | | CV % | 4-8 | 50.4 | 40.5 |
| | 28 | 5 | Mean | 4 | 2120 | 33600 |
| | | | CV % | 2-6 | 39.6 | 45.7 |
| 400 mg/m² | 1 | 10 | Mean | 4 | 2730 | 41300[b] |
| | | | CV % | 2-8 | 43.3 | 52.5 |
| | 28 | 7 | Mean | 4 | 4400 | 89400[c] |
| | | | CV % | 2-6 | 44.6 | 37.7 |
| 800 mg/m² | 1 | 8 | Mean | 5 | 3770 | 53200 |
| | | | CV % | 4-8 | 51.5 | 55.1 |
| | 14 | 5 | Mean | 6 | 5770 | 101000 |
| | | | CV % | 2-24 | 63.5 | 70.7 |
| | 28 | 3[d] | Mean | 4 | 3840 | 62400 |
| | | | CV % | 2-8 | 33.5 | 44.1 |

[a] Median and range of $T_{max}$ reported;
[b] N = 9;
[c] N = 6;
[d] all are at 600 mg dosing.

Example 17

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric acid is prepared as follows.

| Component | Amount Per Capsule (mg) | Amount per Batch (g) |
|---|---|---|
| Materials for step (a) | | |
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 132.0 |
| Lactose Anhydrous, DT, NF | 124.15 | 74.49 |
| Hypromellose, USP (Methocel E5) | 18.00 | 10.80 |
| Croscarmellose Sodium, NF/EP (Ac-Di-Sol) | 11.25 | 6.750 |
| (L) Tartaric Acid, USP/NF | 80.85 | 53.36 |
| Magnesium Stearate, Non-Bovine Hyqual, NF, EP | 2.250 | 1.350 |
| Materials for step (b) | | |
| Croscarmellose Sodium, NF/EP (Ac-Di-Sol) | 11.25 | 6.750 |
| Magnesium Stearate, Non-Bovine Hyqual, NF, EP | 2.250 | 1.350 |
| Total | 450.0 | 270.0 |

(a). Each of the components in the table above for step (a) is weighed out as set forth in the table for each batch of capsules. The N-[5-(3,5-difluorobenzyl)-1H-indazol-3-yl]-4-(4-methyl-piperazin-1-yl)-2-(tetrahydro-2H-pyran-4-ylamino)-benzamide is passed through a 30 mesh hand screen. Each of the lactose, hypromellose, and croscarmellose is passed through a 20 mesh hand screen into a container. The tartaric acid is passed through a Frewitt Oscillator with a 0.4 mm opening screen and collected into a separate container. The N-[5-(3,5-difluorobenzyl)-1H-indazol-3-yl]-4-(4-methyl-piperazin-1-yl)-2-(tetrahydro-2H-pyran-4-ylamino)-benzamide, lactose, hypromellose, and tartaric acid are placed into a V-blender and the mixture is blended for 10 minutes. The magnesium stearate is passed through a 20 mesh screen and added to the V-blender and the resulting mixture is blended for 5 minutes. The resulting blend is placed into a suitable container lined with double-polyethylene bags. The mixture is granulated using TFC Lab Micro Roller Compactor using a roller speed of 2,500 rpm and a roller hydraulic pressure of 500 psi until the fines are minimized. A 20-mesh screen is used to screen out fines which are the added to the granulation mixture. The mixture is then passed through a Frewitt Oscillator equipped with a 0.80 mm screen.
(b). The croscarmellose and magnesium stearate in the table above for step (b) are weighed and passed through a 20-mesh screen. The mixture from step (a) above is added to a V-blender along with the extra-granular croscarmellose and blended for 10 minutes. The magnesium stearate is then added to the mixture and the resulting mixture is blended in a V-blender for 5 minutes.
c. Approximately 450 mg of the blend from step (b) is filled into gelatin capsule shells or HPMC capsule shells and the resulting capsules are manually de-dusted as needed.

Example 18

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric acid is prepared utilizing the ingredients in the amounts listed below and according to a procedure similar to that disclosed in Example 17, except that the TFC Lab Micro Roller Compactor was used in step (a) was set at a speed of 2,500 rpm and a hydraulic pressure of 750 psi, and the Frewitt Oscillator used in step (a) was equipped with a 0.80 mm screen.

| Component | Amount Per Capsule (mg) | Amount per Batch (g) |
|---|---|---|
| Materials for step (a) | | |
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 132.0 |
| Silicified Microcrystalline Cellulose (Prosolv SMCC 90) | 124.15 | 74.49 |
| Hypromellose, USP (Methocel E5) | 18.00 | 10.80 |
| Croscarmellose Sodium, NF/EP (Ac-Di-Sol) | 11.25 | 6.750 |
| (L) Tartaric Acid, USP/NF | 80.85 | 48.51 |
| Magnesium Stearate, Non-Bovine Hyqual, NF, EP | 2.250 | 1.350 |
| Materials for step (b) | | |
| Croscarmellose Sodium, NF/EP (Ac-Di-Sol) | 11.25 | 6.750 |
| Magnesium Stearate, Non-Bovine Hyqual, NF, EP | 2.250 | 1.350 |
| Total | 450.0 | 270.0 |

Example 19

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric acid is prepared utilizing the ingredients in the amounts listed below and according to a procedure similar to that disclosed in Example 17, except that except that the TFC Lab Micro Roller Compactor was used in step (a) was set at a speed of 2,500 rpm and a hydraulic pressure of 750 psi, and the Frewitt Oscillator used in step (a) was equipped with a 0.80 mm screen.

| Component | Amount Per Capsule (mg) | Amount per Batch (g) |
|---|---|---|
| Materials for step (a) | | |
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 132.0 |
| Mannitol, USP (Pearlitol 100SD) | 90.00 | 54.00 |
| Microcrystalline Cellulose (Avicel PH 102) | 34.15 | 20.49 |
| Hypromellose, USP (Methocel E5) | 18.00 | 10.80 |
| Croscarmellose Sodium, NF/EP (Ac-Di-Sol) | 11.25 | 6.750 |
| (L) Tartaric Acid, USP/NF | 80.85 | 48.51 |
| Magnesium Stearate, Non-Bovine Hyqual, NF, EP | 2.250 | 1.350 |
| Materials for step (b) | | |
| Croscarmellose Sodium, NF/EP (Ac-Di-Sol) | 11.25 | 6.750 |
| Magnesium Stearate, Non-Bovine Hyqual, NF, EP | 2.250 | 1.350 |
| Total | 450.0 | 270.0 |

Example 20

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric acid is prepared utilizing the ingredients in the amounts listed below and according to a procedure similar to that disclosed in Example 17, except that except that the TFC Lab Micro Roller Compactor was used in step (a) was set at a speed of 2,500 rpm and a hydraulic pressure of 750 psi, and the Frewitt Oscillator used in step (a) was equipped with a 0.80 mm screen.

| Component | Amount Per Capsule (mg) | Amount per Batch (g) |
|---|---|---|
| Materials for step (a) | | |
| N-[5-(3,5-difluorobenzyl)-1H-indazol-3-yl]-4-(4-methyl-piperazin-1-yl)-2-(tetrahydro-2H-pyran-4-ylamino)-benzamide | 200.0 | 132.0 |
| Dicalcium Phosphate Anhydrous (A-Tab) | 90.00 | 54.00 |
| Microcrystalline Cellulose (Avicel PH 102) | 34.15 | 20.49 |
| Hypromellose, USP (Methocel E5) | 18.00 | 10.80 |
| Croscarmellose Sodium, NF/EP (Ac-Di-Sol) | 11.25 | 6.750 |
| (L) Tartaric Acid, USP/NF | 80.85 | 48.51 |
| Magnesium Stearate, Non-Bovine Hyqual, NF, EP | 2.250 | 1.350 |
| Materials for step (b) | | |
| Croscarmellose Sodium, NF/EP (Ac-Di-Sol) | 11.25 | 6.750 |
| Magnesium Stearate, Non-Bovine Hyqual, NF, EP | 2.250 | 1.350 |
| Total | 450.0 | 270.0 |

Example 21

Hereinafter Referred to as Pharmaceutical Composition "F05"

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric acid was prepared as follows.

| Component | % w/w | Amount per Capsule (mg) |
|---|---|---|
| Intragranular Components | | |
| N-[5-(3,5-difluorobenzyl)-1H-indazol-3-yl]-4-(4-methyl-piperazin-1-yl)-2-(tetrahydro-2H-pyran-4-ylamino)-benzamide | 44.44 | 200.00 |
| Lactose Anhydrous | 32.44 | 146.00 |
| Hydroxypropyl Methylcellulose | 4.00 | 18.00 |
| Crospovidone | 2.78 | 12.50 |
| Tartaric Acid | 9.56 | 43.00 |
| Magnesium Stearate | 0.56 | 2.50 |
| Extragranular Components | | |
| Microcrystalline Cellulose | 2.97 | 13.37 |
| Crospovidone | 2.50 | 11.25 |
| Colloidal Silicon Dioxide | 0.25 | 1.13 |
| Magnesium Stearate | 0.50 | 2.25 |
| Total | 100.0 | 450.00 |

The tartaric acid was screened through a 30-mesh screen. A blender was charged with the lactose, N-[5-(3,5-difluorobenzyl)-1H-indazol-3-yl]-4-(4-methyl-piperazin-1-yl)-2-(tetrahydro-2H-pyran-4-ylamino)-benzamide, hydroxypropyl methylcellulose, intragranular crospovidone, and screened tartaric acid and pre-blended for 250 revolutions. The resulting mixture was screened through a 30-mesh screen. The blender was charged with the screened pre-mixture, which was then blended for 250 revolutions. The intragranular magnesium stearate was then screened through a 20-mesh screen and charged into the blender, and blended into the pre-mixture for 125 revolutions. The resulting pre-blend was then roller compacted and milled through a 0.8-mm screen. The microcrystalline cellulose, extragranular crospovidone, and colloidal silicon dioxide was then screened through a 20-mesh screen. The blender was charged with the milled roller compacted pre-blend and the screened microcrystalline cellulose, extragranular crospovidone, and colloidal silicon dioxide, and then blended for 250 revolutions. The extragranular magnesium stearate was screened through a 20-mesh screen and charged into the blender. All components were final blended for 125 revolutions.

The resulting mixture was filled into HPMC capsule shells, opaque white, size #0. The powder blend was filled into the capsules to achieve the target fill weight, using an H&K 400 Encapsulator. The filled capsules were polished using a capsule deduster, passed through a metal detector, and passed through a weight sorter.

The fill weight range acceptance limits were set at 95% to 105%. The weight sorting target range acceptable limits were set at 95% to 105%. Only those capsules meeting the weight limits were used in the study described in Example 24.

Example 22

Hereinafter Referred to as Pharmaceutical Composition "F06"

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric acid was prepared utilizing the ingredients in the amounts listed below and according to a procedure similar to that disclosed in Example 21.

| Component | % w/w | Amount per Capsule (mg) |
|---|---|---|
| Intragranular Components | | |
| N-[5-(3,5-difluorobenzyl)-1H-indazol-3-yl]-4-(4-methyl-piperazin-1-yl)-2-(tetrahydro-2H-pyran-4-ylamino)-benzamide | 44.44 | 200.00 |
| Lactose Anhydrous | 28.89 | 130.00 |
| Hydroxypropyl Methylcellulose | 4.00 | 18.00 |
| Crospovidone | 2.78 | 12.50 |
| Tartaric Acid | 13.11 | 59.00 |
| Magnesium Stearate | 0.56 | 2.50 |
| Extragranular Components | | |
| Microcrystalline Cellulose | 2.97 | 13.37 |
| Crospovidone | 2.50 | 11.25 |
| Colloidal Silicon Dioxide | 0.25 | 1.13 |
| Magnesium Stearate | 0.50 | 2.25 |
| Total | 100.0 | 450.00 |

In some embodiments, composition of a capsule for F06 is as follows:

| Component | % w/w | Amount per Capsule (mg) |
|---|---|---|
| Capsule, HPMC, Size 0, Orange Opaque Body and Orange Opaque Cap | | 1 each |
| Titanium Dioxide | 1.5202 | 1.37-1.55 |

-continued

| Component | % w/w | Amount per Capsule (mg) |
|---|---|---|
| Hypromellose | QSP 100 | QSP 90-102 |
| FD&C Yellow #6 | 0.5774 | 0.52-0.59 |

QSP = Quantité Suffisante Pour" (Quality Sufficient For)

Alternatively, a manufacturing process for pharmaceutical composition F06 and its encapsulation using the above-described capsule is disclosed in Example 26.

Example 23

Hereinafter Referred to as Pharmaceutical Composition "F07"

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric acid was prepared utilizing the ingredients in the amounts listed below and according to a procedure similar to that disclosed in Example 21.

| Component | % w/w | Amount per Capsule (mg) |
|---|---|---|
| Intragranular Components | | |
| N-[5-(3,5-difluorobenzyl)-1H-indazol-3-yl]-4-(4-methyl-piperazin-1-yl)-2-(tetrahydro-2H-pyran-4-ylamino)-benzamide | 44.44 | 200.00 |
| Lactose Anhydrous | 25.33 | 114.00 |
| Hydroxypropyl Methylcellulose | 4.00 | 18.00 |
| Crospovidone | 2.78 | 12.50 |
| Tartaric Acid | 16.67 | 75.00 |
| Magnesium Stearate | 0.56 | 2.50 |
| Extragranular Components | | |
| Microcrystalline Cellulose | 2.97 | 13.37 |
| Crospovidone | 2.50 | 11.25 |
| Colloidal Silicon Dioxide | 0.25 | 1.13 |
| Magnesium Stearate | 0.50 | 2.25 |
| Total | 100.0 | 450.00 |

Example 24

Comparative Pharmacokinetic Study of F05, F06, and F07 Formulations

A comparative pharmacokinetic study in healthy, human subjects was conducted comparing a 600 mg dosage strength of pharmaceutical composition F05 (as described in Example 20), with a 600 mg dosage strength of pharmaceutical composition F06 (as described in Example 21), with a 600 mg dosage strength of pharmaceutical composition F07 (as described in Example 22), and compared with a 600 mg dosage strength of pharmaceutical composition similar to F2A (as described in Example 13), except that the N-[5-(3,5-difluorobenzyl)-1H-indazol-3-yl]-4-(4-methyl-piperazin-1-yl)-2-(tetrahydro-2H-pyran-4-ylamino)-benzamide was milled prior to mixing with the excipients and encapsulating the resulting pharmaceutical composition.

Pharmaceutical compositions F05, F06, F07, and milled F2A were administered orally with approximately 240 mL of water, according to the randomization scheme.

Subjects were randomized into four sequences, ABCDE, BDACF, CADBG, and DCBAH. Periods 1, 2, 3, and 4 were conducted as a crossover design under fasting conditions where all subjects received a single, oral dose of one of four different formulations (F05, F06, F07, or F2A). In Period 5, subjects received a single, oral dose of only one formulation comprising N-[5-(3,5-difluorobenzyl)-1H-indazol-3-yl]-4-(4-methyl-piperazin-1-yl)-2-(tetrahydro-2H-pyran-4-ylamino)-benzamide as per the randomization schedule, administered 30 minutes after the start of a high-fat, high-calorie meal (described below as "fed" or "fed conditions"). Following the administration of each respective dose of the formulation to each subject on day 1 of each period, pharmacokinetic samples were taken for 120 hours post-administration in order to measure the amount of N-[5-(3,5-difluorobenzyl)-1H-indazol-3-yl]-4-(4-methyl-piperazin-1-yl)-2-(tetrahydro-2H-pyran-4-ylamino)-benzamide and its des-methyl metabolite. On day 1 of each dosing period, a single dose of 16 mg ondansetron was administered without water approximately 30 to 45 minutes prior to administration of the respective formulation as a prophylactic, anti-emetic agent. Additional doses of ondansetron were administered approximately 8 to 12 hours following dosing of the respective administration at the discretion of the investigator. There was a washout period in each subject of at least 9 days between doses of the respective formulations.

A representative summary of Periods 1, 2, 3, 4 and 5 and the pharmaceutical compositions subjects in each sequence will receive in each Period is found below.

| Subject Group | Period 1 (fasted) | Period 2 (fasted) | Period 3 (fasted) | Period 4 (fasted) | Period 5 (fed) |
|---|---|---|---|---|---|
| ABCDE | F05 | F06 | F07 | F2A | F2A |
| BDACF | F06 | F2A | F05 | F07 | F07 |
| CADBG | F07 | F05 | F2A | F06 | F06 |
| DCBAH | F2A | F07 | F06 | F05 | F05 |

Treatments A and H utilized three 200 mg strength F05 capsules.

Treatments B and G utilized three 200 mg strength F06 capsules.

Treatments C and F utilized three 200 mg strength F07 capsules.

Treatments D and E utilized three 200 mg strength F2A capsules.

Treatments A, B, C, D, E, F, G, and H were as follows:

For all procedures scheduled post-N-[5-(3,5-difluorobenzyl)-1H-indazol-3-yl]-4-(4-methyl-piperazin-1-yl)-2-(tetrahydro-2H-pyran-4-ylamino) benzamide dosing, time points were relative to the time of N-[5-(3,5-difluorobenzyl)-1H-indazol-3-yl]-4-(4-methyl-piperazin-1-yl)-2-(tetrahydro-2H-pyran-4-ylamino)-benzamide dosing (i.e., Hour 0 on Day 1).

For all subjects, blood samples were collected at scheduled time points. Sampling time-points were relative to the time of N-[5-(3,5-difluorobenzyl)-1H-indazol-3-yl]-4-(4-methyl-piperazin-1-yl)-2-(tetrahydro-2H-pyran-4-ylamino)- benzamide dosing (i.e., Hour 0 on Day 1). Blood sampling for pharmacokinetic measurements were scheduled for the following times (in hours) (all time points were measured as relative to N-[5-(3,5-difluorobenzyl)-1H-indazol-3-yl]-4-(4-methyl-piperazin-1-yl)-2-(tetrahydro-2H-pyran-4-ylamino)-benzamide dosing, i.e., hour 0 on day 4 of the study): 0, 0.5, 1, 2, 3, 4, 5, 6, 8, 12, 24, 36, 48, 72, 96, and 120.

Subject plasma samples were analyzed for the presence of N-[5-(3,5-difluorobenzyl)-1H-indazol-3-yl]-4-(4-methyl-piperazin-1-yl)-2-(tetrahydro-2H-pyran-4-ylamino)-benzamide and the des-methyl metabolite of N-[5-(3,5-difluorobenzyl)-1H-indazol-3-yl]-4-(4-methyl-piperazin-1-yl)-2-(tetrahydro-2H-pyran-4-ylamino)-benzamide using analytical methods known to those of ordinary skill in the art.

All subjects who received at least one dose of N-[5-(3,5-difluorobenzyl)-1H-indazol-3-yl]-4-(4-methyl-piperazin-1-yl)-2-(tetrahydro-2H-pyran-4-ylamino)-benzamide and had evaluable PK data made up the PK Population and was used for all PK analyses. Samples from all subjects were assayed even if the subjects did not complete the study. All subjects who complied sufficiently with the protocol and displayed an evaluable PK profile (e.g., exposure to treatment, availability of measurements and absence of major protocol violations) was included in the statistical summary of PK parameters. Inclusion in the statistical analysis of any subject who vomited within 8 hours after dosing of the respective formulation, i.e., a period of time equal to two times the mean tmax of entrectinib were evaluated at the time of analysis. Additionally, in the case of insufficient washout, subjects with a predose concentration that exceeded 5% of the Cmax for the treatment being tested were considered to have unevaluable PK and were excluded from PK summary statistics and bioequivalence assessment for that treatment. Average bioequivalence comparison methodology was used in comparing treatments received by the same subjects. In order to prevent confounding of data, only subjects that had evaluable PK in both comparison treatments were used for analysis.

The following PK parameters were calculated for N-[5-(3,5-difluorobenzyl)-1H-indazol-3-yl]-4-(4-methyl-piperazin-1-yl)-2-(tetrahydro-2H-pyran-4-ylamino)-benzamide in plasma, as appropriate: $AUC_{0-t}$, $AUC_{0-inf}$, $C_{max}$, $T_{max}$.

The PK parameters $AUC_{0-t}$, $AUC_{0-inf}$, and $C_{max}$ for N-[5-(3,5-difluorobenzyl)-1H-indazol-3-yl]-4-(4-methyl-piperazin-1-yl)-2-(tetrahydro-2H-pyran-4-ylamino)-benzamide were analyzed using analysis of variance (ANOVA) model to calculate the geometric least squares mean (LSM) ratio using natural log-transformed data. A 90% confidence interval (CI) was constructed around the ratio of the geometric mean for the three PK parameters for N-[5-(3,5-difluorobenzyl)-1H-indazol-3-yl]-4-(4-methyl-piperazin-1-yl)-2-(tetrahydro-2H-pyran-4-ylamino)-benzamide.

Formulation F2A was used as the reference for all relative bioavailability analysis. Fasted dosing was used as the reference for food effect analysis. The following assessments were done: (1) the relative bioavailability of N-[5-(3,5-difluorobenzyl)-1H-indazol-3-yl]-4-(4-methyl-piperazin-1-yl)-2-(tetrahydro-2H-pyran-4-ylamino)-benzamide in four formulations under fasting conditions were evaluated by comparing Treatment A versus Treatment D, Treatment B versus Treatment D, and Treatment C versus Treatment D; (2) the effect of food on each of the four N-[5-(3,5-difluorobenzyl)-1H-indazol-3-yl]-4-(4-methyl-piperazin-1-yl)-2-(tetrahydro-2H-pyran-4-ylamino)-benzamide formulations F05, F06, F07, and F2A, were evaluated by comparing (a) for F05, Treatment A versus Treatment H (within the same treatment sequence), (b) for F06, Treatment B versus Treatment G (within the same treatment sequence), (c) for F07, Treatment C versus Treatment F (within the same treatment sequence), and (d) for F2A, Treatment D versus Treatment E (within the same treatment sequence); and (3) the relative bioavailability of N-[5-(3,5-difluorobenzyl)-1H-indazol-3-yl]-4-(4-methyl-piperazin-1-yl)-2-(tetrahydro-2H-pyran-4-ylamino)-benzamide in four formulations under fed conditions were evaluated by comparing Treatment F versus Treatment E, Treatment G versus Treatment E, and Treatment H versus Treatment E.

The results of the study are shown in the tables below. All values are reported as the mean value (% CV). For example, for formulation F05, the median $T_{max}$ for 48 subjects in the fasted state was about 3.58 hours, with a CV % of about 31.4%.

| Treatment | Formulation | Food | | N | $T_{max}$ (hr) | $C_{max}$ (nM) | $AUC_{0-120}$ (nM * hr) | $AUC_\infty$ (nM * hr) |
|---|---|---|---|---|---|---|---|---|
| A | F05 | Fasted | Mean | 48 | 3.58 | 2150 | 52900 | 53800 |
|   |   |   | CV % |   | 31.4 | 30.2 | 34.8 | 35.5 |
| B | F06 | Fasted | Mean | 48 | 3.54 | 2260 | 56100 | 57200 |
|   |   |   | CV % |   | 31.9 | 34.2 | 41.7 | 42 |
| C | F07 | Fasted | Mean | 48 | 3.67 | 2300 | 57200 | 58300 |
|   |   |   | CV % |   | 29.9 | 27.4 | 34.2 | 35.1 |
| D | F2A milled | Fasted | Mean | 48 | 3.44 | 2340 | 57600 | 58800 |
|   |   |   | CV % |   | 28.1 | 28.1 | 39 | 40.3 |

| Treatment | Formulation | Food | | N | $T_{max}$ (hr) | $C_{max}$ (nM) | $AUC_{0-120}$ (nM * hr) | $AUC_\infty$ (nM * hr) |
|---|---|---|---|---|---|---|---|---|
| H | F05 | Fed | Mean | 11 | 5 | 2440 | 58800 | 59400 |
|   |   |   | CV % |   | 8.94 | 25.7 | 33.9 | 34.2 |
| G | F06 | Fed | Mean | 12 | 5.83 | 2600 | 71800 | 73300 |
|   |   |   | CV % |   | 22.9 | 15 | 17.9 | 19 |
| F | F07 | Fed | Mean | 12 | 5.42 | 2400 | 64400 | 65700 |
|   |   |   | CV % |   | 22.9 | 17 | 20.4 | 21.3 |
| E | F2A milled | Fed | Mean | 12 | 5.25 | 2350 | 63200 | 64200 |
|   |   |   | CV % |   | 20.1 | 22.8 | 31.4 | 32.1 |

Example 25

Hereinafter Referred to as Pharmaceutical Composition "F06-100"

A pharmaceutical composition comprising N-[5-(3,5-difluorobenzyl)-1H-indazol-3-yl]-4-(4-methyl-piperazin-1-yl)-2-(tetrahydro-2H-pyran-4-ylamino)-benzamide and tartaric acid was prepared utilizing the ingredients in the amounts listed below and according to a procedure similar to that disclosed in Example 21.

| Component | % w/w | Amount per Capsule (mg) |
|---|---|---|
| Intragranular Components | | |
| N-[5-(3,5-difluorobenzyl)-1H-indazol-3-yl]-4-(4-methyl-piperazin-1-yl)-2-(tetrahydro-2H-pyran-4-ylamino)-benzamide | 44.44 | 100.00 |
| Lactose Anhydrous | 28.89 | 65.00 |
| Hydroxypropyl Methylcellulose | 4.00 | 9.00 |
| Crospovidone | 2.78 | 6.25 |
| Tartaric Acid | 13.11 | 29.50 |
| Magnesium Stearate | 0.56 | 1.25 |
| Extragranular Components | | |
| Microcrystalline Cellulose | 2.97 | 6.685 |
| Crospovidone | 2.50 | 5.625 |
| Colloidal Silicon Dioxide | 0.25 | 0.565 |
| Magnesium Stearate | 0.50 | 1.125 |
| Total | 100.0 | 225.00 |

In some embodiments, composition of a capsule for F06-100 is as follows:

| Component | % w/w | Amount per Capsule (mg) |
|---|---|---|
| Capsule, HPMC, Size 2, Yellow Opaque Body and Yellow Opaque Cap | | 1 each |
| Titanium Dioxide | 1.4584 | 0.83-0.98 |
| Hypromellose | QSP 100 | QSP 57-65 |
| FDA/E172 Yellow Iron Oxide | 0.2307 | 0.13-0.15 |

QSP = Quantité Suffisante Pour" (Quality Sufficient For)

Alternatively, a manufacturing process for pharmaceutical composition F06-100 and its encapsulation using the above-described capsule is disclosed in Example 26.

Example 26

Manufacturing Process for Capsules Containing F06 and F06-100

The manufacturing process for capsules containing F06 and F06-100 was divided into four parts: 1) manufacture of the intragranular blend, 2) manufacture of the extragranular blend, 3) encapsulation, and 4) capsule packaging. The first two parts (manufacture of the intragranular blend and manufacture of the extragranular blend) form the dry granulation blending process of F06 and F06-100 capsules. The dry granulation blending process consisted of the following steps: Pre-blending, roller compaction, milling, blending, final blending (lubrication), and encapsulation as detailed below:

1) Manufacture of the Intragranular Blend:
   1. Charge N-[5-(3,5-difluorobenzyl)-1H-indazol-3-yl]-4-(4-methyl-piperazin-1-yl)-2-(tetrahydro-2H-pyran-4-ylamino)-benzamide, Lactose Anhydrous, Hypromellose, Tartaric acid, Crospovidone (Portion 1) into a tote blender and blend for approximately 125 revolutions. Screen the pre-blend through a 30-mesh screen.
   2. Charge the screened pre-blend into the blender and blend for approximately 250 revolutions. Screen the pre-blend through a 30-mesh screen.
   3. Charge the screened pre-blend into the blender and blend for approximately additional 250 revolutions.
   4. Screen Magnesium Stearate (Portion 1) through a 20-mesh screen and add to the blender and blend for 125 revolutions.
   5. Roller compact the blend to obtain the compacted material.
   6. Pass the roller compacted material through a 0.80 mm screen.
2) Manufacture of the Extragranular Blend:
   1. Using the yield of the milled material, adjust and reweigh the required quantities of Microcrystalline Cellulose, Crospovidone (Portion 2), Colloidal Silicon Dioxide, and Magnesium Stearate (Portion 2).
   2. Screen the Microcrystalline Cellulose, Crospovidone (Portion 2), Colloidal Silicon Dioxide, and Magnesium Stearate (Portion 2) through a-20 mesh screen, while keeping the Magnesium Stearate separate.
   3. Charge the screened Microcrystalline Cellulose, Crospovidone (Portion 2), Colloidal Silicon Dioxide, and milled material to the blender and blend for approximately 250 revolutions.
   4. Charge the screened Magnesium Stearate to the blender and blend for approximately 125 revolutions to create the final dry granulation blend.
3) Encapsulation:
   1. Fill the final dry granulation blend using the encapsulator, with continuous monitoring, into size 0 or size 2 HPMC capsule shell for 200-mg and 100-mg strengths, respectively.
4) Packaging:
   1. 100-mg Strength (F06-100): Fill thirty 100-mg capsules into a 40 cc white HDPE bottle with one 0.5-g desiccant canister, enclosed with a 33 mm white child-resistant caps and induction heat sealed.
   2. 200-mg Strength (F06): Fill ninety 200-mg capsules into a 150 cc white HDPE bottle with one 2-g desiccant canister, enclosed with a 38 mm white child-resistant caps and induction heat sealed.

Para. A. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant.

Para. B. The pharmaceutical composition of Para. A, wherein said at least one acidulant is an organic acidulant.

Para. C. The pharmaceutical composition of Para. A, wherein said at least one acidulant is selected from tartaric acid, maleic acid, fumaric acid, citric acid, and betaine hydrochloride.

Para. D. The pharmaceutical composition of Para. C, wherein said at least one acidulant is fumaric acid.

Para. E. The pharmaceutical composition of Para. C, wherein said fumaric acid is in a micronized form.

Para. F. The pharmaceutical composition of Para. C, wherein said at least one acidulant is tartaric acid.

Para. G. The pharmaceutical composition of Para. C, wherein said at least one acidulant is maleic acid.

Para. H. The pharmaceutical composition of Para. C, wherein said at least one acidulant is citric acid.

Para. I. The pharmaceutical composition of Para. C, wherein said at least one acidulant is betaine hydrochloride.

Para. J. The pharmaceutical composition of any one of Paras. A-I, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 0.5 to about 2.

Para. K. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 0.75 to about 1.75.

Para. L. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 1 to about 1.75.

Para. M. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 1 to about 1.5.

Para. N. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 1.25 to about 1.75.

Para. O. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 1 to about 1.5.

Para. P. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is about 1.5.

Para. Q. The pharmaceutical composition of any one of Paras. A-P, wherein said pharmaceutical composition is in the form of a tablet or capsule.

Para. R. The pharmaceutical composition of Para. Q, wherein said pharmaceutical composition is in the form of a tablet.

Para. S. The pharmaceutical composition of Para. Q, wherein said pharmaceutical composition is in the form of a capsule.

Para. T. The pharmaceutical composition of any one of Paras. A-S, wherein said pharmaceutical composition comprises from about 25 mg to about 500 mg of said N-[5-(3,5-difluorobenzyl)-1H-indazol-3-yl]-4-(4-methyl-piperazin-1-yl)-2-(tetrahydro-pyran-4-ylamino)-benzamide.

Para. U. The pharmaceutical composition of Para. T, wherein said pharmaceutical composition comprises from about 50 mg to about 450 mg of said N-[5-(3,5-difluorobenzyl)-1H-indazol-3-yl]-4-(4-methyl-piperazin-1-yl)-2-(tetrahydro-pyran-4-ylamino)-benzamide.

Para. V. The pharmaceutical composition of Para. T, wherein said pharmaceutical composition comprises from about 50 mg to about 450 mg of said N-[5-(3,5-difluorobenzyl)-1H-indazol-3-yl]-4-(4-methyl-piperazin-1-yl)-2-(tetrahydro-pyran-4-ylamino)-benzamide.

Para. W. The pharmaceutical composition of Para. T, wherein said pharmaceutical composition comprises from about 50 mg to about 200 mg of said N-[5-(3,5-difluorobenzyl)-1H-indazol-3-yl]-4-(4-methyl-piperazin-1-yl)-2-(tetrahydro-pyran-4-ylamino)-benzamide.

Para. X. The pharmaceutical composition of Para. T, wherein said pharmaceutical composition comprises about 50 mg of said N-[5-(3,5-difluorobenzyl)-1H-indazol-3-yl]-4-(4-methyl-piperazin-1-yl)-2-(tetrahydro-pyran-4-ylamino)-benzamide.

Para. Y. The pharmaceutical composition of Para. T, wherein said pharmaceutical composition comprises about 100 mg of said N-[5-(3,5-difluorobenzyl)-1H-indazol-3-yl]-4-(4-methyl-piperazin-1-yl)-2-(tetrahydro-pyran-4-ylamino)-benzamide.

Para. Z. The pharmaceutical composition of Para. T, wherein said pharmaceutical composition comprises about 200 mg of said N-[5-(3,5-difluorobenzyl)-1H-indazol-3-yl]-4-(4-methyl-piperazin-1-yl)-2-(tetrahydro-pyran-4-ylamino)-benzamide.

Para. AA. The pharmaceutical composition of Para. D, wherein the particle size of said fumaric acid is such that it passes through a 60-mesh screen.

Para. AB. The pharmaceutical composition of Para. A, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide degrades in said pharmaceutical composition after said pharmaceutical composition is stored for 3 months in an open container at 40° C. and 75% relative humidity.

Para. AC. The pharmaceutical composition of Para. A, wherein more than about 98% of said N-[5-(3,5-difluorobenzyl)-1H-indazol-3-yl]-4-(4-methyl-piperazin-1-yl)-2-(tetrahydro-pyran-4-ylamino)-benzamide is present in said pharmaceutical composition after said pharmaceutical composition is stored for 3 months in an open container at 40° C. and 75% relative humidity.

Para. AD. The pharmaceutical composition of Para. A, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide degrades in said pharmaceutical composition after said pharmaceutical composition is stored for 3 months in an open container at 60° C. and 75% relative humidity.

Para. AE. The pharmaceutical composition of Para. A, wherein more than about 98% of said N-[5-(3,5-difluorobenzyl)-1H-indazol-3-yl]-4-(4-methyl-piperazin-1-yl)-2-(tetrahydro-pyran-4-ylamino)-benzamide is present in said pharmaceutical composition after said pharmaceutical composition is stored for 3 months in an open container at 60° C. and 75% relative humidity.

Para. AF. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one pharmaceutically acceptable excipient, wherein said pharmaceutical composition is in the form of a tablet or capsule, and wherein said tablet or capsule has a dissolution profile wherein at least about 30% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 60 minutes when tested in USP Apparatus Type I Basket Method at 50 rpm in 500 mL of sodium acetate buffer at a pH of 4.5 and at about 37° C.

Para. AG. The pharmaceutical composition of Para. AF, wherein said tablet or capsule has a dissolution profile wherein at least about 20% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 45 minutes when tested in USP Apparatus Type I Basket Method at 50 rpm in 500 mL of sodium acetate buffer at a pH of 4.5 and at about 37° C.

Para. AH. The pharmaceutical composition of Para. AF, wherein said tablet or capsule has a dissolution profile wherein at least about 15% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 30 minutes when tested in USP Apparatus Type I Basket Method at 50 rpm in 500 mL of sodium acetate buffer at a pH of 4.5 and at about 37° C.

Para. AI. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one pharmaceutically acceptable excipient, wherein said pharmaceutical composition is in the form of a tablet or capsule, and wherein said tablet or capsule has a dissolution profile wherein at least about 50% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 60 minutes when tested in USP Apparatus Type I Basket Method at 50 rpm in 500 mL of sodium acetate buffer at a pH of 4.5 and at about 37° C.

Para. AJ. The pharmaceutical composition of Para. AI, wherein said tablet or capsule has a dissolution profile wherein at least about 40% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 45 minutes when tested in USP Apparatus Type I Basket Method at 50 rpm in 500 mL of sodium acetate buffer at a pH of 4.5 and at about 37° C.

Para. AK. A solid pharmaceutical composition according to Para. AI, wherein said tablet or capsule has a dissolution profile wherein at least about 20% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 30 minutes when tested in USP Apparatus Type I Basket Method at 50 rpm in 500 mL of sodium acetate buffer at a pH of 4.5 and at about 37° C.

Para. AL. The pharmaceutical composition of any one of Paras. A-AK, wherein said pharmaceutical composition further comprises mannitol or isomalt.

Para. AM. The pharmaceutical composition of Para. AL, wherein said pharmaceutical composition further comprises starch.

Para. AN. The pharmaceutical composition of Para. AM, wherein the weight to weight ratio of said mannitol or isomalt to said starch in said pharmaceutical composition is from about 1 to 1 to about 3 to 1.

Para. AO. The pharmaceutical composition of Para. AN, wherein said weight to weight ratio of said mannitol or isomalt to said starch in said pharmaceutical composition is from about 1.5 to 1 to about 3 to 1.

Para. AP. The pharmaceutical composition of Para. AN, wherein said weight to weight ratio of said mannitol or isomalt to said starch in said pharmaceutical composition is from about 1.75 to 1 to about 3 to 1.

Para. AQ. The pharmaceutical composition of Para. AN, wherein said weight to weight ratio of said mannitol or isomalt to said starch in said pharmaceutical composition is from about 1 to 1 to about 2.5 to 1.

Para. AR. The pharmaceutical composition of Para. AN, wherein said weight to weight ratio of said mannitol or isomalt to said starch in said pharmaceutical composition is from about 1 to 1 to about 2 to 1.

Para. AS. The pharmaceutical composition of Para. AN, wherein said weight to weight ratio of said mannitol or isomalt to said starch in said pharmaceutical composition is about 2 to 1.

Para. AT. The pharmaceutical composition of Para. AN, wherein said weight to weight ratio of said mannitol or isomalt to said starch in said pharmaceutical composition is about 1.8.

Para. AU. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and 6 hours following said administration of said pharmaceutical composition to said subject.

Para. AV. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 5 hours and 12 hours following said administration of said pharmaceutical composition to said subject.

Para. AW. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2080 nM and about 2110 nM following said administration of said pharmaceutical composition to said subject.

Para. AX. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2080 nM and about 2560 nM following said administration of said pharmaceutical composition to said subject.

Para. AY. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between 80% to 125% of 2080 nM, based on a 90 percent confidence interval following said administration of said pharmaceutical composition to said subject.

Para. AZ. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between 80% to 125% of 2560 nM, based on a 90 percent confidence interval following said administration of said pharmaceutical composition to said subject.

Para. BA. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 28,900 nM*hr and about 30,800 nM*hr following said administration of said pharmaceutical composition to said subject.

Para. BB. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed rate at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is about 40,400 nM*hr following said administration of said pharmaceutical composition to said subject.

Para. BC. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 30,800 nM*hr at a 90% confidence interval following said administration of said pharmaceutical composition to said subject.

Para. BD. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 40,400 nM*hr at a 90% confidence interval following said administration of said pharmaceutical composition to said subject.

Para. BE. The pharmaceutical composition of any one of Paras. AA-BD, wherein said pharmaceutical composition is in the form of a tablet or capsule.

Para. BF. The pharmaceutical composition of Para. BE, wherein said pharmaceutical composition is in the form of a capsule.

Para. BG. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2080 nM and about 2100 nM following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BH. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of about 2560 nM following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BI. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 28,900 nM*hr and about 30,800 nM*hr following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BJ. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of about 40,400 nM*hr following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BK. A pharmaceutical composition, comprising: N-[5-(3,5-difluorobenzyl)-1H-indazol-3-yl]-4-(4-methyl-piperazin-1-yl)-2-(tetrahydro-pyran-4-ylamino)-benzamide; and
means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 6 hours following administration of said pharmaceutical composition to said subject in a fasted state.

Para. BL. A pharmaceutical composition, comprising: N-[5-(3,5-difluorobenzyl)-1H-indazol-3-yl]-4-(4-methyl-piperazin-1-yl)-2-(tetrahydro-pyran-4-ylamino)-benzamide; and
means for delivering a $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 5 hours and about 12 hours following administration of said pharmaceutical composition to said subject in a fed state.

Para. BM. A pharmaceutical composition, comprising: N-[5-(3,5-difluorobenzyl)-1H-indazol-3-yl]-4-(4-methyl-piperazin-1-yl)-2-(tetrahydro-pyran-4-ylamino)-benzamide; and
means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2080 nM, based on a 90 percent confidence interval, following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BN. A pharmaceutical composition, comprising: N-[5-(3,5-difluorobenzyl)-1H-indazol-3-yl]-4-(4-methyl-piperazin-1-yl)-2-(tetrahydro-pyran-4-ylamino)-benzamide; and
means for delivering a $C_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2560 nM, based on a 90 percent confidence interval, following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BO. A pharmaceutical composition, comprising: N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 30,800 nM*hr, based on a 90 percent confidence interval, following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BP. A pharmaceutical composition, comprising: N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 40,400 nM*hr, based on a 90 percent confidence interval, following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BQ. A pharmaceutical composition, comprising: N-[5-(3,5-difluorobenzyl)-1H-indazol-3-yl]-4-(4-methyl-piperazin-1-yl)-2-(tetrahydro-pyran-4-ylamino)-benzamide; and
means for delivering said N-[5-(3,5-difluorobenzyl)-1H-indazol-3-yl]-4-(4-methyl-piperazin-1-yl)-2-(tetrahydro-pyran-4-ylamino)-benzamide to a subject that exhibits no food effect.

Para. BR. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide, wherein said pharmaceutical composition exhibits no food effect when administered to a subject.

Para. BS. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 0.5 to about 1.5.

Para. BT. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 0.5 to about 1.25.

Para. BU. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 0.5 to about 1.

Para. BV. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is about 1.2.

Para. BW. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is about 0.9.

Para. BX. The pharmaceutical composition of Para. J, wherein said molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is about 0.7.

Para. BY. The pharmaceutical composition of Para. T, wherein said pharmaceutical composition comprises from about 50 mg to about 300 mg of said N-[5-(3,5-difluorobenzyl)-1H-indazol-3-yl]-4-(4-methyl-piperazin-1-yl)-2-(tetrahydro-pyran-4-ylamino)-benzamide.

Para. BZ. The pharmaceutical composition of Para. F, wherein the particle size of said tartaric acid is such that it passes through a 30-mesh screen.

Para. CA. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and 5 hours following said administration of said pharmaceutical composition to said subject.

Para. CB. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2.5 hours and 4.7 hours following said administration of said pharmaceutical composition to said subject.

Para. CC. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2.4 hours and 4.7 hours following said administration of said pharmaceutical composition to said subject.

Para. CD. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2.6 hours and 4.8 hours following said administration of said pharmaceutical composition to said subject.

Para. CE. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4 hours and 8 hours following said administration of said pharmaceutical composition to said subject.

Para. CF. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4.6 hours and 5.4 hours following said administration of said pharmaceutical composition to said subject.

Para. CG. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4.5 hours and 7.2 hours following said administration of said pharmaceutical composition to said subject.

Para. CH. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 4.2 hours and 6.7 hours following said administration of said pharmaceutical composition to said subject.

Para. CI. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1200 nM and 3500 nM following said administration of said pharmaceutical composition to said subject.

Para. CJ. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 2800 nM following said administration of said pharmaceutical composition to said subject.

Para. CK. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1490 nM and about 3030 nM following said administration of said pharmaceutical composition to said subject.

Para. CL. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4- ylamino)-benzamide in the plasma of said subject is between about 1670 nM and about 2930 nM following said administration of said pharmaceutical composition to said subject.

Para. CM. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1500 nM and about 3500 nM following said administration of said pharmaceutical composition to said subject.

Para. CN. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1810 nM and about 3070 nM following said administration of said pharmaceutical composition to said subject.

Para. CO. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2210 nM and about 2990 nM following said administration of said pharmaceutical composition to said subject.

Para. CP. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 1990 nM and about 2810 nM following said administration of said pharmaceutical composition to said subject.

Para. CQ. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr following said administration of said pharmaceutical composition to said subject.

Para. CR. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 34,100 nM*hr and about 71,700 nM*hr following said administration of said pharmaceutical composition to said subject.

Para. CS. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 32,500 nM*hr and about 79,700 nM*hr following said administration of said pharmaceutical composition to said subject.

Para. CT. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 37,100 nM*hr and about 77,300 nM*hr following said administration of said pharmaceutical composition to said subject.

Para. CU. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr following said administration of said pharmaceutical composition to said subject.

Para. CV. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 38,900 nM*hr and about 78,700 nM*hr following said administration of said pharmaceutical composition to said subject.

Para. CW. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 58,900 nM*hr and about 84,700 nM*hr following said administration of said pharmaceutical composition to said subject.

Para. CX. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 51,300 nM*hr and about 77,500 nM*hr following said administration of said pharmaceutical composition to said subject.

Para. CY. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 30,000 nM*hr and about 85,000 nM*hr following said administration of said pharmaceutical composition to said subject.

Para. CZ. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 34,700 nM*hr and about 72,900 nM*hr following said administration of said pharmaceutical composition to said subject.

Para. DA. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 33,200 nM*hr and about 81,200 nM*hr following said administration of said pharmaceutical composition to said subject.

Para. DB. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 37,800 nM*hr and about 78,800 nM*hr following said administration of said pharmaceutical composition to said subject.

Para. DC. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 35,000 nM*hr and about 90,000 nM*hr following said administration of said pharmaceutical composition to said subject.

Para. DD. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 39,100 nM*hr and about 79,700 nM*hr following said administration of said pharmaceutical composition to said subject.

Para. DE. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 59,400 nM*hr and about 87,200 nM*hr following said administration of said pharmaceutical composition to said subject.

Para. DF. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 51,700 nM*hr and about 79,700 nM*hr following said administration of said pharmaceutical composition to said subject.

Para. DG. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 3.6 hours at a 90% confidence interval following said administration of said pharmaceutical composition to said subject.

Para. DH. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 3.5 hours at a 90% confidence interval following said administration of said pharmaceutical composition to said subject.

Para. DI. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 3.7 hours at a 90% confidence interval following said administration of said pharmaceutical composition to said subject.

Para. DJ. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 5 hours at a 90% confidence interval following said administration of said pharmaceutical composition to said subject.

Para. DK. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 5.8 hours at a 90% confidence interval following said administration of said pharmaceutical composition to said subject.

Para. DL. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 5.4 hours at a 90% confidence interval following said administration of said pharmaceutical composition to said subject.

Para. DM. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 2150 nM at a 90% confidence interval following said administration of said pharmaceutical composition to said subject.

Para. DN. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 2260 nM at a 90% confidence interval following said administration of said pharmaceutical composition to said subject.

Para. DO. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 2300 nM at a 90% confidence interval following said administration of said pharmaceutical composition to said subject.

Para. DP. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 2440 nM at a 90% confidence interval following said administration of said pharmaceutical composition to said subject.

Para. DQ. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 2600 nM at a 90% confidence interval following said administration of said pharmaceutical composition to said subject.

Para. DR. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 2400 nM at a 90% confidence interval following said administration of said pharmaceutical composition to said subject.

Para. DS. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 52,900 nM*hr at a 90% confidence interval following said administration of said pharmaceutical composition to said subject.

Para. DT. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 56,100 nM*hr at a 90% confidence interval following said administration of said pharmaceutical composition to said subject.

Para. DU. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 57,200 nM*hr at a 90% confidence interval following said administration of said pharmaceutical composition to said subject.

Para. DV. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 58,800 nM*hr at a 90% confidence interval following said administration of said pharmaceutical composition to said subject.

Para. DW. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 71,800 nM*hr at a 90% confidence interval following said administration of said pharmaceutical composition to said subject.

Para. DX. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 64,400 nM*hr at a 90% confidence interval following said administration of said pharmaceutical composition to said subject.

Para. DY. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 53,800 nM*hr at a 90% confidence interval following said administration of said pharmaceutical composition to said subject.

Para. DZ. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 57,200 nM*hr at a 90% confidence interval following said administration of said pharmaceutical composition to said subject.

Para. EA. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fasted state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 58,300 nM*hr at a 90% confidence interval following said administration of said pharmaceutical composition to said subject.

Para. EB. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 59,400 nM*hr at a 90% confidence interval following said administration of said pharmaceutical composition to said subject.

Para. EC. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 73,300 nM*hr at a 90% confidence interval following said administration of said pharmaceutical composition to said subject.

Para. ED. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant, wherein said pharmaceutical composition when administered to a subject in a fed state provides a pharmacokinetic profile in said subject wherein the AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is within about 80% to about 125% of 65,700 nM*hr at a 90% confidence interval following said administration of said pharmaceutical composition to said subject.

Para. EE. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2 hours and about 5 hours following administration of said pharmaceutical composition to said subject in a fasted state.

Para. EF. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 6 hours following administration of said pharmaceutical composition to said subject in a fed state.

Para. EG. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 8 hours following administration of said pharmaceutical composition to said subject in a fed state.

Para. EH. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 4 hours and about 7 hours following administration of said pharmaceutical composition to said subject in a fed state.

Para. EI. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1500 nM and about 2800 nM following administration of said pharmaceutical composition to said subject in a fasted state.

Para. EJ. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1490 nM and about 3030 nM following administration of said pharmaceutical composition to said subject in a fasted state.

Para. EK. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1670 nM and about 2930 nM following administration of said pharmaceutical composition to said subject in a fasted state.

Para. EL. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1810 nM and about 3070 nM following administration of said pharmaceutical composition to said subject in a fed state.

Para. EM. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 2210 nM and about 2990 nM following administration of said pharmaceutical composition to said subject in a fed state.

Para. EN. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 1990 nM and about 2810 nM following administration of said pharmaceutical composition to said subject in a fed state.

Para. EO. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 34,100 nM*hr and about 71,700 nM*hr following administration of said pharmaceutical composition to said subject in a fasted state.

Para. EP. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 32,500 nM*hr and about 79,700 nM*hr following administration of said pharmaceutical composition to said subject in a fasted state.

Para. EQ. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 37,100 nM*hr and about 77,300 nM*hr following administration of said pharmaceutical composition to said subject in a fasted state.

Para. ER. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 38,900 nM*hr and about 78,700 nM*hr following administration of said pharmaceutical composition to said subject in a fed state.

Para. ES. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 58,900 nM*hr and about 84,700 nM*hr following administration of said pharmaceutical composition to said subject in a fed state.

Para. ET. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 51,300 nM*hr and about 77,500 nM*hr following administration of said pharmaceutical composition to said subject in a fed state.

Para. EU. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 34,700 nM*hr and about 72,900 nM*hr following administration of said pharmaceutical composition to said subject in a fasted state.

Para. EV. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 33,200 nM*hr and about 81,200 nM*hr following administration of said pharmaceutical composition to said subject in a fasted state.

Para. EW. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 37,800 nM*hr and about 78,800 nM*hr following administration of said pharmaceutical composition to said subject in a fasted state.

Para. EX. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 39,100 nM*hr and about 79,700 nM*hr following administration of said pharmaceutical composition to said subject in a fed state.

Para. EY. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 59,400 nM*hr and about 87,200 nM*hr following administration of said pharmaceutical composition to said subject in a fed state.

Para. EZ. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject of between about 51,700 nM*hr and about 79,700 nM*hr following administration of said pharmaceutical composition to said subject in a fed state.

Para. FA. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.6 hours, based on a 90 percent confidence interval, following administration of said pharmaceutical composition to said subject in a fasted state.

Para. FB. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.5 hours, based on a 90 percent confidence interval, following administration of said pharmaceutical composition to said subject in a fasted state.

Para. FC. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 3.7 hours, based on a 90 percent confidence interval, following administration of said pharmaceutical composition to said subject in a fasted state.

Para. FD. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5 hours, based on a 90 percent confidence interval, following administration of said pharmaceutical composition to said subject in a fed state.

Para. FE. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5.8 hours, based on a 90 percent confidence interval, following administration of said pharmaceutical composition to said subject in a fed state.

Para. FF. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Tmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 5.4 hours, based on a 90 percent confidence interval, following administration of said pharmaceutical composition to said subject in a fed state.

Para. FG. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2150 nM, based on a 90 percent confidence interval, following administration of said pharmaceutical composition to said subject in a fasted state.

Para. FH. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2260 nM, based on a 90 percent confidence interval, following administration of said pharmaceutical composition to said subject in a fasted state.

Para. FI. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2300 nM, based on a 90 percent confidence interval, following administration of said pharmaceutical composition to said subject in a fasted state.

Para. FJ. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2440 nM, based on a 90 percent confidence interval, following administration of said pharmaceutical composition to said subject in a fed state.

Para. FK. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2600 nM, based on a 90 percent confidence interval, following administration of said pharmaceutical composition to said subject in a fed state.

Para. FL. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an Cmax of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 2400 nM, based on a 90 percent confidence interval, following administration of said pharmaceutical composition to said subject in a fed state.

Para. FM. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 52,900 nM*hr, based on a 90 percent confidence interval, following administration of said pharmaceutical composition to said subject in a fasted state.

Para. FN. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 56,100 nM*hr, based on a 90 percent confidence interval, following administration of said pharmaceutical composition to said subject in a fasted state.

Para. FO. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 57,200 nM*hr, based on a 90 percent confidence interval, following administration of said pharmaceutical composition to said subject in a fasted state.

Para. FP. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 58,800 nM*hr, based on a 90 percent confidence interval, following administration of said pharmaceutical composition to said subject in a fed state.

Para. FQ. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 71,800 nM*hr, based on a 90 percent confidence interval, following administration of said pharmaceutical composition to said subject in a fed state.

Para. FR. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(0 to 120) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 64,400 nM*hr, based on a 90 percent confidence interval, following administration of said pharmaceutical composition to said subject in a fed state.

Para. FS. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 53,800 nM*hr, based on a 90 percent confidence interval, following administration of said pharmaceutical composition to said subject in a fasted state.

Para. FT. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 57,200 nM*hr, based on a 90 percent confidence interval, following administration of said pharmaceutical composition to said subject in a fasted state.

Para. FU. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 58,300 nM*hr, based on a 90 percent confidence interval, following administration of said pharmaceutical composition to said subject in a fasted state.

Para. FV. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 59,400 nM*hr, based on a 90 percent confidence interval, following administration of said pharmaceutical composition to said subject in a fed state.

Para. FW. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 73,300 nM*hr, based on a 90 percent confidence interval, following administration of said pharmaceutical composition to said subject in a fed state.

Para. FX. A pharmaceutical composition, comprising:
N-[5-(3,5-difluorobenzyl)-1H-indazol-3-yl]-4-(4-methyl-piperazin-1-yl)-2-(tetrahydro-pyran-4-ylamino)-benzamide; and
means for delivering an AUC(infinity) of said N-[5-(3,5-difluorobenzyl)-1H-indazol-3-yl]-4-(4-methyl-piperazin-1-yl)-2-(tetrahydro-pyran-4-ylamino)-benzamide in the plasma of a subject that is between 80% to 125% of 65,700 nM*hr, based on a 90 percent confidence interval, following administration of said pharmaceutical composition to said subject in a fed state.

Para. FY. The pharmaceutical composition of any one of Paras. CA-ED, wherein said at least one acidulant is tartaric acid.

Para. FZ. The pharmaceutical composition of any one of Paras. CA-FY, wherein said composition comprises a total dose of about 600 mg of said N-[5-(3,5-difluorobenzyl)-1H-indazol-3-yl]-4-(4-methyl-piperazin-1-yl)-2-(tetrahydro-pyran-4-ylamino)-benzamide.

Para. GA. The pharmaceutical composition of any one of Paras. CA-FZ, wherein said pharmaceutical composition is in the form of a tablet or capsule.

Para. GB. The pharmaceutical composition of any one of Paras. CA-GA, wherein said pharmaceutical composition is in the form of a capsule.

Para. GC. The pharmaceutical composition of any one of Paras. A-GB further comprising lactose, hypromellose, crospovidone, microcrystalline cellulose, colloidal silicon dioxide, or magnesium stearate, or any combination of two or more thereof.

Para. GD. The pharmaceutical composition of Para. GC comprising about 20% w/w to about 60% w/w N-[5-(3,5-difluorobenzyl)-1H-indazol-3-yl]-4-(4-methyl-piperazin-1-yl)-2-(tetrahydro-pyran-4-ylamino)-benzamide, about 5% w/w/to about 20% w/w tartaric acid, about 15% w/w to about 35% w/w lactose, about 1% w/w to about 10% w/w hypromellose, about 1% w/w to about 5% w/w microcrystalline cellulose, about 1% w/w to about 10% w/w crospovidone, about 0.05% w/w to about 5% w/w colloidal silicon dioxide, and about 0.1% w/w to about 5% w/w magnesium stearate.

Para. GE. The pharmaceutical composition of Para. GC comprising about 40% w/w to about 50% w/w N-[5-(3,5-difluorobenzyl)-1H-indazol-3-yl]-4-(4-methyl-piperazin-1-yl)-2-(tetrahydro-pyran-4-ylamino)-benzamide, about 10% w/w/to about 15% w/w tartaric acid, about 25% w/w to about 30% w/w lactose, about 3% w/w to about 5 w/w hypromellose (hydroxypropyl methylcellulose), about 2% w/w to about 4% w/w microcrystalline cellulose, about 4% w/w to about 7% w/w crospovidone, about 0.1% w/w to about 1% w/w colloidal silicon dioxide, and about 0.5% w/w to about 2% w/w magnesium stearate.

Para. GF. The pharmaceutical composition of any one of Paras. GC-GE, wherein lactose is anhydrous lactose.

Para. GG. The pharmaceutical composition of any one of Paras. A-GF, wherein N-[5-(3,5-difluorobenzyl)-1H-indazol-3-yl]-4-(4-methyl-piperazin-1-yl)-2-(tetrahydro-pyran-4-ylamino)-benzamide and the at least one acidulant are present in the composition as an admixture. In other words, N-[5-(3,5-difluorobenzyl)-1H-indazol-3-yl]-4-(4-methyl-piperazin-1-yl)-2-(tetrahydro-pyran-4-ylamino)-benzamide is not present in the composition as the salt form of the at least one acidulant.

Para. GH. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide, tartaric acid, anhydrous lactose, hypromellose, microcrystalline cellulose, crospovidone, colloidal silicon dioxide, and magnesium stearate, wherein the composition is prepared in a method comprising:
  adding N-[5-(3,5-difluorobenzyl)-1H-indazol-3-yl]-4-(4-methyl-piperazin-1-yl)-2-(tetrahydro-pyran-4-ylamino)-benzamide; anhydrous lactose; hypromellose; a first portion of crospovidone; and tartaric acid together and blending to form a first admixture;
  sieving the first admixture to form a sieved first admixture;
  blending the sieved first admixture to form a second admixture;
  sieving the second admixture to form a sieved second admixture;
  blending the sieved second admixture to form a third admixture;
  adding a first portion of magnesium stearate to the third admixture and blending to form a fourth admixture;
  compacting and milling the fourth admixture to form a fifth admixture;
  adding microcrystalline cellulose, a second portion of crospovidone, and colloidal silicon dioxide to the fifth admixture and blending to form a sixth admixture; and
  adding a second portion of magnesium stearate to the sixth admixture and blending to form the pharmaceutical composition.

Para. GI. A method of treating a subject having cancer, the method comprising administering to the subject the pharmaceutical composition of any one of Paras. A-GH.

Para. GJ. A method of treating a subject having ALK, ROS1, TrkA, TrkB, or TrkC positive cancer, or a combination thereof, the method comprising administering to the subject the pharmaceutical composition of any one of Paras. A-GH.

Para. GK. A method of treating a subject having ALK positive cancer, the method comprising administering to the subject the pharmaceutical composition of any one of Paras. A-GH.

Para. GL. A method of treating a subject having ROS1, TrkA, TrkB, or TrkC positive cancer, or a combination thereof, the method comprising administering to the subject the pharmaceutical composition of any one of Paras. A-GH.

Para. GM. A method of treating a subject having ROS1 positive cancer, the method comprising administering to the subject the pharmaceutical composition of any one of Paras. A-GH.

Para. GN. A method of treating a subject having TrkA, TrkB, or TrkC positive cancer, or a combination thereof, the method comprising administering to the subject the pharmaceutical composition of any one of Paras. A-GH.

Para. GO. A method of treating a subject having TrkA positive cancer, the method comprising administering to the subject the pharmaceutical composition of any one of Paras. A-GH.

Para. GP. A method of treating a subject having TrkB positive cancer, the method comprising administering to the subject the pharmaceutical composition of any one of Paras. A-GH.

Para. GQ. A method of treating a subject having TrkC positive cancer, the method comprising administering to the subject the pharmaceutical composition of any one of Paras. A-GH.

Para. GR. A pharmaceutical composition of any one of Paras. A-GH for use in a method of treating a subject having cancer.

Para. GS. A pharmaceutical composition of any one of Paras. A-GH for use in a method of treating a subject having ALK, ROS1, TrkA, TrkB, or TrkC positive cancer, or a combination thereof.

Para. GT. A pharmaceutical composition of any one of Paras. A-GH for use in a method of treating a subject having ALK positive cancer.

Para. GU. A pharmaceutical composition of any one of Paras. A-GH for use in a method of treating a subject having ROS1, TrkA, TrkB, or TrkC positive cancer, or a combination thereof.

Para. GV. A pharmaceutical composition of any one of Paras. A-GH for use in a method of treating a subject having ROS1 positive cancer.

Para. GW. A pharmaceutical composition of any one of Paras. A-GH for use in a method of treating a subject having TrkA, TrkB, or TrkC positive cancer, or a combination thereof.

Para. GX. A pharmaceutical composition of any one of Paras. A-GH for use in a method of treating a subject having TrkA positive cancer.

Para. GY. A pharmaceutical composition of any one of Paras. A-GH for use in a method of treating a subject having TrkB positive cancer.

Para. GZ. A pharmaceutical composition of any one of Paras. A-GH for use in a method of treating a subject having TrkC positive cancer.

Para. HA. Use of the pharmaceutical composition of any one of Paras. A-GH for the preparation of a medicament for the treatment of cancer.

Para. HB. Use of the pharmaceutical composition of any one of Paras. A-GH for the preparation of a medicament for the treatment of ALK, ROS1, TrkA, TrkB, or TrkC positive cancer, or a combination thereof.

Para. HC. Use of the pharmaceutical composition of any one of Paras. A-GH for the preparation of a medicament for the treatment of ALK positive cancer.

Para. HD. Use of the pharmaceutical composition of any one of Paras. A-GH for the preparation of a medicament for the treatment of ROS1, TrkA, TrkB, or TrkC positive cancer, or a combination thereof.

Para. HE. Use of the pharmaceutical composition of any one of Paras. A-GH for the preparation of a medicament for the treatment of ROS1 positive cancer.

Para. HF. Use of the pharmaceutical composition of any one of Paras. A-GH for the preparation of a medicament for the treatment of TrkA, TrkB, or TrkC positive cancer, or a combination thereof.

Para. HG. Use of the pharmaceutical composition of any one of Paras. A-GH for the preparation of a medicament for the treatment of TrkA positive cancer.

Para. HH. Use of the pharmaceutical composition of any one of Paras. A-GH for the preparation of a medicament for the treatment of TrkB positive cancer.

Para. HI. Use of the pharmaceutical composition of any one of Paras. A-GH for the preparation of a medicament for the treatment of TrkC positive cancer.

As will be understood by one skilled in the art, for any and all purposes, such as in terms of providing a written description, all ranges provided herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each subject member. Thus, for example, a group having 1-3 articles refers to groups having 1, 2, or 3 articles. Similarly, a group having 1-5 articles refers to groups having 1, 2, 3, 4, or 5 articles, and so forth.

Headings, e.g., (a), (b), (i) etc, are presented merely for ease of reading the specification and claims. The use of headings in the specification or claims does not require the steps or elements be performed in alphabetical or numerical order or the order in which they are presented.

The above description discloses several methods and materials of the present disclosure. The embodiments disclosed herein are susceptible to modifications in the methods and materials, as well as alterations in the fabrication methods and equipment. Such modifications will become apparent to those skilled in the art from a consideration of this disclosure or practice of the embodiments provided herein. Consequently, it is not intended that the embodiments disclosed herein be limited to the specific embodiments provided herein, but that it cover all modifications and alternatives coming within the true scope and spirit of the disclosure.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide and at least one acidulant present in the pharmaceutical composition as a solid admixture.

2. The pharmaceutical composition of claim 1, wherein said at least one acidulant is an organic acidulant.

3. The pharmaceutical composition of claim 1, wherein said at least one acidulant is selected from tartaric acid, maleic acid, fumaric acid, citric acid, and betaine hydrochloride.

4. The pharmaceutical composition of claim 3, wherein said at least one acidulant is tartaric acid.

5. The pharmaceutical composition of claim 3, wherein said at least one acidulant is fumaric acid.

6. The pharmaceutical composition of claim 3, wherein said fumaric acid is in a micronized form.

7. The pharmaceutical composition of claim 3, wherein said at least one acidulant is maleic acid.

8. The pharmaceutical composition of claim 3, wherein said at least one acidulant is citric acid.

9. The pharmaceutical composition of claim 3, wherein said at least one acidulant is betaine hydrochloride.

10. The pharmaceutical composition of claim 1, wherein the molar ratio between said N-[5-(3,5-difluorobenzyl)-1H-indazol-3-yl]-4-(4-methyl-piperazin-1-yl)-2-(tetrahydro-pyran-4-ylamino)-benzamide and said at least one acidulant is from about 0.5 to about 2.

11. The pharmaceutical composition of claim 1, wherein said pharmaceutical composition is in the form of a tablet or capsule.

12. The pharmaceutical composition of claim 1, wherein said pharmaceutical composition comprises from about 25 mg to about 800 mg of said N-[5-(3,5-difluorobenzyl)-1H-indazol-3-yl]-4-(4-methyl-piperazin-1-yl)-2-(tetrahydro-pyran-4-ylamino)-benzamide.

13. The pharmaceutical composition of claim 4, wherein the particle size of said fumaric acid is such that it passes through a 60-mesh screen.

14. The pharmaceutical composition of claim 1, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide degrades in said pharmaceutical composition after said pharmaceutical composition is stored for 3 months in an open container at 40° C. and 75% relative humidity.

15. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide and at least one pharmaceutically acceptable excipient, wherein said pharmaceutical composition is in the form of a tablet or capsule, and wherein said tablet or capsule has a dissolution profile wherein at least about 30% of said N-[5-(3,5-difluorobenzyl)-1H-indazol-3-yl]-4-(4-methyl-piperazin-1-yl)-2-(tetrahydro-pyran-4-ylamino)-benzamide has been released from said tablet or capsule at about 60 minutes when tested in USP Apparatus Type I Basket Method at 50 rpm in 500 mL of sodium acetate buffer at a pH of 4.5 and at about 37° C.

16. The pharmaceutical composition of claim 1, wherein said pharmaceutical composition further comprises mannitol or isomalt.

17. The pharmaceutical composition of claim 16, wherein said pharmaceutical composition further comprises starch.

18. The pharmaceutical composition of claim 17, wherein the weight to weight ratio of said mannitol or isomalt to said starch in said pharmaceutical composition is from about 1 to 1 to about 3 to 1.

19. The pharmaceutical composition of claim 1, wherein said pharmaceutical composition when administered to a subject in a fasted state provides a pharmacokinetic profile in said subject wherein the $T_{max}$ of said N-[5-(3,5-difluorobenzyl)-1H-indazol-3-yl]-4-(4-methyl-piperazin-1-yl)-2-(tetrahydro-pyran-4-ylamino)-benzamide in the plasma of said subject is between about 2 hours and 6 hours following said administration of said pharmaceutical composition to said subject.

20. The pharmaceutical composition of claim 1, wherein said pharmaceutical composition exhibits no food effect when administered to a subject.

21. The pharmaceutical composition of claim 1 further comprising lactose, hypromellose, crospovidone, microcrystalline cellulose, colloidal silicon dioxide, or magnesium stearate, or any combination of two or more thereof.

22. The pharmaceutical composition of claim 21 comprising about 20% w/w to about 60% w/w N-[5-(3,5-difluorobenzyl)-1H-indazol-3-yl]-4-(4-methyl-piperazin-1-yl)-2-(tetrahydro-pyran-4-ylamino)-benzamide, about 5% w/w/ to about 20% w/w tartaric acid, about 15% w/w to about 35% w/w lactose, about 1% w/w to about 10% w/w hypromellose, about 1% w/w to about 5% w/w microcrystalline cellulose, about 1% w/w to about 10% w/w crospovidone, about 0.05% w/w to about 5% w/w colloidal silicon dioxide, and about 0.1% w/w to about 5% w/w magnesium stearate.

23. The pharmaceutical composition of claim 21 comprising about 40% w/w to about 50% w/w N-[5-(3,5-difluorobenzyl)-1H-indazol-3-yl]-4-(4-methyl-piperazin-1-yl)-2-(tetrahydro-pyran-4-ylamino)-benzamide, about 10% w/w/ to about 15% w/w tartaric acid, about 25% w/w to about 30% w/w lactose, about 3% w/w to about 5 w/w hypromellose (hydroxypropyl methylcellulose), about 2% w/w to about 4% w/w microcrystalline cellulose, about 4% w/w to about 7% w/w crospovidone, about 0.1% w/w to about 1% w/w colloidal silicon dioxide, and about 0.5% w/w to about 2% w/w magnesium stearate.

24. The pharmaceutical composition of claim 21, wherein lactose is anhydrous lactose.

25. A pharmaceutical composition comprising N-[5-(3,5-difluorobenzyl)-1H-indazol-3-yl]-4-(4-methyl-piperazin-1-yl)-2-(tetrahydro-pyran-4-ylamino)-benzamide, tartaric acid, anhydrous lactose, hypromellose, microcrystalline cellulose, crospovidone, colloidal silicon dioxide, and magnesium stearate, wherein the composition is prepared in a method comprising:
- adding N-[5-(3,5-difluorobenzyl)-1H-indazol-3-yl]-4-(4-methyl-piperazin-1-yl)-2-(tetrahydro-pyran-4-ylamino)-benzamide; anhydrous lactose; hypromellose; a first portion of crospovidone; and tartaric acid together and blending to form a first solid admixture;
- sieving the first solid admixture to form a sieved first solid admixture;
- blending the sieved first solid admixture to form a second solid admixture;
- sieving the second solid admixture to form a sieved second solid admixture;
- blending the sieved second solid admixture to form a third solid admixture;
- adding a first portion of magnesium stearate to the third solid admixture and blending to form a fourth solid admixture;
- compacting and milling the fourth solid admixture to form a fifth solid admixture;
- adding microcrystalline cellulose, a second portion of crospovidone, and colloidal silicon dioxide to the fifth solid admixture and blending to form a sixth solid admixture; and
- adding a second portion of magnesium stearate to the sixth solid admixture and blending to form the pharmaceutical composition.

* * * * *

UNITED STATES PATENT AND TRADEMARK OFFICE
CERTIFICATE OF CORRECTION

PATENT NO. : 10,398,693 B2
APPLICATION NO. : 16/039196
DATED : September 3, 2019
INVENTOR(S) : Daniel Codallos, Jr. et al.

Page 1 of 1

It is certified that error appears in the above-identified patent and that said Letters Patent is hereby corrected as shown below:

In the Claims

At Column 178, Line 20, Claim 13 "13. The pharmaceutical composition of claim 4, wherein" should be -- 13. The pharmaceutical composition of claim 5, wherein --

Signed and Sealed this
Seventeenth Day of March, 2020

Andrei Iancu
*Director of the United States Patent and Trademark Office*